United States Patent
Tanabe et al.

(10) Patent No.: US 10,172,356 B2
(45) Date of Patent: Jan. 8, 2019

(54) BIPYRIDINE COMPOUND AND USE OF SAME FOR NOXIOUS ARTHROPOD CONTROL

(71) Applicant: Sumitomo Chemical Company, Limited, Tokyo (JP)

(72) Inventors: Takamasa Tanabe, Takarazuka (JP); Yoshihiko Nokura, Takarazuka (JP); Ryota Maehata, Takarazuka (JP); Kohei Orimoto, Takarazuka (JP); Yuji Nakajima, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/547,112

(22) PCT Filed: Jan. 29, 2016

(86) PCT No.: PCT/JP2016/052788
§ 371 (c)(1),
(2) Date: Jul. 28, 2017

(87) PCT Pub. No.: WO2016/121970
PCT Pub. Date: Aug. 4, 2016

(65) Prior Publication Data
US 2018/0310559 A1 Nov. 1, 2018

(30) Foreign Application Priority Data
Jan. 30, 2015 (JP) ............................. 2015-016525

(51) Int. Cl.
*A01N 43/40* (2006.01)
*C07D 213/71* (2006.01)

(52) U.S. Cl.
CPC .......... *A01N 43/40* (2013.01); *C07D 213/71* (2013.01)

(58) Field of Classification Search
None
See application file for complete search history.

(56) References Cited

U.S. PATENT DOCUMENTS

2003/0069242 A1   4/2003   Toriyabe et al.

FOREIGN PATENT DOCUMENTS

| JP | 2000-026421 A | 1/2000 |
| JP | 2000198768 A | 7/2000 |
| JP | 201360420 A | 4/2013 |
| WO | 2012106495 A1 | 8/2012 |
| WO | 2013027660 A1 | 2/2013 |

OTHER PUBLICATIONS

Extended European Search Report issued Jun. 21, 2018 in EP Application No. 16743573.4.
U.S. Appl. No. 15/547,162, filed Jul. 28, 2017, by Tanabe.
Int'l Preliminary Report on Patentability dated Aug. 1, 2017 in Int'l Application No. PCT/JP2016/052788.
Int'l Search Report dated Apr. 5, 2016 in Int'l Application No. PCT/JP2016/052788.

*Primary Examiner* — Alicia L Otton
(74) *Attorney, Agent, or Firm* — Panitch Schwarze Belisario & Nadel LLP

(57) ABSTRACT

A bipyridine compound having an excellent controlling effect against noxious arthropods is provided. In particular, a bipyridine compound of formula (I) or an N-oxide thereof is provided in which the variable groups are as described in the specification. Also provided are compositions containing the bipyridine compound or an N-oxide thereof, and methods of using such compounds and compositions to control noxious arthropods.

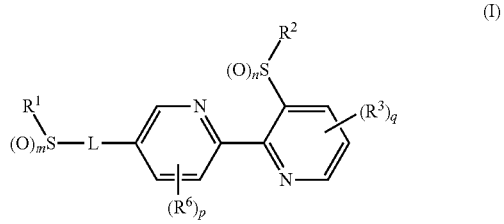

(I)

14 Claims, No Drawings

BIPYRIDINE COMPOUND AND USE OF SAME FOR NOXIOUS ARTHROPOD CONTROL

CROSS-REFERENCE TO RELATED APPLICATION

This application is a Section 371 of International Application No. PCT/JP2016/052788, filed Jan. 29, 2016, which was published in the Japanese language on Aug. 4, 2016, under International Publication No. WO 2016/121970 A1, and the disclosure of which is incorporated herein by reference.

TECHNICAL FIELD

This application claims priority to and the benefit of Japanese Patent Application No. 2015-016525 filed Jan. 30, 2015, the entire contents of which are incorporated herein by reference.

The present invention is related to a certain class of bipyridine compound and its use for controlling harmful arthropods.

BACKGROUND ART

To date, some compounds for controlling harmful arthropods have been developed and come into practical use. Also, a certain class of heterocyclic compound has been known (see Patent Document 1).

CITATION LIST

Patent Document

Patent Document 1: JP 2002-26421 A

SUMMARY OF THE INVENTION

Problems to be Solved by Invention

An object of the present invention is to provide a compound having an excellent efficacy for controlling harmful arthropods.

Means To Solve Problems

[1] A bipyridine compound represented by formula (I) or its N oxide compound:

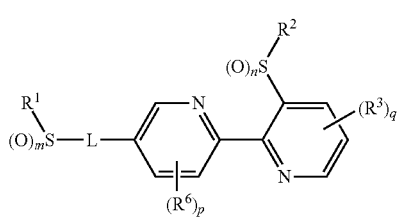

(I)

[wherein

L represents a single bond or an oxygen atom, and when L represents an oxygen atom, m represents 2;

$R^1$ represents a C1-C10 chain hydrocarbon group having one or more halogen atoms, a (C1-C5 alkoxy) C2-C5 alkyl group having one or more halogen atoms, a (C1-C5 alkylsulfanyl) C2-C5 alkyl group having one or more halogen atoms, a (C1-C5 alkylsulfinyl) C2-C5 alkyl group having one or more halogen atoms, a (C1-C5 alkylsulfonyl) C2-C5 alkyl group having one or more halogen atoms, a (C3-C7 cycloalkyl) C1-C3 alkyl group having one or more substituents selected from Group G, or a C3-C7 cycloalkyl group having one or more substituents selected from Group G;

$R^2$ represents a C1-C6 alkyl group optionally having one or more halogen atoms;

$R^3$ represents a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{24}NR^{11}R^{12}$, a $NR^{11}C(O)R^{13}$, a $NR^{24}NR^{11}C(O)R^{13}$, a $NR^{11}C(O)OR^{14}$, a $NR^{24}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{12}R^{12}$, a cyano group, a nitro group, or a halogen atom;

q is 0, 1, 2, or 3, and when p is 2 or 3, a plurality of $R^3$ may be identical or different;

$R^6$ represents a C1-C6 alkyl group optionally having one or more halogen atoms, a $OR^{18}$, a $NR^{18}R^{19}$, a $C(O)OR^{25}$, a $OC(O)R^{20}$, a cyano group, a nitro group, or a halogen atom;

p is 0, 1, 2, or 3, and when p is 2 or 3, a plurality of $R^3$ may be identical or different;

$R^{11}$, $R^{17}$, $R^{18}$, $R^{19}$, $R^{20}$, $R^{24}$ and $R^{25}$ represent independently of each other a hydrogen atom, or a C1-C6 chain hydrocarbon group optionally having one or more halogen atoms;

$R^{12}$ represents a hydrogen atom, a C1-C6 chain hydrocarbon group optionally having one or more halogen atoms, a C1-C6 alkyl group having one substituent selected from Group F, or a $S(O)_2R^{23}$;

$R^{23}$ represents a C1-C6 chain hydrocarbon group optionally having one or more halogen atoms, or a phenyl group optionally having one or more substituents selected from Group D, $R^{11a}$ and $R^{12a}$ combine together with a nitrogen atom to which they are attached to form a 3 to 7 membered nonaromatic heterocyclic group {the 3 to 7 membered nonaromatic heterocyclic group represents aziridine, azetidine, pyrrolidine, imidazoline, imidazolidine, piperidine, tetrahydropyrimidine, hexahydropyrimidine, piperazine, azepane, oxazolidine, isooxazolidine, 1,3-oxazinane, morpholine, 1,4-oxazepane, thiazolidine, isothiazolidine, 1,3-thiazinane, thiomorpholine, or 1,4-thiazepane, which may optionally have one or more substituents selected from Group E};

$R^{13}$ represents a hydrogen atom, a C1-C6 chain hydrocarbon group optionally having one or more halogen atoms, a C3-C7 cycloalkyl group optionally having one or more halogen atoms, a (C3-06 cycloalkyl) C1-C3 alkyl group optionally having one or more halogen atoms, a phenyl group optionally having one or more substituents selected from Group D, or a 5 or 6 membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, or a phenyl C1-C3 alkyl group {the phenyl group in the group may optionally have one or more substituents selected from Group D};

$R^{15}$ and $R^{16}$ represent independently of each other, a C1-C6 alkyl group optionally having one or more halogen atoms;

n is 0, 1 or 2
m is 0, 1 or 2;
x is 0 or 1;
y is 0, 1 or 2;

Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom ({$R^{21}$ and $R^{22}$ represent independently of each other a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, a $NHR^{21}$, a $NR^{21}R^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3 to 7 membered nonaromatic heterocyclic group optionally having one or more substituents selected from Group C;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group G: a group consisting of a halogen atom, and a C1-C6 haloalkyl group]
(hereinafter, a bipyridine compound represented by formula (I) or its N oxide compound is referred to as Compound A).

[2] The compound described in [1] wherein $R^2$ represents an ethyl group.

[3] The compound described in [1] or [2] wherein $R^1$ represents a C1-C10 fluoroalkyl group.

[4] The compound described in [1] or [2] wherein $R^1$ represents a C1-C10 fluoroalkyl group having two or more fluoro atoms.

[5] The compound described in [1] or [2] wherein $R^1$ represents a C1-C10 perfluoroalkyl group.

[6] The compound described in any one of [1] to [5] wherein L represents a single bond.

[7] The compound described in any one of [1] to [6] wherein
q is 0 or 1, and
$R^3$ represents a halogen atom, or a C1-C6 alkyl group optionally having one or more halogen atoms.

[8] The compound described in [1] wherein
$R^1$ represents a C1-C10 fluoroalkyl group,
$R^2$ represents an ethyl group,
$R^3$ represents a halogen atom, or a C1-C6 alkyl group optionally having one or more halogen atoms, and
$R^6$ represents a halogen atom, or a C1-C6 alkyl group optionally having one or more halogen atoms.

[9] The compound described in [1] wherein
$R^1$ represents a C1-C10 perfluoroalkyl group,
$R^2$ represents an ethyl group,
$R^3$ represents a halogen atom, or a C1-C6 alkyl group optionally having one or more halogen atoms, and
p is 0.

[10] The compound described in [1] wherein
$R^1$ represents a C1-C10 perfluoroalkyl group,
$R^2$ represents an ethyl group, and
p and p are independently of each other 0.

[11] A bipyridine compound represented by formula (100):

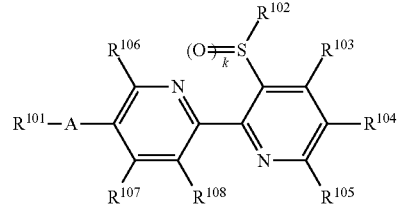

(100)

[wherein
A represents a $S(O)_j$;
$R^{101}$ represents a C2-C10 haloalkyl group, or a (C1-C5 alkoxy) C2-C5 alkyl group having or more halogen atoms,
$R^{102}$ represents a C1-C6 alkyl group optionally having one or more halogen atoms,
$R^{103}$, $R^{104}$, $R^{105}$, $R^{106}$, $R^{107}$, and $R^{108}$ represent independently of each other a hydrogen atom, a halogen atom, or a C1-C6 alkyl group optionally having one or more halogen atoms,
j is 0, 1, or 2; and
k is 0, 1, or 2.]
(hereinafter, a bipyridine compound represented by formula (100) referred to as Compound B).

[12] The compound described in [11] wherein
$R^{101}$ represents a C2-C10 fluoroalkyl group having two or more fluoro atoms, or a (C1-C5 alkoxy) C2-C5 alkyl group having two or more halogen atoms,
$R^{102}$ represents an ethyl group,
$R^{103}$, $R^{104}$, $R^{105}$, $R^{106}$, $R^{107}$, and $R^{108}$ represent independently of each other a hydrogen atom.

[13] A composition for controlling harmful arthropod comprising the compound described in any one of [1] to [12] and an inert carrier.

[14] A method for controlling a harmful arthropod which comprises applying an effective amount of the compound described in any one of [1] to [12] to a harmful arthropod or a habitat where a harmful arthropod lives.

Effect of Invention

Compound A has an excellent control efficacy against harmful arthropods, and is thus useful as an active ingredient for an agent for controlling harmful arthropods.

MODE FOR CARRYING OUT THE INVENTION

The substituent(s) as described herein is/are explained.

The term of "optionally having one or more halogen atoms" represents that when two or more halogen atoms are present, these halogen atoms may be identical to or different from each other.

The expression of "CX-CY" as used herein represents that the number of carbon atom is from X to Y. For example, the expression of "C1-C6" represents that the number of carbon atom is from 1 to 6.

The term "halogen atom" represents fluorine atom, chlorine atom, bromine atom, or iodine atom.

Example of "N oxide compound" includes compound represented by formula (Id), a compound represented by formula (Ie), and a compound represented by formula (If).

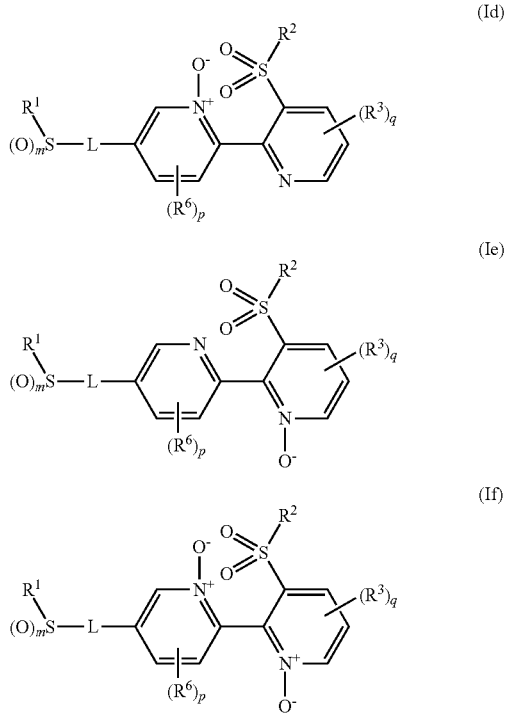

Example of the term of "$R^{11a}$ and $R^{12a}$ combine together with a nitrogen atom to which they are attached to form a 3 to 7 membered nonaromatic heterocyclic group" {the 3 to 7 membered nonaromatic heterocyclic group represents aziridine, azetidine, pyrrolidine, imidazoline, imidazolidine, piperidine, tetrahydropyrimidine, hexahydropyrimidine, piperazine, azepane, oxazolidine, isooxazolidine, 1,3-oxazinane, morpholine, 1,4-oxazepane, thiazolidine, isothdazolidine, 1,3-thiazinane, thiomorpholine, or 1,4-thiazepane, which may optionally have one or more substituents selected from Group E}" includes the following groups:

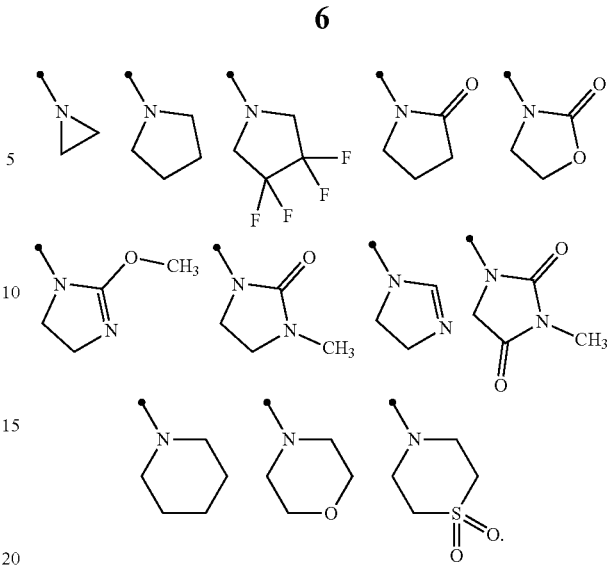

Example of the term of "cycloalkyl group" includes cyclopropyl group, cyclobutyl group, cyclopentyl group, cyclohexyl group, and cycloheptyl group.

Example of the term of "phenylC1-C3 alkyl group {the phenyl group in the group may optionally have one or more substituents selected from Group D}] includes benzyl group, 2-fluorobenzyl group, 4-chlorobenzyl group, 4-(trifluoromethyl) benzyl group, and 2-[4-(trifluoromethyl)phenyl]ethyl group.

The term of "chain hydrocarbon group" represents an alkyl group, an alkenyl group, or an alkynyl group.

Example of the term of "alkyl group" include methyl group, ethyl group, propyl group, isopropyl group, 1,1-dimethylpropyl group, 2,2-dimethylpropyl group, 1,2-dimethylpropyl group, 1-ethylpropyl group, butyl group, sec-butyl group, isobutyl group, tert-butyl group, 1-methylbutyl group, 2-methylbutyl group, 3-methylbutyl group, 1,1-dimethylbutyl group, 2,2-dimethylbutyl group, 3,3-dimethylbutyl group, 1-ethylbutyl group, 2-ethylbutyl group, pentyl group, 1-methypentyl group, 2-methylpentyl group, 3-methylpentyl group, 4-methylpentyl group, hexyl group, heptyl group, octyl group, nonyl group, and decyl group.

Example of the term of "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 1-ethyl-1-propenyl group, 1-ethyl-2-propenyl group, 3-butenyl group, 4-pentenyl group, and 5-hexenyl group, heptenyl group, octenyl group, nonenyl group, and decenyl group.

Example of the term of "alkynyl group" includes ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, 5-hexynyl group, heptynyl group, octinyl group, nonynyl group, and decynyl group.

The term of "(C1-C5 alkoxy) C2-C5 alkyl group having one or more halogen atoms" represents a group wherein the (C1-C5 alkoxy) and/or the (C2-C5 alkyl ) have/has one or more halogen atoms, and, for example, includes a (C1-C5 haloalkoxy) C2-C5 haloalkyl group such as 2,2-difluoro-3-(2,2,2-trichloroethoxy)propyl group, a (C1-C5 haloalkoxy) C2-C5 alkyl group such as 2-(2,2,2-trichloroethoxy)ethyl group, a (C1-C5 alkoxy) C2-C5 haloalkyl group such as 2,2-difluoro-3-methoxypropyl group, a (C1-C5 fluoroalkoxy) C2-C5 fluoroalkyl group such as 1,1,2-trifluoro-2-(trifluoromethoxy)ethyl group, 2,2-difluoro-3-(2,2,2-trifluoroethoxy)propyl group, a (C1-C5 fluoroalkoxy) C2-C5 alkyl group such as 2-(2,2,2-trifluoroethoxy)ethyl group, and a (C1-C5 alkoxy) C2-C5 fluoroalkyl group such as 2,2-difluoro-3-methoxypropyl group.

The term of "C1-C10 haloalkyl group" represents that a group wherein one or more hydrogen atoms in the C1-C10 alkyl group is/are substituted by a halogen atom, and includes, for example, 2,2,2-trifluoroethyl group, 2,2,2-trichloroethyl group, and 2,2,3,3-tetrafluoropropyl group.

The term of "C1-C10 fluoroalkyl group" represents a group wherein one or more hydrogen atom(s) (for example, two or more) in the C1-C10 alkyl group is/are substituted by a fluorine atom, and includes, for example, 2,2,2-trifluoroethyl group, and 2,2,3,3-tetrafluoropropyl group. Also the term of "C1-C10 perfluoroalkyl group" represents a group wherein all hydrogen atoms in the C1-C10 alkyl group are substituted by a fluorine atom.

The term of "C3-C10 haloalkenyl group" represents that a group wherein one or more hydrogen atoms ire the C3-C10 alkenyl group is/are substituted by a halogen atom, and includes, for example, 3,3,3-trifluoro-1-propeny group, 3,3,3-trichloro-1-propeny group, and 2,2,3,3-tetrafluoro-1-propeny group.

The term of "C3-C10 haloalkynyl group" represents that a group wherein one or more hydrogen atoms in the C3-C10 alkynyl group is/are substituted by a halogen atom, and includes, for example, 3,3,3-trifluoro-1-propynyl group, and 3,3,3-trichloro-1-propynyl group.

The term of "(C1-C5 fluoroalkoxy) C2-C5 fluoroalkyl group" represents a group wherein one hydrogen atom in the C2-C5 fluoroalkyl group is substituted by a C1-C5 fluoroalkoxy group, and includes, for example, 1,1,2-trifluoro-2-(trifluoromethoxy)ethyl group.

The term of "C1-C5 fluoroalkoxy group" represents a group wherein one or more hydrogen atoms is/are substituted by a fluorine atom, and includes, for example, trifluoromethoxy group, difluoromethoxy group, and 2,2,2-trifluoroethoxy.

The term of "(C1-C5 haloalkoxy) C2-C5 haloalkyl group" represents a group wherein one hydrogen atom in the C2-C5 haloalkyl group is substituted by a C1-C5 haloalkoxy group, and includes, for example, 1,1,2-trifluoro-2-(trifluoromethoxy)ethyl group.

The term of "C1-C6 haloalkoxy group" represents a group wherein one or more hydrogen atoms in the C1-C6 alkyl group is/are substituted by halogen atoms, and includes, for example, trifluoromethoxy group, difluoromethoxy group, 2,2,2-trichloromethoxy group, and 2,2,2-trifluoroethoxy.

The term of "C3-C6 haloalkenyloxy group" represents a group wherein one or more hydrogen atoms in the C3-C6 alkenyloxy group is/are substituted by halogen atoms, and includes, for example, 3,3,3-trifluoro-1-propenyloxy group, 3,3,3-trichloro-1-propenyloxy group, and 2,3,3,3-tetrafluoro-1-propenyloxy group.

The term of "C3-C6 haloakynyloxy group" represents a group wherein one or more hydrogen atoms in the C3-C6 alkynyloxy group is/are substituted by halogen atoms, and includes, for example, 3,3,3-trifluoro-1-propynyloxy group, and 3,3,3-trichloro-1-propynyloxy group.

The terms of "alkylsulfanyl", "alkylsulfinyl", and "alkylsulfonyl" represent an alkyl group containing a S(O)z moiety, respectively.

For example, example of the "alkylsulfanyl" when z is 0 includes methylsulfanyl group, ethylsulfanyl group, propylsulfanyl group, and isopropylsulfanyl group.

For example, example of the "alkylsulfinyl" when z is 1 includes methylsulfinyl group, ethylsulfinyl group, propylsulfinyl group, and isopropylsulfinyl group.

For example, example of the "alkylsulfonyl" when z is includes methylsulfonyl group, ethylsulfonyl group, propylsulfonyl group, and isopropylsulfonyl group.

The term of "(C1-C5 alkylsulfanyl) C2-C5 alkyl group having one or more halogen atoms" represents a group wherein the (C1-C5 alkylsulfanyl) and/or the (C2-C5 alkyl) have/has one or more halogen atoms, and includes, for example, 2,2-difluoro-2-(trifluoromethylthio))ethyl group.

The term of "(C1-C5 alkylsulfinyl) C2-C5 alkyl group having one or more halogen atoms" represents a group wherein the (C1-C5 alkylsulfinyl) and/or the (C2-C5 alkyl) have/has one or more halogen atoms, and includes, for example, 2,2-difluoro-2-(trifluoromethansulfinyl)ethyl group.

The term of "(C1-C5 alkylsulfonyl) C2-C5 alkyl group optionally having one or more halogen atoms" represents a group wherein the C1-C5 alkylsulfonyl) and/or the (C2-C5 alkyl) group have/has one or more halogen atoms, and includes, for example, 2,2-difluoro-2-(trifluoromethansulfonyl)ethyl group.

The term of "(C3-C6 cycloalkyl) C1-C3 alkyl group having one or more halogen atoms" represents a group wherein the (C3-C6 cycloalkyl) and/or the (C1-C3 alkyl) has/have one or more substituents selected from Group G, and includes, for example, (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2,-tetrafluoroethyl group, and 2-cyclopropyl-3,3,3-trifluoropropyl group.

The term of "(C3-C7 cycloalkyl) C1-C3 alkyl group having one or more substituents selected from Group G" represents a group wherein the (C3-C7 cycloalkyl) and/or the (C1-C3 alkyl) has/have one or more substituents selected from Group G, and includes, for example, (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2-tetrafluoroethyl group, and 2-cyclopropyl-3,3,3-trifluoropropyl group.

The term of "C3-C7 cycloalkyl group having one or more halogen atoms" includes, for example, 2,2-difluorocyclopropyl group.

The term of "C3-C7 cycloalkyl group having one or more substituents selected from Group G" includes, for example, 2,2 -difluorocyclopropyl group, 1-(2,2,2-trifluoroethyl)cyclopropyl group, and 4-trifluoromethyl) cyclohexyl group.

The term of "5 or 6 members aromatic heterocyclic group" represents pyrrolyl group, furyl group, thienyl group, pyrazolyl group, imidazolyl group, triazolyl group, tetrazolyl group, oxazolyl group, isoxazolyl group, thiazolyl group, oxadiazol group, thiadiazolyl group, pyridyl group, pyridazinyl group, pyrimidinyl group or pyrazinyl group.

The term of "5 membered aromatic heterocyclic group containing one to four nitrogen atoms" represents pyrrolyl group, pyrazolyl group, imidazolyl group, 1,2,4-triazolyl group, 1,2,3-triazolyl group, and tetrazolyl group.

Embodiments of Compound A include the following compounds.

[Embodiment 1] a compound A wherein $R^1$ represents a C1-C10 chain hydrocarbon group having two or more fluoro atoms or a (C1-C5 fluoroalkoxy) C2-C5 fluoroalkyl;

[Embodiment 2] a compound A wherein R¹ represents a C1-C10 chain hydrocarbon group having one or more halogen atoms;
[Embodiment 3] a compound A wherein R¹ represents a C1-C10 chain hydrocarbon group having two or more fluoro atoms;
[Embodiment 4] a compound A wherein R¹ represents a C1-C10 chain hydrocarbon group having three or more fluoro atoms;
[Embodiment 5] compound A wherein R¹ represents a C1-C10 haloalkyl group;
[Embodiment 6] a compound A wherein R¹ represents a C1-C10 fluoroalkyl group having two or more fluoro atoms;
[Embodiment 7] a compound A wherein R¹ represents a C1-C10 perfluoroalkyl group;
[Embodiment 8] a compound A wherein R¹ represents a C1-C3 alkyl group optionally having one or more halogen atoms;
[Embodiment 9] a compound A wherein R² represents a C1-C6 alkyl group;
[Embodiment 10] a compound A wherein R² represents a C1-C3 alkyl group;
[Embodiment 11] a compound A wherein R² represents a methyl group or an ethyl group;
[Embodiment 12] a compound A wherein R² represents an ethyl group;
[Embodiment 13] a compound A wherein R³ represents C1-C6 chain hydrocarbon group optionally having one or more substituents selected from Group B, a 5 membered aromatic heterocyclic group selected from group Q (wherein the 5 membered aromatic heterocyclic group may have optionally one or more substituents selected from Group D), a OR¹², a NR¹¹R¹², a NR¹¹ᵃR¹²ᵃ, a NR²⁴NR¹¹R¹², or a halogen atom, Group Q:

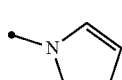 Q-1

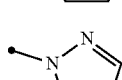 Q-2

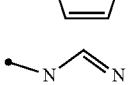 Q-3

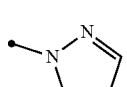 Q-4

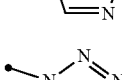 Q-5

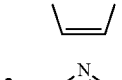 Q-6

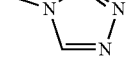 Q-7

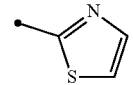 Q-8

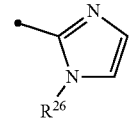 Q-9

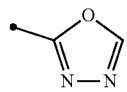 Q-10

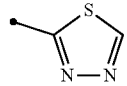 Q-11

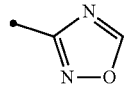 Q-12

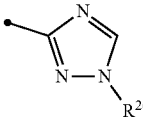 Q-13

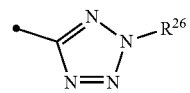 Q-14

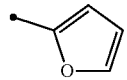 Q-15

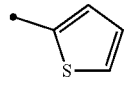 Q-16

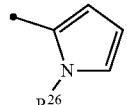 Q-17

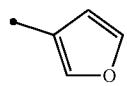 Q-18

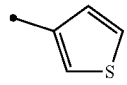 Q-19

Q-20

{wherein R²⁶ represents a C1-C6 alkyl group optionally having one or more halogen atoms};

[Embodiment 14] a compound A wherein R³ represents a C1-C6 alkyl group optionally having one or more halogen atoms, a 1,2,4-triazol-1-yl group optionally having one or more halogen atom, a NR¹¹R¹², a NR²⁴NR¹¹R¹², or a halogen atom, and R¹¹, R¹² and R²⁴ represent independently of each other a hydrogen atom, or a C1-C3 alkyl group optionally having one or more halogen atoms;

[Embodiment 15] a compound A wherein $R^3$ represents a C1-C6 chain hydrocarbon group optionally having one or more halogen atoms, or a halogen atom;

[Embodiment 16] compound A wherein $R^3$ represents a C1-C6 alkyl group having one or more halogen atoms, or a hydrogen atom;

[Embodiment 17] a compound A wherein $R^6$ represents a C1-C8 alkyl group having one or more halogen atoms, or a hydrogen atom;

[Embodiment 18] a compound A wherein q is 0 or 1;

[Embodiment 19] a compound A wherein q is 0;

[Embodiment 20] a compound A wherein p is 0 or 1;

[Embodiment 21] a compound A wherein p is 0;

[Embodiment 22] a compound A wherein $R^2$ represents a methyl group or an ethyl group, $R^6$ represents a C1-C6 alkyl group optionally having one or more halogen atoms, or a halogen atom, q is 0 or 1, and p is 0 or 1;

[Embodiment 23] a compound A wherein $R^1$ represents a C1-C10 chain hydrocarbon group having one or more halogen atoms, and $R^2$ represents an ethyl group;

[Embodiment 24] a compound A wherein
$R^1$ represents a C1-C10 chain hydrocarbon group having one or more halogen atoms,
$R^2$ represents an ethyl group,
$R^3$ represents a C1-C10 chain hydrocarbon group optionally having one or more substituents selected from group B, a 5 membered aromatic heterocyclic group selected from group Q (wherein the 5 membered aromatic heterocyclic group may have optionally one or more substituents selected from Group D), a $OR^{12}$, a $NR^{11}R^{12}$, a $NR^{11a}R^{12a}$, a $NR^{24}NR^{11}R^{12}$, or a halogen atom, and
$R^6$ represents a C1-C6 alkyl group optionally having one or more halogen atoms, or a halogen atom;

[Embodiment 25] a compound A wherein
$R^1$ represents a C1-C10 chain hydrocarbon group having one or more halogen atoms,
$R^2$ represents an ethyl group,
$R^3$ represents a C1-C6 chain hydrocarbon group optionally having one or more substituents selected from group B, a 5 membered aromatic heterocyclic group selected from group Q (wherein the 5 membered aromatic heterocyclic group may have optionally one or more substituents selected from Group D), a $OR^{12}$, a $NR^{11}R^{12}$, a $NR^{11a}R^{12a}$, a $NR^{24}NR^{11}R^{12}$, or a halogen atom,
q is 0 or 1,
$R^6$ represents a C1-C6 alkyl group optionally having one or more halogen atoms, or a halogen atom, and
p is 0 or 1;

[Embodiment 26] a compound A wherein
$R^1$ represents a C1-C10 chain hydrocarbon group having one or more halogen atoms,
$R^2$ represents and ethyl group,
$R^3$ represents a C1-C6 alkyl group optionally having one or more halogen atoms, or a halogen atom,
q is 0 or 1,
$R^6$ represents a C1-C6 alkyl group optionally having one or more halogen atoms, or a halogen atom, and
p is 0 or 1,

[Embodiment 27] a compound A wherein
$R^1$ represents a C1-C10 chain hydrocarbon group having one or more halogen atoms,
$R^2$ represents an ethyl group, and
p and q are independently of each other 0;

[Embodiment 28] a compound A wherein
$R^1$ represents a C1-C10 fluoroalkyl group having two or more fluoro atoms,
$R^2$ represents an ethyl group,
$R^3$ represent a C1-C6 chain hydrocarbon group optionally having one or more substituents selected from group B, a 5 membered aromatic heterocyclic group selected from group Q (wherein the 5 membered aromatic heterocyclic group may have optionally one or more substituents selected from Group D), a $OR^{12}$, a $NR^{11}R^{12}$, a $NR^{11a}R^{12a}$, a $NR^{24}NR^{11}R^{12}$, or a halogen atom, and
$R^6$ represents a C1-C6 alkyl group optionally having one or more halogen atoms, or a halogen atom;

{Embodiment 29] a compound A wherein $R^1$ represents a C1-C10 fluoroalkyl group having two or more fluoro atoms,
$R^2$ represents an ethyl group,
$R^3$ represents a C1-C6 chain hydrocarbon group optionally having one or more halogen atoms, or a halogen atom, and
$R^6$ represents a C1-C6 alkyl group optionally having one or more halogen atoms, or a halogen atom;

[Embodiment 30] a compound A wherein
$R^1$ represents a C1-C10 fluoroalkyl group having two or more fluoro atoms,
$R^2$ represents an ethyl group,
$R^3$ represents a C1-C6 chain hydrocarbon group optionally having one or more halogen atoms, or a halogen atom,
p is 0 or 1,
$R^6$ represents a C1-C6 alkyl group optionally having one or more halogen atoms, or a halogen. atom, and
p is 0 or 1;

[Embodiment 31] a compound A wherein
$R^1$ represents a C1-C10 fluoroalkyl group having two or more fluoro atoms,
$R^2$ represents an ethyl group,
$R^3$ represents a C1-C6 chain hydrocarbon group optionally having one or more halogen atoms,
q is 0 or 1, and
p is 0;

[Embodiment 32] a compound A wherein
$R^1$ represents a C1-C10 fluoroalkyl group having two or more fluoro atoms,
$R^2$ represents an ethyl group, and
p and q are independently of each other 0;

[Embodiment 33] a compound A wherein
$R^1$ represents a C1-C6 haloalkyl group,
$R^2$ represents a methyl group or an ethyl group,
$R^3$ represents a C1-C6 alkyl group optionally having one or more halogen atoms,
q is 0 or 1,
$R^6$ represents a C1-C6 alkyl group optionally having one or more halogen atoms, or a halogen atom, and
p is 0 or 1;

[Embodiment 34] a compound A wherein
$R^1$ represents a C1-C6 haloalkyl group,
$R^2$ represents an ethyl group,
$R^3$ represents a C1-C6 alkyl group optionally having one or more halogen atoms,
q is 0 or 1,
$R^6$ represents a C1-C6 alkyl group optionally having one or more halogen atoms, or a halogen atom, and
p is 0 or 1;

[Embodiment 35] a compound A wherein
$R^1$ represents a C1-C6 haloalkyl group,
$R^2$ represents an ethyl group, and
p and q are independently of each other 0;

[Embodiment 36] a compound A wherein
$R^1$ represents a C2-C10 alkyl group having two or more fluoro atoms, R² represents an ethyl group,
R³ represents a C1-C6 alkyl group optionally having one or more halogen atoms, or a halogen atom,
q is 0 or 1,
R⁶ represents a C1-C6 alkyl group optionally having one or more halogen atoms, or a halogen atom, and
p is 0 or 1;
[Embodiment 37] a compound A wherein
R¹ represents a C2-C10 alkyl group having two or more fluoro atoms,
R² represents an ethyl group, and
p and p are independently of each other 0;
[Embodiment 38] a compound A wherein
R¹ represents a C1-C10 perfluoroalkyl group,
R² represents an ethyl group,
R³ represents a C1-C6 chain hydrocarbon group optionally having one or more substituents selected from group B, a 5 membered aromatic heterocyclic group selected from group Q (wherein the 5 membered aromatic heterocyclic group may have optionally one or more substituents selected from Group D), a OR¹², a NR¹¹R¹², a NR¹¹ᵃR¹²ᵃ, a NR²⁴NR¹¹R¹², or a halogen atom,
q is 0 or 1,
R⁶ represents a C1-C6 alkyl group optionally having one or more halogen atoms, or a halogen atom, and
p is 0 or 1;
[Embodiment 39] a compound A wherein
R¹ represents a C1-C10 perfluoroalkyl group,
R² represents an ethyl group,
R³ represents a C1C6 alkyl group optionally having one or more halogen atoms, or a halogen atom, and
R⁶ represents a C1-C6 alkyl group optionally having one or more halogen atoms, or a halogen atom;
[Embodiment 40] a compound A wherein
R¹ represents a C1-C20 perfluoroalkyl group,
R² represents an ethyl group,
R³ represents a C1-C6 alkyl group optionally having one or more halogen atoms, or a halogen atom,
q is 0 or 1,
R⁶ represents a C1-C6 alkyl group optionally having one or more halogen atoms, or a halogen atom, and
p is 0 or 1;
[Embodiment 41] a compound A wherein
R¹ represents a C1-C10 perfluoroalkyl group,
R² represents an ethyl group, and
p and q are independently of each other 0;
[Embodiment 42] a compound A wherein
R¹ represents a trifluoromethyl group,
R² represents an ethyl group,
R³ represents a C1-C6 alkyl group optionally having one or more halogen atoms, or a halogen atom, and
R⁶ represents a C1-C6 alkyl group optionally having one or more halogen atoms, or a halogen atom;
[Embodiment 43] a compound A wherein
R¹ represents a trifluoromethyl group,
R² represents an ethyl group, and
p and q are independently of each other 0;
[Embodiment 44] a compound A wherein L represents single bond;
[Embodiment 45] a compound A described in any one of Embodiments 1 to 43 wherein L represents a single bond;
[Embodiment 46] a compound A wherein L represents an oxygen atom and m is 2;
[Embodiment 47] a compound A described in any one Embodiments 1 to 43 wherein L represents an oxygen atom and m is 2;

Embodiments of Compound B include the following compounds.
a compound B wherein $R^{102}$ represents a C1-C3 alkyl group;
a compound B wherein $R^{102}$ represents an ethyl group;
a compound B wherein $R^{106}$, $R^{107}$ and $R^{108}$ and represent independently of each other a hydrogen atom;
a compound B wherein $R^{103}$, $R^{104}$ and $R^{105}$ represent independently of each other a hydrogen atom;
a compound B wherein $R^{103}$ and $R^{105}$ represent independently of each other a hydrogen atom, and $R^{104}$ represents a C1-C6 alkyl group optionally having one or more halogen atoms;
a compound B wherein $R^{103}$ and $R^{105}$ represent independently of each other a hydrogen atom, and $R^{104}$ represents a C1-C6 haloalkyl group;
a compound B wherein $R^{103}$ and $R^{105}$ represent independently of each other a hydrogen atom, and $R^{104}$ represents a trifluoromethyl group;
a compound B wherein $R^{101}$ represents a C2-C10 haloalkyl group, or a (C1-C5 alkoxy) C2-C5 alkyl group;
a compound B wherein $R^{101}$ represents a C2-C10 haloalkyl group, or a (C1-C5 fluoroalkoxy) C2-C5 fluoroalkyl group;
a compound B wherein $R^{101}$ represents a C2-C6 haloalkyl group, or a (C1-C3 haloalkoxy) C2-C4 haloalkyl group;
a compound B wherein $R^{101}$ represents a C2-C6 fluoroalkyl group, or a (C1-C3 fluoroalkoxy) C2-C4 fluoroalkyl group;
compound B wherein $R^{101}$ represents a C2-C10 alkyl group having one or more halogen atoms;
a compound B wherein $R^{101}$ represents a C2-C10 haloalkyl group;
a compound B wherein $R^{101}$ represents a C2-C10 fluoroalkyl group;
a compound B wherein $R^{101}$ represents a C2-C10 haloalkyl group having two or more halogen atoms;
a compound wherein $R^{101}$ represents a C2-C10 fluoroalkyl group having two or more fluoro atoms;
a compound B wherein $R^{101}$ represents C2-C10 fluoroalkyl group, or a (C1-C5 fluoroalkoxy) C2-C5 fluoroalkyl group, $R^{102}$ represents a C1-C6 alkyl group, $R^{104}$ represents a C1-C6 alkyl group optionally having one or more halogen atoms, or a hydrogen atom, and $R^{103}$, $R^{105}$, $R^{106}$, $R^{107}$, and $R^{108}$ represent independently of each other a hydrogen atom;
a compound B wherein $R^{101}$ represents a C2-C10 fluoroalkyl group, or a (C1-C5 fluoroalkoxy) C2-C5 fluoroalkyl group, $R^{102}$ represents a C1-C6 alkyl group, and $R^{103}$, $R^{104}$, $R^{105}$, $R^{106}$, $R^{107}$, and $R^{108}$ represent independently of each other a hydrogen atom;
a compound B wherein $R^{101}$ represents a C2-C6 fluoroalkyl group, or a C1-C3 fluoroalkoxy) C2-C4 fluoroalkyl group, $R^{102}$ represents a C1-C3 alkyl group, $R^{104}$ represents a C1-C3 alkyl group optionally having one or more halogen atoms, or a hydrogen atom, and $R^{103}$, $R^{105}$, $R^{106}$, $R^{107}$, and $R^{108}$ represent independently of each other a hydrogen atom;
a compound B wherein $R^{101}$ represents a C2-C6 fluoroalkyl group, or a (C1-C3 fluoroalkoxy) C2-C4 fluoroalkyl group, $R^{102}$ represents a C1-C3 alkyl group, and $R^{103}$, $R^{104}$, $R^{105}$, $R^{106}$, $R^{107}$, and $R^{108}$ represent independently of each other a hydrogen atom;
a compound B wherein $R^{101}$ represents a C2-C6 fluoroalkyl group, $R^{102}$ represents a C1-C6 alkyl group, and $R^{103}$, $R^{104}$, $R^{105}$, $R^{106}$, $R^{107}$, and $R^{108}$ represent independently of each other a hydrogen atom.

Next, a process for preparing the compound A is explained.

The compound A may be prepared, for example, according to the following processes.

Process 1

In the compound A, a compound represented by formula (A-1b) (hereinafter, referred to as compound (A-1b)), and compound represented by formula -A1c) (hereinafter, referred to as compound (A-1c)) may be prepared by reacting a compound represented by formula (A-1a)) (hereinafter, referred to compound (A-1a)) with an oxidizing agent.

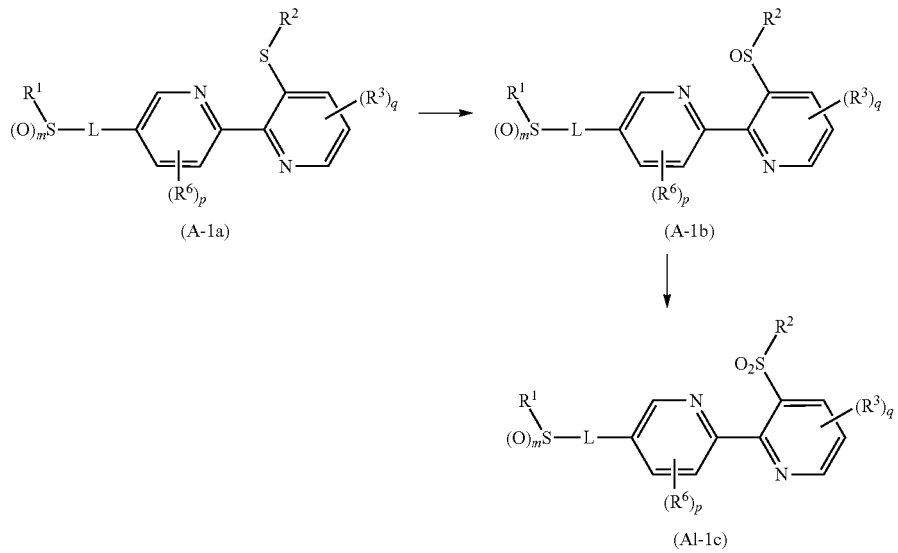

(A-1a)

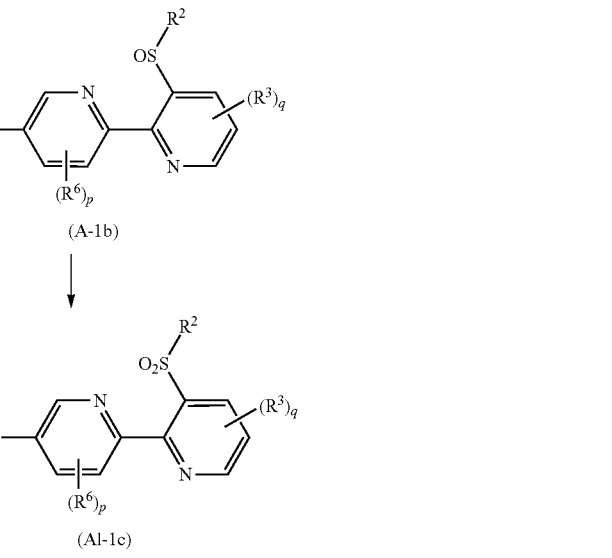

(A-1b)

(Al-1c)

[wherein the symbols are the same as defined above]

First, a process for preparing the compound (A-1b) from the compound (A-1a) is described.

The reaction is usually carried out in a solvent.

Examples of the solvent to be used in the reaction include halogenated aliphatic hydrocarbons such as dichloromethane and chloroform (hereinafter, collectively referred to as halogenated aliphatic hydrocarbons);

nitriles such as acetonitrile (hereinafter collectively referred to nitriles); alcohols such as methanol and ethanol (hereinafter, collectively referred to as alcohols); acetic acid; water; and mixed solvents thereof.

Examples of the oxidizing agent to be used in the reaction includes sodium periodate, m-chloroperoxybenzoic acid (hereinafter referred to as mCPBA), and hydrogen peroxide.

When hydrogen peroxide is used as the oxidizing agent, a base or a catalyst may be added as needed.

Examples of the base to be used in the reaction include sodium carbonate.

Examples of the catalyst to be used in the reaction include tungstic acid, and sodium tungstate.

In the reaction, the oxidizing agent is used usually within a range of 1 to 1.2 molar ratio(s), the base is used usually within a range of 0.01 to 1 molar ratio(s), and the catalyst is used usually within a range of 0.01 to 0.5 molar ratios, as opposed to 1 mole of the compound (A-1a).

The reaction temperature of the reaction is usually within a range of −20 to 80° C. The reaction period of the reaction is usually within a range of 0.1 to 12 hours.

When the reaction is completed, water is added to reaction mixtures, and the reaction mixtures are extracted with organic solvent(s), and the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to give the compound (A-1b).

Next, a process for preparing the compound (A-1c) from the compound (A-1b) is explained.

The reaction is usually carried out in a solvent.

Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and hydrogen peroxide.

When hydrogen peroxide is used as oxidizing agent, a base or a catalyst may be added as needed.

Examples of the base to be used include sodium carbonate.

Examples the catalyst to be used include sodium tungstate.

In the reaction, the oxidizing agent is used usually within a range of 1 to 2 molar ratio(s), the base is used usually within a range of 0.01 to 1 molar ratio(s), and the catalyst is used usually within a range of 0.01 to 0.5 molar ratios, as opposed to 1 mole of the compound (A-1b).

The reaction temperature of the reaction usually within a range of −20 to 120° C. The reaction period of the reaction is usually within a range of 0.1 to 12 hours.

When the reaction is completed, water is added to a reaction mixture, and the reaction mixture is extracted with organic solvent(s), and as needed, the organic layers are washed with an aqueous solution of a reducing agent (such as sodium sulfite, and sodium thiosulfate) and an aqueous solution of a base (such as sodium hydrogen carbonate). The resulting organic layers are dried and/or concentrated to give the compound (A-1c).

Also, the compound (A-1c) may be prepared in one step (one-spot) reacting the compound (A-1a) with an oxidizing agent.

The reaction may be carried out by using the oxidizing agent usually in 2 to 5 molar ratios as opposed to 1 mole of the compound (A-1a) according to a method for preparing the compound (A-1c) from the compound (A-1b).

Process 2

In the compound A, a compound represented by formula (A-1d) (hereinafter, referred to as compound (A-1d)), a compound represented by formula (A-1e) (hereinafter, referred to compound (A-1e)), a compound represented by formula (A-1f) (hereinafter, referred to compound (A-1f)) may be prepared by reacting the compound (A-1c) with an oxidizing agent.

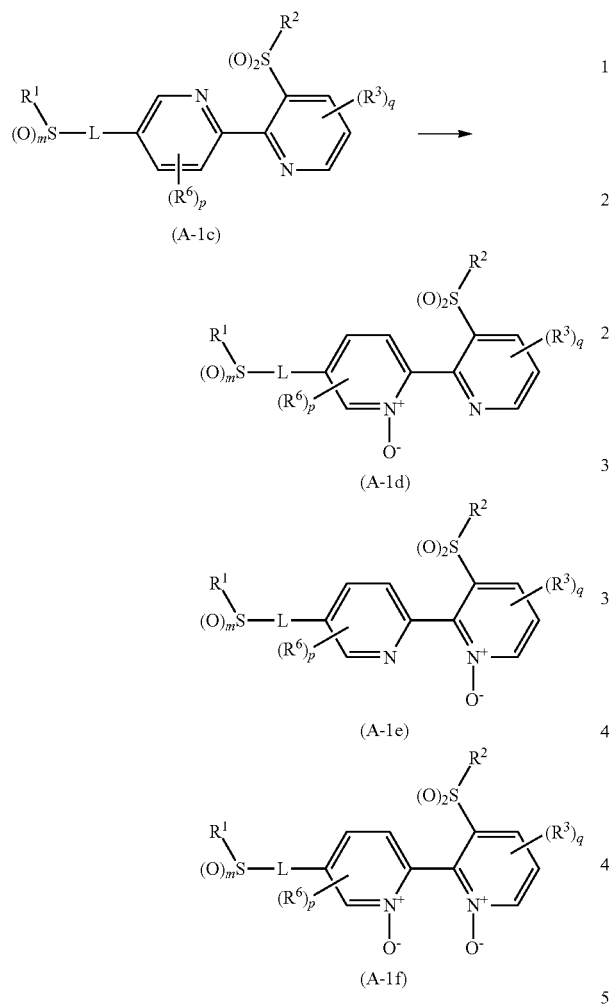

[wherein the symbols are the same as defined above.]

The reaction usually carried out in a solvent.

Examples of the solvent to be used in the reaction include halogenated aliphatic hydrocarbons; nitriles; esters such as ethyl acetate (hereinafter, collectively referred to as esters); alcohols; acetic acid; water; and mixed solvents thereof.

Examples of the oxidizing agent to be used in the reaction include mCPBA and hydrogen peroxide.

When hydrogen peroxide is used as the oxidizing agent, a base or a catalyst may be added as needed.

Examples of the base to be used include sodium carbonate.

Examples of the catalyst to be used include tungstic acid and sodium tungstate.

In the reaction, the oxidizing agent is used usually within a range of 1 to 10 molar ratio(s), the base is used usually within a range of 0.01 to 1 molar ratio(s), and the catalyst is used usually within a range of 0.01 to 0.5 molar ratio(s), as opposed to 1 mole of the compound (A-1c).

The reaction temperature of the reaction is usually within a range of –20 to 80° C. The reaction period of the reaction is usually within a range of 0.1 to 24 hours.

When the reaction is completed, water is added to a reaction mixture, and the reaction mixture is extracted with organic solvent(s), and as needed, the organic layers are washed with an aqueous solution of a reducing agent (such as sodium sulfite, and sodium thiosulfate) and an aqueous solution of a base (such as sodium hydrogen carbonate). The resulting organic layers are dried and/or concentrated to give a mixture of the compound (A-1d), the compound (A-1e) and the compound (A1f).

Process 3

The compound (A-1a) may be prepared by reacting a compound represented formula (M-1) (hereinafter, referred to Compound (M-1)) with a compound represented by formula (R-1) (hereinafter, referred to Compound (R-1)) in the presence of a base.

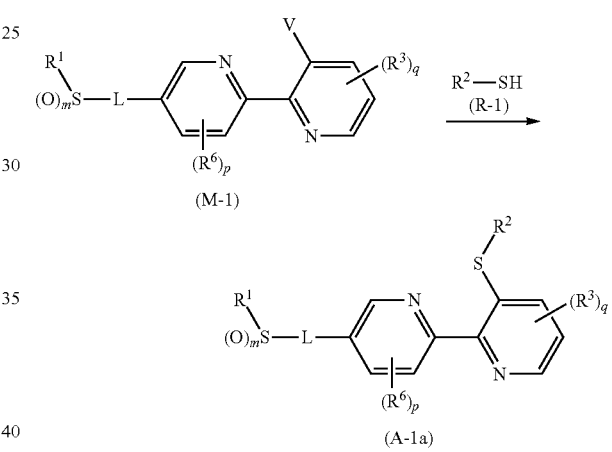

[wherein V represents a halogen atom, and the other symbols are the same as defined above.]

The reaction is usually carried out in a solvent.

Examples of the solvent to be used in the reaction include ethers such as tetrahydrofuran, ethyleneglycol dimethyl ether, methyl tert-butyl ether (hereinafter, referred to as MTBE), and 1,4-dioxane (hereinafter, collectively referred to as ethers); aromatic hydrocarbons such as toluene and xylene (hereinafter, collectively referred to as aromatic hydrocarbons); nitriles; polar aprotic solvents such as dimethylformamide, N-methyl pyrrolidone, dimethyl sulfoxide (hereinafter, referred to DMSO) (hereinafter, collectively referred to as polar aprotic solvent) ; and mixed solvents thereof.

Examples of the base to be used in the reaction include alkali metal carbonates (such as sodium carbonate, and potassium carbonate) (hereinafter, collectively referred to as alkali metal carbonates); and alkali metal hydrides such as sodium hydride (hereinafter, collectively referred to as alkali metal hydrides).

In the reaction, the compound (R-1) is used usually within a range of 1 to 10 molar ratio(s), and the base is used usually within a range of 1 to 10 molar ratio(s), as opposed to 1 mole of the compound (M-1).

The reaction temperature is usually within a range of −20 to 150° C. The reaction period of the reaction is usually within a range of 0.5 to 24 hours.

When the reaction is completed, water is added to reaction mixtures, and the reaction mixtures are extracted with organic solvents, and the resulting organic layers are worked up (for example, drying and concentration) to give the compound (A-1a).

In the reaction, V is preferably a fluorine atom or a chlorine atom.

Process 4

The compound A represented by formula (A-200a) (hereinafter, referred to as Compound (A-200a)) may be prepared by reacting a compound represented by formula (M-2) (hereinafter referred to as Compound (M-2)) with a compound represented by formula (R-2) (hereinafter, referred to as Compound (R-2)) in the presence of a base.

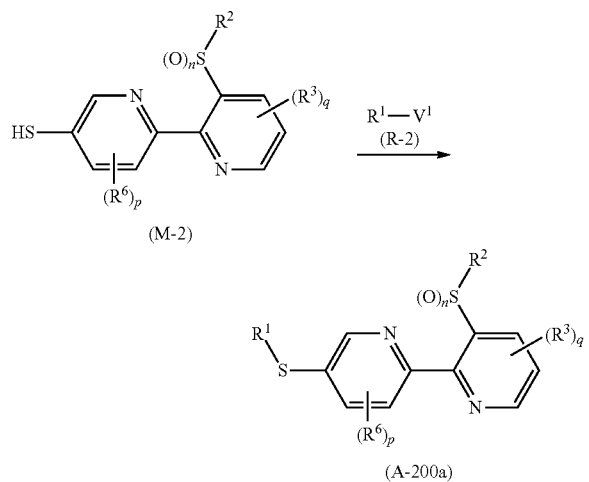

[wherein $V^1$ represents a chlorine atom, a bromine atom, or an iodine atom, and the other symbols are the same as defined above.]

The reaction is usually carried out in a solvent.

Examples of the solvent to be used in the reaction include ethers, halogenated aromatic hydrocarbons, aromatic hydrocarbons, polar aprotic solvent, and mixed solvents thereof.

Examples of the base to be used in the reaction include organic bases such as triethylamine, diisopropylethylamine, pyridine, 4-(dimethylamino)pyridine (hereinafter, collectively referred to as organic bases); alkali metal hydrides; and alkali metal carbonates.

In the reaction, the compound (R-2) is usually used within a range of in 1 to 10 molar ratio(s), and the base is usually used within a range of 0.1 to 5 molar ratio(s), as opposed to 1 mole of the compound (M-2).

The reaction temperature is usually within a range of −20 to 120° C. The reaction period of the reaction is usually within a range of 0.1 to 24 hours.

When the reaction is completed, water is added to reaction mixtures, and the reaction mixtures are extracted with organic solvents, and the resulting organic layers are worked up (for example, drying and concentration) to give the compound (A-200d).

Process 5

The compound (A-200a) may be prepared by reacting a compound represented by formula (M-3) (hereinafter, referred to Compound (M-3)) with a compound (R-2) in the presence of a base and a reducing agent.

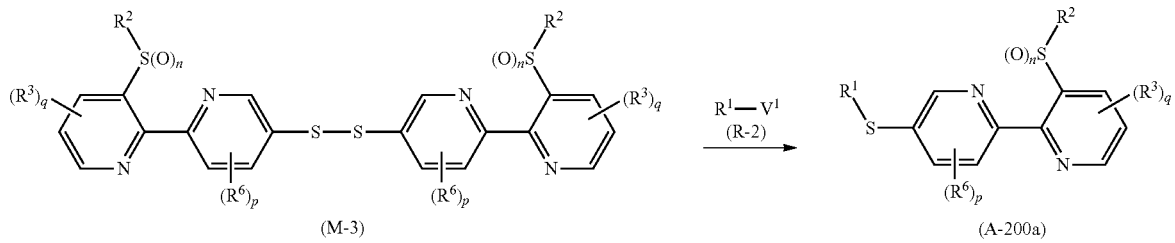

[wherein the symbols are the same as defined above.]

The reaction is usually carried out in a solvent.

Examples of the solvent to be used in the reaction include ethers, aromatic hydrocarbons, nitriles, and polar aprotic solvent.

Examples of the base to be used in the reaction include alkali metal carbonates, and alkali metal hydrides.

Examples of the reducing agent be used in the reaction include hydroxymethanesulfinic acid sodium salt dihydrate.

In the reaction, the compound. (R-2) is usually used within a range of 1 to 10 molar ratio(s), the base is usually used within a range of 1 to 10 molar ratio (s) , and the reducing agent is usually used within. a range of 1 to 10 molar ratio(s), as opposed to 1 mole of the compound. (M-3).

The reaction temperature is usually within a range of −20 to 150° C. The reaction period of the reaction is usually within a range of 0.5 to 24 hours.

When the reaction is completed, water is added to reaction mixtures, and the reaction mixtures are extracted with organic solvents, and the result organic layers are worked up (for example, drying and concentration) to give the compound (A-200a).

Process 6

In the compound A, a compound represented by formula (A-300) (hereinafter, referred to as Compound (A-300)) may be prepared by reacting a compound represented by formula (M-4) (hereinafter, referred to Compound (M-4)) with a compound represented by formula (R-3) (hereinafter, referred to as Compound (R-3)) the presence of a base.

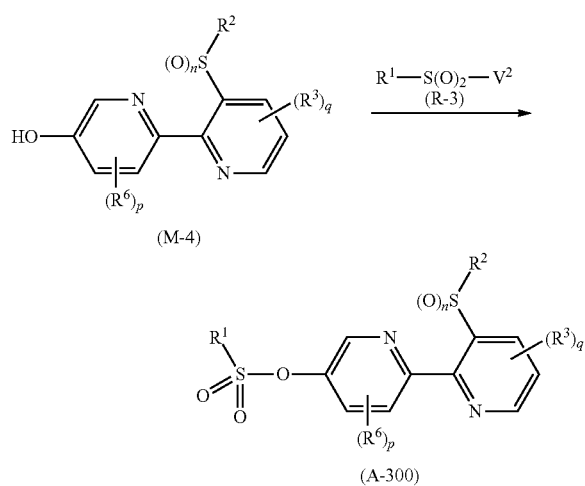

(M-4)

(A-300)

[wherein $V^2$ represents a fluoro atom, a chlorine atom, or a bromine atom, and the symbols are the same as defined above.]

The reaction is usually carried out in a solvent.

Examples of the solvent to be used in the reaction include ethers, aliphatic hydrocarbons, aromatic hydrocarbons, halogenated aliphatic hydrocarbons, nitriles, polar aprotic solvent, nitrogen-containing aromatic compounds, and mixed solvents thereof.

Examples of the base to be used in the reaction include organic bases.

In the reaction, the compound (R-3) is usually used within a range of 1 to 5 molar ratio(s), the base is usually used within a range of 0.1 to 5 molar ratio(s), as opposed to 1 mole of the compound (M-4).

The reaction temperature is usually within a range of 0 to 200° C. The reaction period of the reaction is usually within a range of 0.1 to 24 hours.

When the reaction is completed, water is added to reaction mixtures, and the reaction mixtures are extracted with organic solvents, and the resulting organic layers are worked up (for example, drying and concentration) to isolate the compound (A-300).

Hereinafter, a process for preparing an intermediate compound is described.

Reference Process 1

The compound (M-1) may be prepared by reacting a compound represented by formula (M-5) (hereinafter referred to compound (M-5)) with compound represented by formula (M-6) (hereinafter referred to compound (M-6)) the presence of a catalyst.

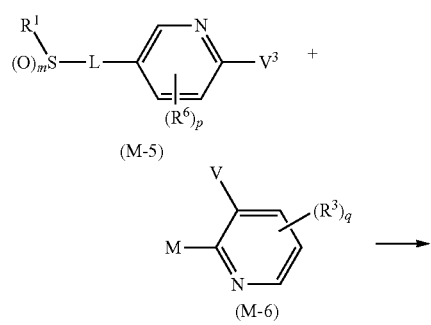

(M-1)

[wherein $V^3$ represents a chlorine atom, a bromine atom or an iodine atom; M represents $Sn(n-C_4H_9)_3$, ZnCl, MgCl, or MgBr; and the other symbols are the same as defined above.]

The compound (M-6) may be a commercially available compound. The compound (M-6) may be prepared according to a similar method to that described in International Publication, 03/024961 or Organic Process Research & Development, 2004, 8, 192-200.

The reaction is usually carried out in a solvent.

Examples of the solvent to be used in the reaction include ethers, aromatic hydrocarbons, polar aprotic solvent, water, and mixed solvents thereof.

Examples of the catalyst to be used in the reaction include palladium catalysts such as tetrakis(triphenylphosphine) palladium(0), 1,1'-bis(diphenylphosphine) ferrocene palladium (II) chloride, tri(dibenzylideneacetone)dipalladium(0), and palladium(II) acetate; nickel catalysts such as bis(cyclooctadiene)nickel(0) and nickel (II) chloride; and copper catalyst such as copper(I) iodide and copper(I) chloride.

A ligand, a base and/or a salt may be added to the reaction as needed.

Examples of the ligand to be used in the reaction include triphenylphosphine, Xantphos, 2,2'-bis(diphenylphosphine)-1,1'-binaphthyl, 1,1'-bis(diphenylphoshino)ferrocene, 2-(dicyclohexylphosphino)-2',4',6'-triisopropyl-1,1'-biphenyl, 2-dicyclohexylphosphino-2',6'-dimethoxybiphenyl, 1,2-bis (diphenylphosphino)ethane, 2,2'-bipyridine, 2-aminoethanol, 8-hydroquinoline, and 1,10-phenanthroline.

Examples of the base to be used in the reaction include alkali metal hydrides, alkali metal carbonates, and organic bases such as triethylamine, diisopropylethylamine, pyridine, and 4-(dimethylamino)pyridine (hereinafter, collectively referred to as organic bases).

Examples of the salts include alkali metal fluorides such as potassium fluoride and sodium fluoride; and alkali metal chlorides such as lithium chloride and sodium chloride.

In the reaction, the compound (M-6) is usually used within a range of 1 to 10 molar ratio(s), the catalyst is usually used within a range of 0.01 to 0.5 molar ratios, the ligand is usually used within a range of 0.01 to 1 molar ratio(s), the base is usually used within a range of 0.1 to 5 molar ratios, and the salt is usually used within a range of 0.1 to 5 molar ratios, as opposed to 1 mole of the compound (M-5).

The reaction temperature is usually within a range of −20 to 200° C. The reaction period of the reaction is usually within a range of 0.1 to 24 hours.

When the reaction is completed, water is added to a reaction mixture, and the reaction mixture is extracted with organic solvent(s), and the organic solvents are worked up (for example, drying and concentration) to give the compound (M-1).

Reference Process 2

In the compound (M-5), a compound represented by formula (M-5b) (hereinafter, referred to as Compound (M-5b)) and a compound represented by formula (M-5c) (hereinafter, referred to as Compound (M-5c)) may be prepared by reacting a compound represented formula (M-5a) (hereinafter, referred to Compound (M-5a)) with an oxidizing agent.

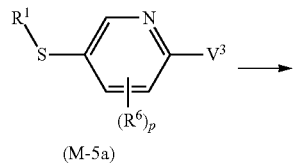

(M-5a)

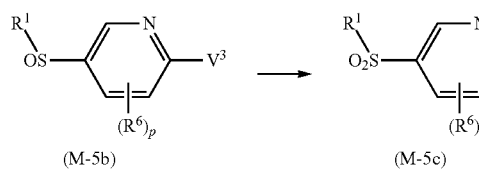

(M-5b)  (M-5c)

[wherein the symbols are the same as defined above.]

The compound (M-5a) may be prepared according to similar method to that described in International Publication 2012/086848.

The above reaction is conducted by using the compound (M-5a) instead of the compound (A-1a) according in a similar method to that described in Process 1 to prepare the compound (M-5b).

Also, the above reaction is conducted by using the compound (M-5b) instead of the compound (A-1b) according to a similar method to that described in Process 1 to prepare the compound (M-5c).

Further, the above reaction is conducted by using the compound (M-5a) instead of the compound (A-1a) according to a similar method to that described in Process 1 to prepare the compound (M-5c) in one step (one-spot).

Reference Process 3

In the compound (M-5), a compound represented by formula (M-5d) (hereinafter, referred to as Compound (M-5d)) may be prepared by reacting a compound represented formula (M-7) (hereinafter, referred to Compound (M-7)) with the compound (R-3) in the presence of a base.

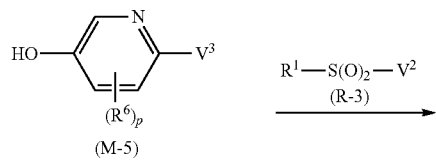

(M-5)

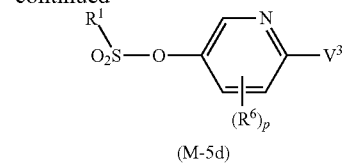

(M-5d)

The above reaction is conducted by using the compound (M-7) instead of the compound (M-4) according to a similar method to that described in Process 6 to prepare the compound (M-5g).

The compound (M-7) may be a commercially available compound, or may be prepared by a known method.

Reference Process 4

The compound (M-5a) may be prepared according to the below-mentioned method.

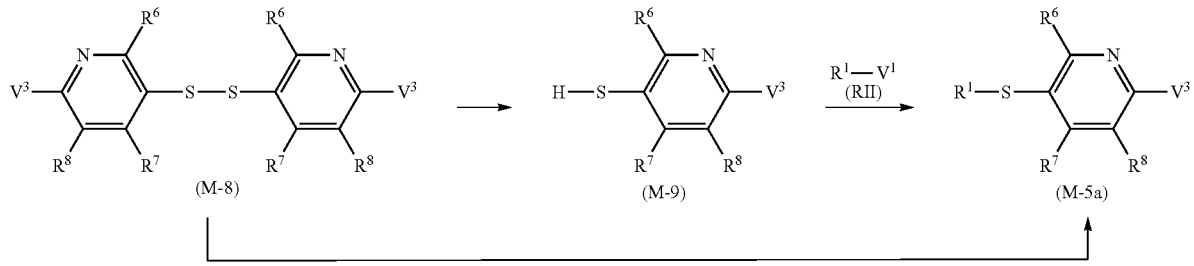

(M-8)  (M-9)  (M-5a)

[wherein the symbols are the same as defined above.]

First, a process for preparing a compound represented by formula (M-9) (hereinafter, referred to as Compound (M-8)) from a compound represented by formula (M-8) (hereinafter, referred to Compound (M-8)) is described.

The compound (M-8) may be prepared according to a similar method to that described in International Publication 2012/086848.

The compound (M-9) may be prepared by reacting the compound (M-8) with a reducing agent.

The reaction is usually carried out in a solvent.

Examples of the solvent to be used in the reaction include aromatic hydrocarbons, nitriles, alcohols, ethers, and mixed solvents thereof.

Examples of the reducing agent to be used in the reaction include borohydrides such as sodium borohydride, and zinc.

When zinc is used as a reducing agent, an acid may be added as needed. Examples of the acid include acetic acid and hydrochloric acid.

When zinc is used as a reducing agent, the acid is usually used within a range of 0.1 to 10 molar ratio(s), and the reducing agent is used within a range of 1 to 10 molar ratio(s), as opposed to 1 mole of the compound (M-8). When sodium borohydride is used as a reducing agent, the reducing agent is used within a range of 1 to 10 molar ratio(s) as opposed to 1 mole of the compound (M-8).

The reaction temperature is usually within a range of −20 to 150° C. The reaction period of the reaction is usually within a range of 0.1 to 24 hours.

When the reaction is completed, water is added to reaction mixtures, and the reaction mixtures are extracted with organic solvent(s), and the organic solvents are worked up (for example, drying and concentration) to give the compound (M-9).

Next, a process for preparing the compound (M-5a) from the compound (M-9) is described.

The compound (M-5a) may be prepared by using the compound (M-9) instead of the compound (M-2) according to a similar method to that described in Process 4.

Also, the compound (M-5a) may be prepared in one step (one-spot) also by using the compound (M-8) instead of the compound (M-3) according to a similar method to that described in Process 5.

Reference Process 5

The compound (M-2) and the compound (M-3) may be prepared according to the below-mentioned method.

Next, a method for preparing the compound (M-3) is described.

The compound (M-3) may be prepared by reacting the compound (M-2) with an oxidizing agent.

The reaction is usually carried out in a solvent.

Examples of the solvent to be used in the reaction include ethers, aromatic hydrocarbons, nitriles, polar aprotic solvent, water, and mixed solvents thereof.

Examples of the oxidizing agent to be used in the reaction include oxygen, aqueous hydrogen peroxide, and potassium ferrocyanide.

A base may be added to the reaction as needed.

Examples of the base to be used in the reaction include alkali metal carbonates, alkali metal hydrides, and alkali metal hydroxides.

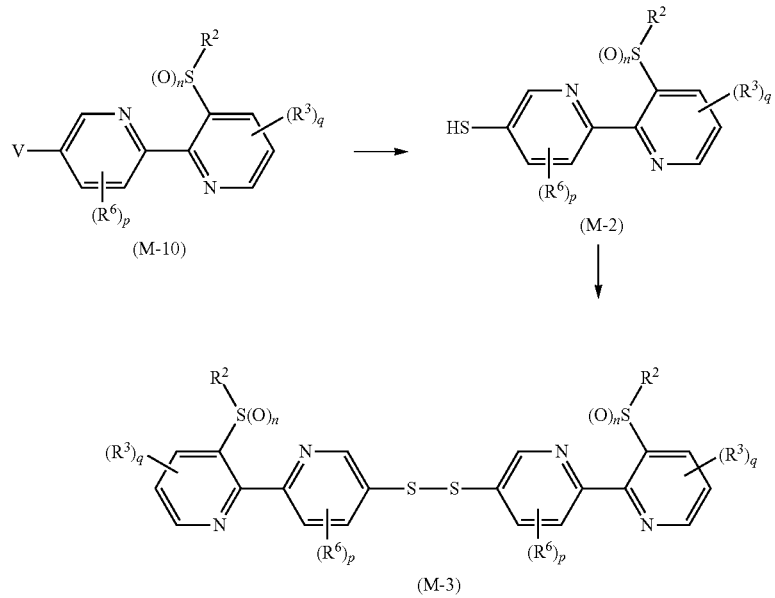

[wherein the symbols are the same as defined above.]

First, a process for preparing the compound (M-2) is described.

The compound (M-2) may be prepared by reacting compound represented by formula (M-10) (hereinafter, referred to as Compound (M-10)) with a sulfating agent.

The reaction is usually carried out in a solvent.

Examples of a solvent to be used in the reaction include ethers, aromatic hydrocarbons, nitriles, polar aprotic solvent, and mixed solvents thereof.

Examples of the sulfating agent include to be used in the reaction include. sodium sulfide and sodium hydrogen sulfide.

In the reaction, the sulfating agent is usually used within a range of 1 to 10 molar ratio(s) as opposed to 1 mole of the compound (M-10).

The reaction temperature is usually within a range of −20 to 150° C. The reaction period of the reaction is usually within a range of 0.5 to 24 hours.

When the reaction is completed, water is added to reaction mixtures, and the reaction mixtures are extracted with organic solvents, and the organic layers are worked up (for example, drying and concentration) to give the compound (M-2).

In the reaction, V is preferably a fluorine atom or a chlorine atom.

In the reaction, the oxidizing agent is usually used within a range of 1 to 100 molar ratio(s), and the base is usually used within a range of 1 to 10 molar ratio(s), as opposed to 1 mole of the compound (M-2). When oxygen is used as the oxidizing agent, oxygen that is present in air may be used as the oxidizing agent.

The reaction temperature is usually within a range of −20 to 150° C. The reaction period of the reaction is usually within a range of 0.5 to 24 hours.

When the reaction is completed, water is added to reaction mixtures, and the reaction mixtures are extracted with organic solvents, and the organic layers are worked up (for example, drying and concentration) to give the compound (M-3).

Reference Process 6

A compound (M-10) wherein V represents a chlorine atom or a bromine atom (hereinafter, referred to Compound (M-10a)) and the compound (M-10) wherein V represents a fluorine atom or an iodine atom (hereinafter, referred to Compound (M-10b)) may be prepared according to the below-mentioned method.

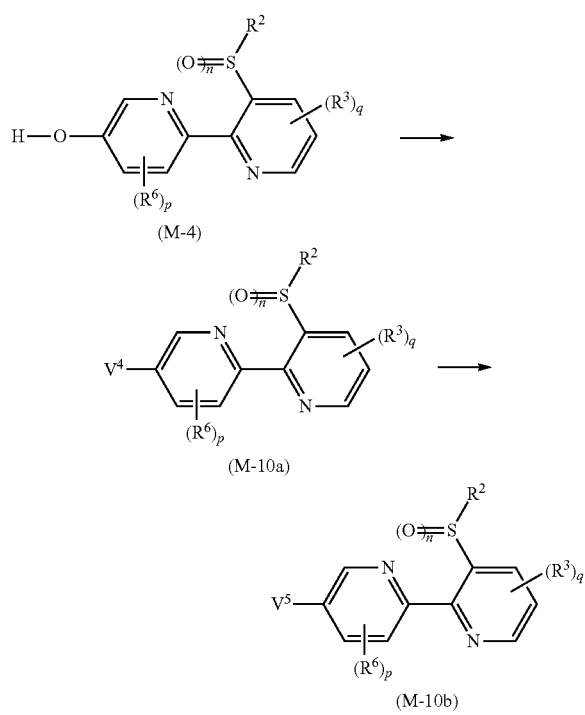

[wherein V⁴ represents chlorine atom or a bromine atom, V⁵ represents a fluorine atom or an iodine atom, and the other symbols are the same as defined above.]

First, a process for preparing the compound (M-10a) from the compound (M-4) is described.

The compound (M-10a) may be prepared by reacting the compound (M-4) with phosphorus oxychloride or phosphorus oxybromide.

The reaction is usually carried out in a solvent.

Examples of the solvent to be used in the reaction include aromatic hydrocarbons.

When phosphorus oxychloride is used, phosphorus oxychloride may be used as a solvent.

In the reaction, phosphorus oxychloride or phosphorus oxybromide is usually used within a range of 1 to 10 molar ratio(s) as opposed to 1 mole of the compound (M-4).

The reaction temperature is usually within a range of 0 to 150° C. The reaction period of the reaction is usually within a range of 0.5 to 24 hours.

When the reaction is completed, water is added to reaction mixtures, and the reaction mixtures are extracted with organic solvents, and the organic layers are worked up (for example, drying and concentration) to give the compound (M-10a).

Next, a process for preparing the compound (M-10b) from the compound (M-10a) is described.

The compound (M10b) may be prepared by reacting the compound (M-10a) with inorganic fluoride or inorganic iodide.

The reaction usually carried out in a solvent.

Examples of the solvent to be used in the reaction include nitriles, polar aprotic solvent, nitrogen-containing aromatic solvents, and mixed solvents thereof.

Examples of the inorganic fluoride compound to be used in the reaction include potassium fluoride, sodium fluoride and cesium fluoride. Examples of the inorganic iodide compound to be used in the reaction include potassium iodide and sodium iodide.

In the reaction, inorganic fluoride fluoride compound or inorganic iodide compound is usually used within a range of 1 to 10 molar ratio(s) as opposed to 1 mole of the compound (M-10a).

The reaction temperature is usually within a range of 0 to 250° C. The reaction period of the reaction is usually within a range of 0.5 to 24 hours.

When the reaction completed, water is added to reaction mixtures, and the reaction mixtures are extracted with organic solvents, and the organic layers are worked up (for example, drying and concentration) to give the compound (M-10b).

Reference Process 7

A compound (M-4) may be prepared by undergoing a dealkylation to a compound represented by formula (M-11) (hereinafter, referred to as Compound (M-11)) in the presence of an acid.

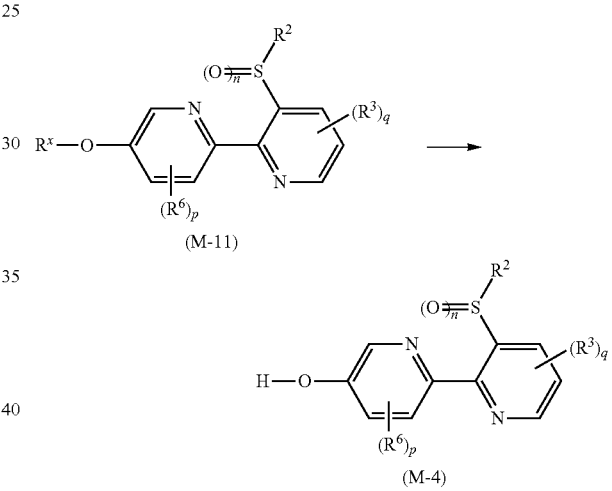

[wherein R$^x$ represents a methyl group or an ethyl group, and the other symbols are the same as defined above.]

The reaction is usually carried out in a solvent.

Examples of the solvent to be used in the reaction include halogenated aliphatic hydrocarbons, aromatic hydrocarbons, nitriles, alcohols, acetic acid, water, and mixed solvents thereof.

Examples of the acid to be used in the reaction include inorganic acids such as hydrochloric acid; boron hydrides such as boron trichloride and boron tribromides and titanium chloride and aluminum chloride.

In the reaction, the acid is usually used within the range of 0.1 to 10 molar ratio as opposed to 1 mole of the compound (M-11). The inorganic acids such as hydrochloric acid is used as an acid in the reaction, the inorganic acids may be used as a solvent.

The reaction temperature is usually within a range of −20 to 150° C. The reaction period of the reaction is usually within a range of 0.1 to 24 hours.

When the reaction is completed, water is added to reaction mixtures, and the reaction mixtures are extracted with organic solvents, and the organic layers are worked up (for example, drying and concentration) to give the compound (M-4).

Reference Process 8

The compound (M-11) wherein n is 0 (hereinafter, referred to as Compound (M-11a)), the compound (M-11) wherein n is 1 (hereinafter, referred to as Compound (M-11b)), and the compound (M-11) wherein n is 2 (hereinafter, referred to as Compound (M-11c)) may be prepared according to a below-mentioned method.

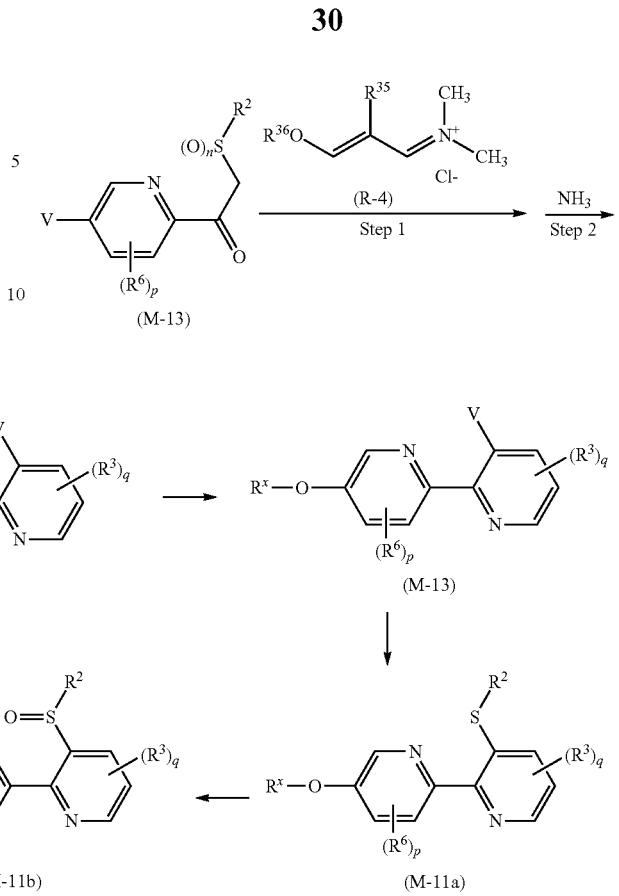

[wherein the symbols are the same as defined above.]

First, a process for preparing a compound represented by formula (M-13) (hereinafter, referred to Compound (M-12)) is described.

The compound (M-13) may be prepared by using a compound represented by formula (M-12) (hereinafter, referred to as Compound (M-12)) instead of the compound (M-5) according to the similar method to that described in Reference Process 1.

The compound (M-12) is a commercially available compound, or may be prepared according to the similar method described in that of Heterocycles, 1990, 30, 875 to 884.

Next, a process for preparing the compound (M-11a) is described.

The compound (M-11a) may be prepared by using the compound (M-13) instead of the compound (M-1) according to a method described in Process 3.

Further, a process for preparing the compound (M-11b) and the compound (M-11c) is described.

The compound (M-11b) and the compound (M-11c) may be prepared by using the compound (M-11a) instead of the compound (A-1a) according to the similar method to that described in Process 1.

Reference Process 9

A compound represented by formula (M-10c) (hereinafter, referred to as Compound (M-10c)) may be prepared by reacting a compound represented by formula (M-13) (hereinafter, referred to as Compound (M-13)) with a compound represented by formula (R-4) (hereinafter, referred to Compound (R-4)) followed by reacting the reaction mixtures with ammonia.

-continued

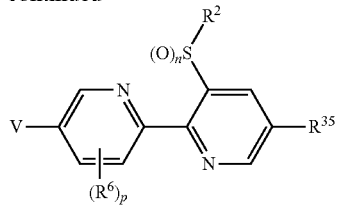

[wherein $R^3$ and $R^{36}$ represent independently of each other a hydrogen atom, a C1-C6 alkyl group optionally having one or more halogen atoms, a phenyl group optionally having one or more substituents selected from group D, or a 5 or 6 membered aromatic heterocyclic Group optionally having one or more substituents selected from group D; and the other symbols are the same as defined above.]

First, Step 1 is described.

The compound (R-4) may be prepared according to the similar method to that described in International Publication No. 2009/054742.

The reaction is usually carried out in a solvent.

Examples of the solvent to be used in the reaction include ethers, aliphatic hydrocarbons, aromatic hydrocarbons, halogenated aliphatic hydrocarbons, alcohols, esters, nitriles, polar aprotic solvent, nitrogen-containing aromatic compounds, and mixed solvents thereof.

In the reaction, the compound (R-4) is usually used within the range of 1 to 10 molar ratio(s) as opposed to 1 mole of the compound (M-13).

The reaction temperature is usually within a range of −50 to 200° C. The reaction period of the reaction is usually within a range of 0.1 to 24 hours.

When the reaction is completed, the reaction mixtures are concentrated to give a residue, which is then used itself to step 2, alternatively water is added to reaction mixtures, and the reaction mixtures are extracted with organic solvents, and the organic layers are worked up (for example, drying and concentration) to give a residue, which is then used to step 2.

Next, Step 2 is described.

The compound (M-10c) may be prepared by reacting the residue obtained step 1 with ammonia.

The reaction is usually carried out in a solvent.

Examples of the solvent to be used in the reaction include ethers, nitriles, alcohols, polar aprotic solvent, nitrogen-containing aromatic compounds, and mixed solvents thereof.

Examples of the ammonia to be used in the reaction include aqueous ammonia solution and ammonia solution in methanol.

In the reaction, ammonia is usually used within the range of 1 to 100 molar ratio(s) as opposed to 1 mole of the compound (M-13).

The reaction temperature is usually within a range of 0 to 100° C. The reaction period of the reaction is usually within a range of 0.1 to 24 hours.

When the reaction is completed, water is added to reaction mixtures, and the reaction mixtures are extracted with organic solvents, and the organic layers are worked up (for example, drying and concentration) to give the compound (M-10c).

Reference Process 10

The compound (M-13) may be prepared by reacting a compound represented by formula (M-14) (hereinafter, referred to as Compound 14) with a compound represented by formula (R-5) (hereinafter, referred to as Compound (R-5)) in the presence of a base.

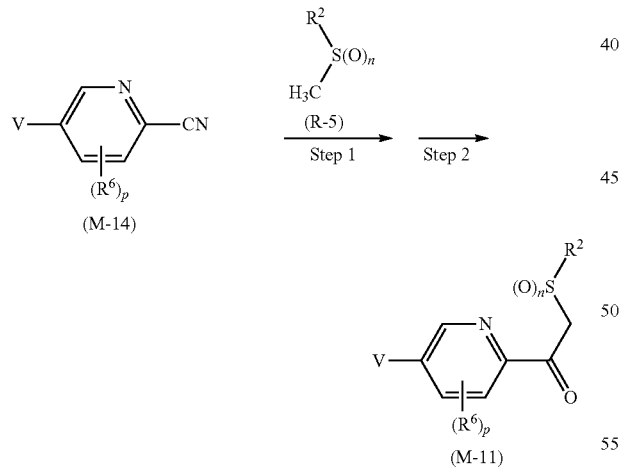

[wherein the symbols are the same as defined above.]

First, Step 1 is described.

The compound (M-14) may be a commercially available compound, or may be prepared by a known method.

The reaction is usually carried out in a solvent.

Examples of the solvent to be used in the reaction include ethers, aromatic hydrocarbons, polar aprotic solvent, and mixed solvents thereof.

Examples of the base to be used in the reaction include n-butyl lithium, s-butyl lithium, t-butyl lithium, lithium diisopropylamide, sodium bis(trimethylsilyl)amide, potassium bis(trimethylsilyl)amide, potassium t-butoxide, and alkali metal hydrides.

In the reaction, the compound (R-5) is usually used within a range of 1 to 5 molar ratio(s), and the base is usually used within a range of 1 to 5 molar ratio(s), as opposed to 1 mole of the compound (M-14).

The reaction temperature is usually within a range of to −78 to 100° C. The reaction period of the reaction is usually within a range of 0.5 to 12 hours.

When the reaction is completed, the reaction mixtures are concentrated to give a residue, which is then used itself to step 2, alternatively water is added to reaction mixtures, and the reaction mixtures are extracted with organic solvents, and the organic layers are worked up (for example, drying and concentration) to give a residue, which is then used to step 2.

Next, Step 2 is described.

The compound (M-11) may be prepared by reacting the residue obtained in step 1 with hydrochloric acid.

The reaction is usually carried out in a solvent.

Examples of the solvent to be used in the reaction include ethers, nitriles, alcohols, polar aprotic solvent, nitrogen-containing aromatic compounds, and mixed solvents thereof.

In the reaction, hydrochloric acid is usually used within the range of 1 to 100 molar ratio(s) as opposed to 1 mole of the compound (M-14).

The reaction temperature usually within a range of 0 to 100° C. The reaction period of the reaction is usually within a range of 0.1 to 24 hours.

When the reaction is completed, water is added to reaction mixtures, and the reaction mixtures are extracted with organic solvents, and the organic layers are worked up (for example, drying and concentration) to give the compound (M-11).

Next, specific examples of the compound A are indicated below.

a compound A represented by formula (200):

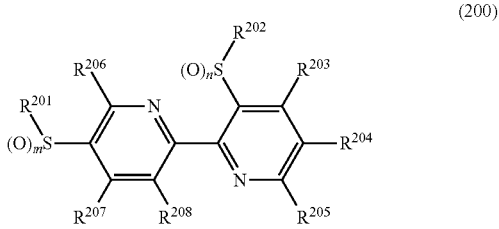

[wherein, $R^{206}$, $R^{207}$, and $R^{208}$ represent independently of each other a hydrogen atom, n is 0, m is 0, and $R^{201}$, $R^{202}$, $R^{203}$, $R^{204}$, and $R^{205}$ represent any combination of the groups indicated in Table 1 to Table 10.];

a compound A represented by formula (200) wherein $R^{206}$, $R^{207}$, and $R^{208}$ represent independently of each other a hydrogen atom, n is 0, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$, $R^{207}$, and $R^{206}$ represent independently of each other a hydrogen atom, n is 0, m is 2, and $R^{201}$, $R^{202}$, $R^{203}$, and $R^{205}$ represent any combination the groups indicated in Table 1 to Table 10;

a compound A represented by formula (200) wherein $R^{206}$, $R^{207}$, and $R^{208}$ represent independently of each other a hydrogen atom, n is 1, m is 0, and $R^{201}$, $R^{202}$, $R^{204}$, and $R^{205}$ represent any combination. of the groups indicated in Table 1 to Table 10;

a compound A represented by formula (200) wherein $R^{206}$, $R^{207}$, and $R^{208}$ represent independently of each other a hydrogen atom, n is 1, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$, $R^{207}$, and $R^{208}$ represent independently of each other a hydrogen atom, n is 1, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$, $R^{207}$, and $R^{208}$ represent independently of each other a hydrogen atom, n is 2, m is 0, and $R^{201}$, $R^{202}$, $R^{203}$, $R^{204}$, and $R^{205}$ represent any combination of the groups indicated in Table 1 to Table 10;

compound A represented by formula (200) wherein $R^{206}$, $R^{207}$, and $R^{208}$ represent independently of each other a hydrogen atom, n is 2, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$, $R^{207}$, and $R^{208}$ represent independently each other a hydrogen atom, n is 2, m is 2, and $R^{201}$, $R^{202}$, $R^{203}$, $R^{204}$, and $R^{205}$ represent any combination the groups indicated in Table 1 to Table 10;

a compound A represented by formula (200) wherein $R^{206}$ represents a chlorine atom, $R^{207}$ and $R^{208}$ represent independently of each other a hydrogen atom, n is 0, m is 0, and $R^{201}$, $R^{202}$, $R^{203}$, and $R^{205}$ represent any combination of the groups indicated in Table 1 to Table 10;

a compound A represented by formula (200) wherein $R^{206}$ represents a chlorine atom, $R^{207}$ and $R^{208}$ represent independently of each other a hydrogen atom, n is 0, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a chlorine atom, $R^{207}$ and $R^{208}$ represent independently of each other a hydrogen atom, n is 0, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a chlorine atom, $R^{207}$ and $R^{208}$ represent independently of each other a hydrogen atom, n is 1, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a chlorine atom, $R^{207}$ and $R^{208}$ represent independently of each other a hydrogen atom, n is 1, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a chlorine atom, $R^{207}$ and $R^{208}$ represent independently of each other a hydrogen atom, n is 1, m is 2, and $R^{201}$, $R^{202}$, $R^{203}$, $R^{204}$, and R205 represent any combination of the groups indicated in Table 1 to Table 10;

a compound A represented by formula (200) wherein $R^{206}$ represents a chlorine atom, and $R^{207}$ and $R^{208}$ represent independently of each other a hydrogen atom, n is 2, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a chlorine atom, $R^{207}$ and $R^{208}$ represent independently of each other a hydrogen atom, n is 2, m is 1, and $R^{201}$, $R^{202}$, $R^{203}$, $R^{204}$ and $R^{205}$ represent any combination of the groups indicated in Table 1 to Table 10;

a compound A represented by formula (200) wherein $R^{206}$ represents chlorine atom, $R^{207}$ and $R^{208}$ represent independently of each other a hydrogen atom, n is 2, m is 2, and $R^{201}$, $R^{202}$, $R^{203}$, $R^{204}$, and $R^{205}$ represent any combination of the groups indicated in Table 1 to Table 10;

a compound A represented by formula (200 wherein $R^{206}$ represents a methyl group, and $R^{207}$ and $R^{208}$ represent independently of each other a hydrogen atom, n is 0, m is 0, and $R^{201}$, $R^{202}$, $R^{203}$, $R^{204}$, and $R^{205}$ represent any combination of the groups indicated in Table 1 to Table 10;

a compound represented by formula (200) wherein $R^{206}$ represents a methyl group, $R^{207}$ and $R^{208}$ represent independently of each other a hydrogen atom, n is 0, m is 1, and $R^{202}$, $R^{202}$, $R^{203}$, $R^{204}$, and $R^{205}$ represent any combination of the groups indicated in Table 1 to Table 10;

compound A represented by formula (200) wherein $R^{206}$ represents a methyl group, $R^{207}$ and $R^{208}$ represents independently of each other a hydrogen atom, n is 0, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a methyl group, $R^{207}$ and $R^{208}$ represent independently of each other a hydrogen atom, n is 1, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a methyl group, and $R^{207}$ represent $R^{208}$ represent independently of each other a hydrogen atom, n is 1, m is 1, and $R^{201}$, $R^{202}$, $R^{203}$, $R^{204}$, and $R^{205}$ represent any combination of the groups indicated in Table 1 to Table 10;

a compound A represented by formula(200) wherein $R^{206}$ represents a methyl group, $R^{207}$ and $R^{208}$ represent independently of each other a hydrogen atom, n is 1, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a methyl group, $R^{207}$ and $R^{208}$ represent independently of each other a hydrogen atom, n is 2, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a methyl group, $R^{207}$ and $R^{208}$ represent independently of each other a hydrogen atom, n is 2, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a methyl group, $R^{207}$ and $R^{208}$ represent independently of each other a hydrogen atom, n is 2, m is 2, and $R^{201}$, $R^{202}$, $R^{203}$, $R^{204}$, and $R^{205}$ represent any combination of the groups indicated in Table 1 to Table 10;

a compound A represented by formula 200) wherein $R^{206}$ represents a trifluoromethyl group, $R^{207}$ and $R^{208}$ represent independently of each other a hydrogen atom, n is 0, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a trifluoromethyl group, $R^{207}$ and $R^{208}$ represent independently of each other a hydrogen atom, n is 0, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a trifluoromethyl group, $R^{207}$ and $R^{208}$ represent independently of each other a hydrogen atom, n is 0, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a trifluoroethyl group, $R^{207}$ and $R^{208}$ represent independently of each other a hydrogen atom, n is 1, m is 0, $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a trifluoromethyl group, $R^{207}$ and $R^{208}$ represent independently of each other a hydrogen atom, n is 1, m is 1, and $R^{201}$, $R^{202}$, $R^{203}$, $R^{204}$, and $R^{205}$, represent any combination of the groups indicated in Table 1 to Table 10;

a compound A represented by formula (200) wherein $R^{206}$ represents a trifluoromethyl group, $R^{207}$ and $R^{208}$ represent independently of each other a hydrogen atom, n is 1, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a trifluoromethyl group, $R^{207}$ and $R^{208}$ represent independently of each other a hydrogen atom, n is 2, m is 0, and $R^{201}$, $R^{202}$, $R^{203}$, $R^{204}$, and $R^{205}$ represent any combination the groups indicated in Table 1 to Table 10;

a compound A represented by formula (200) wherein $R^{206}$ represents a trifluoromethyl group, $R^{207}$ and $R^{208}$ represent independently of each other a hydrogen atom, n is 2, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{206}$ represents a trifluoromethyl group, $R^{207}$ and $R^{208}$ represent independently of each other a hydrogen atom, n is 2, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a chlorine atom, $R^{206}$ and $R^{208}$ represent independently of each other a hydrogen atom, n is 0, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents chlorine atom, $R^{206}$ and $R^{208}$ represent independently of each other a hydrogen atom, n is 0, m is 1, and $R^{201}$, $R^{202}$, $R^{203}$, $R^{204}$, and $R^{205}$ represent any combination of the groups indicated in Table 1 Table 10;

a compound A represented by formula (200) wherein $R^{207}$ represents a chlorine atom, $R^{206}$ and $R^{208}$ represent independently of each other a hydrogen atom, n is 0, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a chlorine atom, and $R^{206}$ and $R^{208}$ represent independently of each other a hydrogen atom, n is 1, m is 0, and $R^{201}$, $R^{202}$, $R^{203}$, $R^{204}$, and $R^{205}$ represent any combination of the groups indicated in Table 1 to Table 10;

a compound A represented formula (200) wherein $R^{207}$ represents a chlorine atom, and $R^{206}$ and $R^{208}$ represent independently of each other a hydrogen atom, n is 1, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents chlorine atom, $R^{206}$ and $R^{208}$ represent independently of each other a hydrogen atom, n is 1, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a chlorine atom, $R^{206}$ and $R^{208}$ represent independently of each other a hydrogen atom, n is 2, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a chlorine atom, and $R^{206}$ and $R^{208}$ represent independently of each other a hydrogen atom, n is 2, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a chlorine atom, $R^{206}$ and $R^{208}$ represent independently of each other a hydrogen atom, n is 2, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a methyl group, and $R^{206}$ and $R^{208}$ represent independently of each other a hydrogen atom, n is 0, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a methyl group, $R^{206}$ and $R^{208}$ represent independently of each other a hydrogen atom, n is 0, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a methyl group, $R^{206}$ and $R^{208}$ represent independently of each other a hydrogen atom, n is 0, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents methyl group, $R^{206}$ and $R^{208}$ represent independently of each other a hydrogen atom, n is 1, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a methyl group, $R^{206}$ and $R^{208}$ represent independently of each other a hydrogen atom, n is 1, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a methyl group, $R^{206}$ and $R^{208}$ represent independently of each other a hydrogen atom, n is 1, m is 2 and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents methyl group, $R^{206}$ and $R^{208}$ represent independently of each other a hydrogen atom, n is 2, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a methyl group, $R^{206}$ and $R^{208}$ represent independently of each other, a hydrogen atom, n is 2, m is 1 and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a methyl group, $R^{206}$ and $R^{208}$ represent independently of each other a hydrogen atom, 2, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a trifluoromethyl group, $R^{206}$ and $R^{208}$ represent independently of each other a hydrogen atom, n is 0, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a trifluoromethyl group, $R^{206}$ and $R^{208}$ represent independently of each other a hydrogen atom, n is 0, to is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a trifluoromethyl group, $R^{206}$ and $R^{208}$ represent independently of each other a hydrogen atom, n is 0, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a trifluoromethyl group, $R^{206}$ and $R^{208}$ represent independently of each other a hydrogen atom, n is 1, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a trifluoromethyl group, $R^{206}$ and $R^{208}$ represent independently of each other a hydrogen atom, n is 0, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a trifluoromethyl group, $R^{206}$ and $R^{208}$ represent independently of each other a hydrogen atom, n is 1, m is 1, and $R^{201}$, $R^{202}$, $R^{203}$, $R^{204}$, and $R^{205}$ represent any combination of the groups indicated in Table 1 to Table 10;

a compound A, represented by formula (200) wherein $R^{207}$ represents a trifluoromethyl group, $R^{206}$ and $R^{208}$ represent independently of each other a hydrogen atom, n is 1, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a trifluoromethyl group, $R^{206}$ and $R^{208}$ represent independently of each other a hydrogen atom, n is 2, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a trifluoromethyl group, $R^{206}$ and $R^{208}$ represent independently of each other a hydrogen atom, n is 2, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{207}$ represents a trifluoromethyl group, $R^{206}$ and $R^{208}$ represent independently of each other a hydrogen atom, n is 2, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a chlorine atom, $R^{206}$ and $R^{207}$ represent independently of each other a hydrogen atom, n is 0, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a chlorine atom, $R^{206}$ and $R^{207}$ represent independently of each other a hydrogen atom, n is 0, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents chlorine atom, $R^{206}$ and $R^{207}$ represent independently of each other a hydrogen atom, n is 0, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a chlorine atom, $R^{206}$ and $R^{207}$ represent independently of each other a hydrogen atom, n is 1, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a chlorine atom, $R^{206}$ and $R^{207}$ represent independently of each other a hydrogen atom, n is 1, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a chlorine atom and $R^{206}$ and $R^{207}$ represent independently of each other a hydrogen atom, n is 1, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a chlorine atom, and $R^{206}$ and $R^{207}$ represent independently of each other a hydrogen atom, n is 2, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a chlorine atom, $R^{206}$ and $R^{207}$ represent independently of each other a hydrogen atom, n is 2, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a chlorine atom, $R^{206}$ and $R^{207}$ represent independently of each other a hydrogen atom, n is 2, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a methyl group, and $R^{206}$ and $R^{207}$ represent independently of each other a hydrogen atom, n is 0, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a methyl group, $R^{206}$ and $R^{207}$ represent independently of each other a hydrogen atom, n is 0, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents methyl group, $R^{206}$ and $R^{207}$ represent independently of each other a hydrogen atom, n is 0, is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a methyl group, $R^{206}$ and $R^{207}$ represent independently of each other a hydrogen atom, n is 0, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a methyl group, $R^{206}$ and $R^{207}$ represent independently of each other a hydrogen atom, n is 1, m is 0, and $R^{201}$, $R^{202}$, $R^{203}$, $R^{204}$, and $R^{205}$ represent any combination of the groups indicated in Table 1Table 10;

a compound A represented by formula (200) wherein $R^{208}$ represents a methyl group, $R^{206}$ and $R^{207}$ represent independently of each other a hydrogen atom, n is 1, m is 1, and $R^{201}$, $R^{202}$, $R^{203}$, $R^{4}$, and $R^{205}$ represent any combination of the groups indicated in Table 1 to Table 10;

a compound A represented by formula (200) wherein $R^{208}$ represents a methyl group, $R^{206}$ and $R^{207}$ represent independently of each other a hydrogen atom, n is 1, m 2, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a methyl group, and $R^{206}$ and $R^{207}$ represent independently of each other a hydrogen atom, is 2, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a methyl group, $R^{206}$ and $R^{207}$ represent independently of each other a hydrogen atom, n is 2, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a methyl group, and $R^{206}$ and $R^{207}$ represent independently of each other a hydrogen atom, n is 2, in is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a trifluoromethyl group, $R^{206}$ and $R^{207}$ represent independently of each other a hydrogen atom, n is 0, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a trifluoromethyl group, $R^{206}$ and $R^{207}$ represent independently of each other a hydrogen atom, n is 0, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a trifluoromethyl group, $R^{206}$ and $R^{207}$ represent independently of each other a hydrogen atom, n is 0, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a trifluoromethyl group, $R^{206}$ and $R^{207}$ represent independently of each other a hydrogen atom, n is 1, m is 0, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a trifluoromethyl group, $R^{206}$ and $R^{207}$ represent independently of each other a hydrogen atom, n is 1, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a trifluoromethyl group, $R^{206}$ and $R^{207}$ represent independently of each other a hydrogen atom, n is 1, m is 2, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a trifluoromethyl group, $R^{206}$ and $R^{207}$ represent independently of each other a hydrogen atom, n is 2, m is 0, and $R^{201}$, $R^{202}$, $R^{203}$, $R^{204}$, and $R^{205}$ represent any combination of the groups indicated in Table 1 to 10;

a compound A represented by formula (200) wherein $R^{208}$ represents a trifluoromethyl group, $R^{206}$ and $R^{207}$ represent independently of each other a hydrogen atom, n is 2, m is 1, and $R^{201}$, $R^{202}$, $R^{203}$, $R^{204}$, and $R^{205}$ represent any combination of the groups indicated in Table 1 to Table 10;

a compound A represented by formula (200) wherein $R^{208}$ represents a trifluoromethyl group, $R^{206}$ and $R^{207}$ represent independently of each other a hydrogen atom, n is 2, m is 2, and $R^{201}$, $R^{202}$, $R^{203}$, $R^{204}$, and $R^{205}$ represent any combination of the groups indicated in Table 1 to Table 10.

TABLE 1

| $R^{201}$ | $R^{202}$ | $R^{203}$ | $R^{204}$ | $R^{205}$ |
|---|---|---|---|---|
| $CF_2HCH_2$ | $CH_3CH_2$ | H | H | H |
| $CF_3CH_2$ | $CH_3CH_2$ | H | H | H |
| $CF_3CF_2$ | $CH_3CH_2$ | H | H | H |
| $CF_2HCF_2$ | $CH_3CH_2$ | H | H | H |
| $CClFHCF_2$ | $CH_3CH_2$ | H | H | H |
| $CF_2CH_2CH_2$ | $CH_3CH_2$ | H | H | H |
| $CF_2HCF_2CH_2$ | $CH_3CH_2$ | H | H | H |
| $CF_3CF_2CH_2$ | $CH_3CH_2$ | H | H | H |
| $CF_3CF_2CF_2$ | $CH_3CH_2$ | H | H | H |
| $CF_3CFHCF_2$ | $CH_3CH_2$ | H | H | H |
| $(CF_3)_2CF$ | $CH_3CH_2$ | H | H | H |
| $(CF_3)_3C(CH_3)CH_3$ | $CH_3CH_2$ | H | H | H |
| $CF_3CFHCF_2CH_2$ | $CH_3CH_2$ | H | H | H |
| $CF_3(CF_2)_2CH_2$ | $CH_3CH_2$ | H | H | H |
| $CF_3(CF_2)_2CF_2$ | $CH_3CH_2$ | H | H | H |
| $CF_3(CF_2)_3CH_2$ | $CH_3CH_2$ | H | H | H |
| $CF_3(CF_2)_4CH_2$ | $CH_3CH_2$ | H | H | H |
| $CF_3(CF_2)_4CF_2$ | $CH_3CH_2$ | H | H | H |

TABLE 2

| $R^1$ | $R^{202}$ | $R^{203}$ | $R^{204}$ | $R^{205}$ |
|---|---|---|---|---|
| $CF_3(CF_2)_3CH_2CH_2$ | $CH_3CH_2$ | H | H | H |
| $(CF_3)_2CF(CF_2)_2CH_2CH_2$ | $CH_3CH_2$ | H | H | H |
| $CF_2H(CF_2)_3CH_2$ | $CH_3CH_2$ | H | H | H |
| $CF_2H(CF_2)_5CH_2$ | $CH_3CH_2$ | H | H | H |
| $CF_3OCFHCF_3$ | $CH_3CH_2$ | H | H | H |
| $CF_3CF_2OCFHCF_2$ | $CH_3CH_2$ | H | H | H |
| $CF_3(CF_2)_2OCFHCF_2$ | $CH_3CH_2$ | H | H | H |
| $CF_3CH_2OCH_2CH_2$ | $CH_3CH_2$ | H | H | H |

TABLE 3

| $R^{201}$ | $R^{202}$ | $R^{203}$ | $R^{204}$ | $R^{205}$ |
|---|---|---|---|---|
| $CF_2H$ | $CH_3CH_2$ | H | H | H |
| $CF_3$ | $CH_3CH_2$ | H | H | H |
| $CCl_3$ | $CH_3CH_2$ | H | H | H |
| $CH_3CF_2$ | $CH_3CH_2$ | H | H | H |
| $CCl_3CH_2$ | $CH_3CH_2$ | H | H | H |
| $CBrF_2CF_2$ | $CH_3CH_2$ | H | H | H |
| $CH_3CF_2CH_2$ | $CH_3CH_2$ | H | H | H |
| $CF_3CH(CH_3)$ | $CH_3CH_2$ | H | H | H |
| $CF_3C(CH_3)$ | $CH_3CH_2$ | H | H | H |
| $CH(CH_2)_2CH(CF_3)$ | $CH_3CH_2$ | H | H | H |
| $(CF_3)_2CH$ | $CH_3CH_2$ | H | H | H |
| $CH_3CH_2CH(CF_3)$ | $CH_3CH_2$ | H | H | H |
| $CF_3CCl_3CH_2$ | $CH_3CH_2$ | H | H | H |
| $CF_3CF_2CH(CH_3)$ | $CH_3CH_2$ | H | H | H |
| $CF_3CF_3CH(CH_2CH_3)$ | $CH_3CH_2$ | H | H | H |
| $C(CH_3)(CF_3)_2CH_2$ | $CH_3CH_2$ | H | H | H |
| $CF_2(CF_2)_3CF_2$ | $CH_3CH_2$ | H | H | H |
| $CBrF_2CF_3CH_2CH_2$ | $CH_3CH_2$ | H | H | H |
| $CF_3CFHCF_2CH(CH_3)$ | $CH_3CH_2$ | H | H | H |
| $CF_3CF=CH$ | $CH_3CH_2$ | H | H | H |
| $CF_3CF=CF$ | $CH_3CH_2$ | H | H | H |

TABLE 4

| $R^{201}$ | $R^{202}$ | $R^{203}$ | $R^{204}$ | $R^{205}$ |
|---|---|---|---|---|
| $CF_3(CF_2)_3CH_2CH_2CH_2$ | $CH_3CH_2$ | H | H | H |
| $CF_3(CF_2)_3CF_2$ | $CH_3CH_2$ | H | H | H |
| $CF_3CF_2(CH_2)_5CH_2$ | $CH_3CH_2$ | H | H | H |
| $CF_2(CF_2)_5CH_2CH_2CH_2$ | $CH_3CH_2$ | H | H | H |
| $CF_3(CF_2)_3CH_2(CH_2)_4CH_2$ | $CH_3CH_2$ | H | H | H |
| $CF_3(CF_2)_5CH_2CH_2$ | $CH_3CH_2$ | H | H | H |

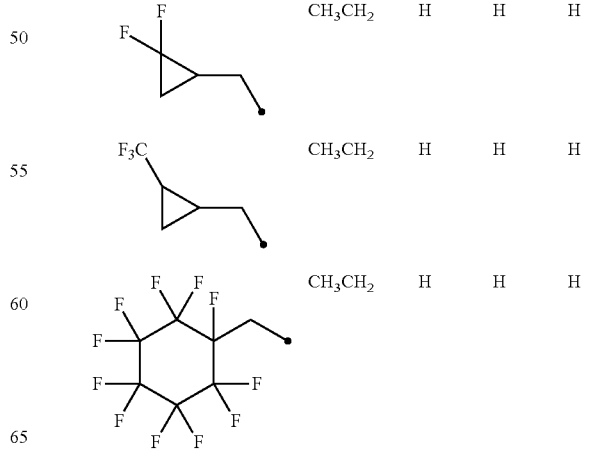

TABLE 4-continued

| $R^{201}$ | $R^{202}$ | $R^{203}$ | $R^{204}$ | $R^{205}$ |
|---|---|---|---|---|
| (2,2,3,3-tetrafluorocyclobutyl)methyl | $CH_3CH_2$ | H | H | H |
| (4,4-difluorocyclohexyl) | $CH_3CH_2$ | H | H | H |
| (4-trifluoromethylcyclohexyl) | $CH_3CH_2$ | H | H | H |
| (3-trifluoromethylcyclohexyl) | $CH_3CH_2$ | H | H | H |

TABLE 5

| $R^{201}$ | $R^{202}$ | $R^{203}$ | $R^{204}$ | $R^{205}$ |
|---|---|---|---|---|
| $CH_3SCH_2CF_2CH_2$ | $CH_3CH_2$ | H | H | H |
| $CH_3S(O)CH_2CF_2CH_2$ | $CH_3CH_2$ | H | H | H |
| $CH_3S(O)_2CH_2CF_2CH_2$ | $CH_3CH_2$ | H | H | H |
| $CF_3CH_2SCH_2CF_2CH_2$ | $CH_3CH_2$ | H | H | H |
| $CF_3CH_2S(O)CH_2CF_2CH_2$ | $CH_3CH_2$ | H | H | H |
| $CF_3CH_2S(O)_2CH_2CF_2CH_2$ | $CH_3CH_2$ | H | H | H |
| $CF_3SCH_2CF_2CH_2$ | $CH_3CH_2$ | H | H | H |
| $CF_3S(O)CH_2CF_2CH_2$ | $CH_3CH_2$ | H | H | H |
| $CF_3S(O)_2CH_2CF_2CH_2$ | $CH_3CH_2$ | H | H | H |
| $CF_3SCH_2(CF_2)_2CH_2$ | $CH_3CH_2$ | H | H | H |
| $CF_3S(O)CH_2(CF_2)_2CH_2$ | $CH_3CH_2$ | H | H | H |
| $CF_3S(O)_2CH_2(CF_2)_2CH_2$ | $CH_3CH_2$ | H | H | H |
| $CF_3SCH_2(CF_2)_3CH_2$ | $CH_3CH_2$ | H | H | H |
| $CF_3S(O)CH_2(CF_2)_3CH_2$ | $CH_3CH_2$ | H | H | H |
| $CF_3S(O)_2CH_2(CF_2)_3CH_2$ | $CH_3CH_2$ | H | H | H |
| $CF_3SCH_2(CF_2)_4CH_2$ | $CH_3CH_2$ | H | H | H |
| $CF_3S(O)CH_2(CF_2)_4CH_2$ | $CH_3CH_2$ | H | H | H |
| $CF_3S(O)_2CH_2(CF_2)_4CH_2$ | $CH_3CH_2$ | H | H | H |
| $CF_3CH_2SCH_2CH_2$ | $CH_3CH_2$ | H | H | H |
| $CF_3CH_2S(O)CH_2CH_2$ | $CH_3CH_2$ | H | H | H |
| $CF_3CH_2S(O)_2CH_2CH_2$ | $CH_3CH_2$ | H | H | H |
| $CF_3SCH_2CH_2$ | $CH_3CH_2$ | H | H | H |
| $CF_3S(O)CH_2CH_2$ | $CH_3CH_2$ | H | H | H |
| $CF_3S(O)_2CH_2CH_2$ | $CH_3CH_2$ | H | H | H |

TABLE 6

| $R^{201}$ | $R^{202}$ | $R^{203}$ | $R^{204}$ | $R^{205}$ |
|---|---|---|---|---|
| $CF_2HCH_2$ | $CH_3$ | H | H | H |
| $CF_3CH_2$ | $CH_3$ | H | H | H |
| $CF_3CF_2$ | $CH_3$ | H | H | H |
| $CF_2HCF_2$ | $CH_3$ | H | H | H |
| $CClFHCF_2$ | $CH_3$ | H | H | H |
| $CF_3CH_3CH_2$ | $CH_3$ | H | H | H |
| $CF_2HCF_2CH_2$ | $CH_3$ | H | H | H |
| $CF_3CF_2CH_2$ | $CH_3$ | H | H | H |
| $CF_3CF_2CF_2$ | $CH_3$ | H | H | H |
| $CF_2CFHCF_2$ | $CH_3$ | H | H | H |
| $(CF_3)_2CF$ | $CH_3$ | H | H | H |
| $(CF_3)_2C(CH_3)CH_2$ | $CH_3$ | H | H | H |
| $CF_3CFHCF_2CH_2$ | $CH_3$ | H | H | H |
| $CF_3(CF_2)_2CH_2$ | $CH_3$ | H | H | H |

TABLE 6-continued

| $R^{201}$ | $R^{202}$ | $R^{203}$ | $R^{204}$ | $R^{205}$ |
|---|---|---|---|---|
| $CF_3(CF_2)_2CF_2$ | $CH_3$ | H | H | H |
| $CF_3(CF_2)_3CH_2$ | $CH_3$ | H | H | H |
| $CF_3(CF_2)_4CH_2$ | $CH_3$ | H | H | H |
| $CF_3(CF_2)_4CF_2$ | $CH_3$ | H | H | H |

TABLE 7

| $R^{201}$ | $R^{202}$ | $R^{203}$ | $R^{204}$ | $R^{205}$ |
|---|---|---|---|---|
| $CF_3(CF_2)_3CH_2CH_2$ | $CH_3$ | H | H | H |
| $(CF_3)_2CF(CF_2)_2CH_2CH_2$ | $CH_3$ | H | H | H |
| $CF_2H(CF_2)_3CH_2$ | $CH_3$ | H | H | H |
| $CF_2H(CF_2)_5CH_2$ | $CH_3$ | H | H | H |
| $CF_2OCFHCF_2$ | $CH_3$ | H | H | H |
| $CF_3CF_2OCFHCF_2$ | $CH_3$ | H | H | H |
| $CF_3(CF_3)_2OCFHCF_2$ | $CH_3$ | H | H | H |
| $CF_3CH_2OCH_2CH_2$ | $CH_3$ | H | H | H |

TABLE 8

| $R^{201}$ | $R^{202}$ | $R^{203}$ | $R^{204}$ | $R^{205}$ |
|---|---|---|---|---|
| $CF_2H$ | $CH_3$ | H | H | H |
| $CF_3$ | $CH_3$ | H | H | H |
| $CCl_3$ | $CH_3$ | H | H | H |
| $CH_3CF_2$ | $CH_3$ | H | H | H |
| $CCl_3CH_2$ | $CH_3$ | H | H | H |
| $CBrF_2CF_2$ | $CH_3$ | H | H | H |
| $CH_3CF_2CH_2$ | $CH_3$ | H | H | H |
| $CF_3CH(CH_3)$ | $CH_3$ | H | H | H |
| $CF_3C(CH_3)_3$ | $CH_3$ | H | H | H |
| $CH(CH_3)_2CH(CF_3)$ | $CH_3$ | H | H | H |
| $(CF_3)_2CH$ | $CH_3$ | H | H | H |
| $CH_3CH_2CH(CF_3)$ | $CH_3$ | H | H | H |
| $CF_3CCl_2CH_2$ | $CH_3$ | H | H | H |
| $CF_3CF_2CH(CH_3)$ | $CH_3$ | H | H. | H |
| $CF_3CF_2CH(CH_2CH_3)$ | $CH_3$ | H | H | H |
| $C(CH_3)(CF_3)_2CH_2$ | $CH_3$ | H | H | H |
| $CF_3(CF_2)_3CF_2$ | $CH_3$ | H | H | H |
| $CBrF_2CF_2CH_2CH_2$ | $CH_3$ | H | H | H |
| $CF_3CFHCF_2CH(CH_3)$ | $CH_3$ | H | H | H |
| $CF_3CF=CH$ | $CH_3$ | H | H | H |
| $CF_3CF=CF$ | $CH_3$ | H | H | H |

TABLE 9

| $R^{201}$ | $R^{202}$ | $R^{203}$ | $R^{204}$ | $R^{205}$ |
|---|---|---|---|---|
| $CF_3(CF_2)_3CH_2CH_2CH_2$ | $CH_3$ | H | H | H |
| $CF_3(CF_2)_5CF_2$ | $CH_3$ | H | H | H |
| $CF_3CF_2(CH_2)_5CH_2$ | $CH_3$ | H | H | H |
| $CF_3(CF_2)_5CH_2CH_2$ | $CH_3$ | H | H | H |
| $CF_3(CF_2)_3CH_2(CH_2)_4CH_2$ | $CH_3$ | H | H | H |
| $CF_3(CF_2)_5CH_2CH_2$ | $CH_3$ | H | H | H |

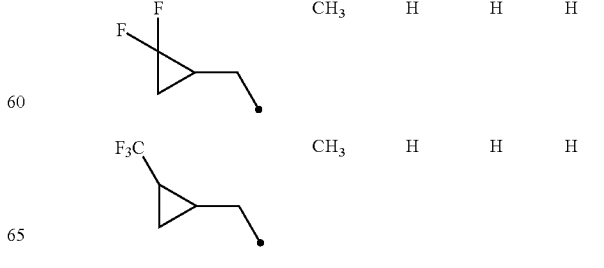

TABLE 9-continued

| R²⁰¹ | R²⁰² | R²⁰³ | R²⁰⁴ | R²⁰⁵ |
|---|---|---|---|---|
| (perfluorocyclohexyl-CH₂-) | CH₃ | H | H | H |
| (tetrafluorocyclobutyl-CH₂-) | CH₃ | H | H | H |
| (4,4-difluorocyclohexyl-) | CH₃ | H | H | H |
| (4-trifluoromethylcyclohexyl-) | CH₃ | H | H | H |
| (3-trifluoromethylcyclohexyl-) | CH₃ | H | H | H |

TABLE 10

| R²⁰¹ | R²⁰² | R²⁰³ | R²⁰⁴ | R²⁰⁵ |
|---|---|---|---|---|
| CH₃SCH₂CF₂CH₂ | CH₃ | H | H | H |
| CH₃S(O)CH₂CF₂CH₂ | CH₃ | H | H | H |
| CH₃S(O)₂CH₂CF₂CH₂ | CH₃ | H | H | H |
| CF₃CH₂SCH₂CF₂CH₂ | CH₃ | H | H | H |
| CF₃CH₂S(O)CH₂CF₂CH₂ | CH₃ | H | H | H |
| CF₃CH₂S(O)₂CH₂CF₂CH₂ | CH₃ | H | H | H |
| CF₃SCH₂CF₂CH₂ | CH₃ | H | H | H |
| CF₃S(O)CH₂CF₂CH₂ | CH₃ | H | H | H |
| CF₃S(O)₂CH₂CF₂CH₂ | CH₃ | H | H | H |
| CF₃SCH₂(CF₂)₂CH₂ | CH₃ | H | H | H |
| CF₃S(O)CH₂(CF₂)₂CH₂ | CH₃ | H | H | H |
| CF₃S(O)₂CH₂(CF₂)₂CH₂ | CH₃ | H | H | H |
| CF₃SCH₂(CF₂)₃CH₂ | CH₃ | H | H | H |
| CF₃S(O)CH₂(CF₂)₃CH₂ | CH₃ | H | H | H |
| CF₃S(O)₂CH₂(CF₂)₃CH₂ | CH₃ | H | H | H |
| CF₃SCH₂(CF₂)₄CH₂ | CH₃ | H | H | H |
| CF₃S(O)CH₂(CF₂)₄CH₂ | CH₃ | H | H | H |
| CF₃S(O)₂CH₂(CF₂)₄CH₂ | CH₃ | H | H | H |
| CF₃CH₂SCH₂CH₂ | CH₃ | H | H | H |
| CF₃CH₂S(O)CH₂CH₂ | CH₃ | H | H | H |
| CF₃CH₂S(O)₂CH₂CH₂ | CH₃ | H | H | H |
| CF₃SCH₂CH₂ | CH₃ | H | H | H |
| CF₃S(O)CH2CH₂ | CH₃ | H | H | H |
| CF₃S(O)₂CH₂CH₂ | CH₃ | H | H | H | a compound A represented by formula (200) wherein n is 2, $R^{201}$ represents a 2,2,3,3-tetrafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

TABLE 11

| R²⁰³ | R²⁰⁴ | R²⁰⁵ | R²⁰⁶ | R²⁰⁷ | R²⁰⁸ |
|---|---|---|---|---|---|
| H | CH₂=CHCH₂ | H | H | H | H |
| CH₃O | H | H | H | H | H |
| H | CH₃O | H | H | H | H |
| H | H | CH₃O | H | H | H |
| H | CF₃O | H | H | H | H |
| H | CF₃S | H | H | H | H |
| H | CF₃S(O) | H | H | H | H |
| H | CF₃S(O)₂ | H | H | H | H |
| Cl | H | H | H | H | H |
| H | Cl | H | H | H | H |
| H | H | Cl | H | H | H |
| CF₃ | H | H | H | H | H |
| CF₃CF₂ | H | H | H | H | H |
| CF₃CF₂CF₂ | H | H | H | H | H |
| (CF₃)₂CF | H | H | H | H | H |
| H | CF₃ | H | H | H | H |
| H | CF₃CF₂ | H | H | H | H |
| H | CF₃CF₂CF₂ | H | H | H | H |
| H | (CF₃)₂CF | H | H | H | H |
| H | H | CF₃ | H | H | H |
| H | H | CF₃CF₂ | H | H | H |
| H | H | CF₃CF₂CF₂ | H | H | H |
| H | H | (CF₃)₂CF | H | H | H |

TABLE 12

| R²⁰³ | R²⁰⁴ | R²⁰⁵ | R²⁰⁶ | R²⁰⁷ | R²⁰⁸ |
|---|---|---|---|---|---|
| NH₂ | H | H | H | H | H |
| CH₂NH | H | H | H | H | H |
| (CH₃)₂N | H | H | H | H | H |
| CF₃CH₂NH | H | H | H | H | H |
| H | NH₂ | H | H | H | H |
| H | CH₃NH | H | H | H | H |
| H | (CH₃)₂N | H | H | H | H |
| H | CF₃CH₂NH | H | H | H | H |
| H | H | NH₂ | H | H | H |
| H | H | CH₃NH | H | H | H |
| H | H | (CH₃)₂N | H | H | H |
| H | H | CF₃CH₂NH | H | H | H |
| H | CF3 | CH₃O | H | H | H |
| H | CF3 | Cl | H | H | H |
| H | CF3 | NH₂ | H | H | H |
| H | CF3 | CH₃NH | H | H | H |
| H | CF3 | (CH₃)₂N | H | H | H |

TABLE 13

| R²⁰³ | R²⁰⁴ | R²⁰⁵ | R²⁰⁶ | R²⁰⁷ | R²⁰⁸ |
|---|---|---|---|---|---|
| CH₃(O)NHC | H | H | H | H | H |
| CH₂C(O)NHNH | H | H | H | H | H |
| CH₃OC(O)NH | H | H | H | H | H |
| CH₃OC(O)NHNH | H | H | H | H | H |
| (CH₃)₂NC(O)NH | H | H | H | H | H |
| (CH₃)₂NC(O)NHNH | H | H | H | H | H |
| (CH₃)₂NCH=N | H | H | H | H | H |
| (CH₃)₂S=N | H | H | H | H | H |
| (CH₃)₂S(O)=N | H | H | H | H | H |
| CH₃OC(O) | H | H | H | H | H |
| NH₂C(O) | H | H | H | H | H |
| CH₃NHC(O) | H | H | H | H | H |

TABLE 14

| R²⁰³ | R²⁰⁴ | R²⁰⁵ | R²⁰⁶ | R²⁰⁷ | R²⁰⁸ |
|---|---|---|---|---|---|
| H | CH₃(O)NHC | H | H | H | H |
| H | CH₃C(O)NHNH | H | H | H | H |
| H | CH₃OC(O)NH | H | H | H | H |
| H | CH₃OC(O)NHNH | H | H | H | H |

TABLE 14-continued

| $R^{203}$ | $R^{204}$ | $R^{205}$ | $R^{206}$ | $R^{207}$ | $R^{208}$ |
|---|---|---|---|---|---|
| H | (CH₃)₂NC(O)NH | H | H | H | H |
| H | (CH₃)₂NC(O)NHNH | H | H | H | H |
| H | (CH₃)₂NCH=N | H | H | H | H |
| H | (CH₃)₂S=N | H | H | H | H |
| H | (CH₃)₂S(O)=N | H | H | H | H |
| H | CH₃OC(O) | H | H | H | H |
| H | NH₂C(O) | H | H | H | H |
| H | CH₃NHC(O) | H | H | H | H |

TABLE 15

| $R^{203}$ | $R^{204}$ | $R^{205}$ | $R^{206}$ | $R^{207}$ | $R^{208}$ |
|---|---|---|---|---|---|
| H | H | CH₃(O)NHC | H | H | H |
| H | H | CH₃C(O)NHNH | H | H | H |
| H | H | CH₃OC(O)NH | H | H | H |
| H | H | CH₃OC(O)NHNH | H | H | H |
| H | H | (CH₃)₂NC(O)NH | H | H | H |
| H | H | (CH₃)₂NC(O)NHNH | H | H | H |
| H | H | (CH₃)₂NCH=N | H | H | H |
| H | H | (CH₃)₂S=N | H | H | H |
| H | H | (CH₃)₂S(O)=N | H | H | H |
| H | H | CH₃OC(O) | H | H | H |
| H | H | NH₂C(O) | H | H | H |
| H | H | CH₃NHC(O) | H | H | H |
| H | H | 2-chlorothiazol-5-ylmethylamino | H | H | H |
| H | H | 1,2,4-triazol-1-yl | H | H | H |
| H | H | pyrazol-1-yl | H | H | H |
| H | H | imidazol-1-yl | H | H | H |

TABLE 16

| $R^{203}$ | $R^{204}$ | $R^{205}$ | $R^{206}$ | $R^{207}$ | $R^{208}$ |
|---|---|---|---|---|---|
| H | pyrrolidin-1-yl | H | H | H | H |
| H | 2-oxopyrrolidin-1-yl | H | H | H | H |
| H | 2-oxooxazolidin-3-yl | H | H | H | H |
| H | 2-oxoimidazolidin-1-yl | H | H | H | H |
| H | 1,2,4-triazol-1-yl | H | H | H | H |
| H | H | 1,2,4-triazol-1-yl | H | H | H |
| H | H | pyrazol-1-yl | H | H | H |
| H | H | imidazol-1-yl | H | H | H |
| H | H | pyrrolidin-1-yl | H | H | H |
| H | H | 2-oxopyrrolidin-1-yl | H | H | H |
| H | H | 2-oxooxazolidin-3-yl | H | H | H |
| H | H | 2-oxoimidazolidin-1-yl | H | H | H |
| H | H | piperidin-1-yl | H | H | H |

TABLE 17

| $R^{203}$ | $R^{204}$ | $R^{205}$ | $R^{206}$ | $R^{207}$ | $R^{208}$ |
|---|---|---|---|---|---|
| H | pyridin-2-yl | H | H | H | H |
| H | pyridin-3-yl | H | H | H | H |
| H | pyridin-4-yl | H | H | H | H |

TABLE 17-continued

| $R^{203}$ | $R^{204}$ | $R^{205}$ | $R^{206}$ | $R^{207}$ | $R^{208}$ |
|---|---|---|---|---|---|
| H |  | H | H | H | H |
| H |  | H | H | H | H |
| H |  | H | H | H | H |
| H |  | H | H | H | H |
| H |  | H | H | H | H |
| H | H | 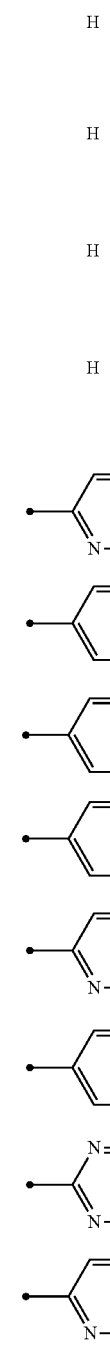 | H | H | H |
| H | H | 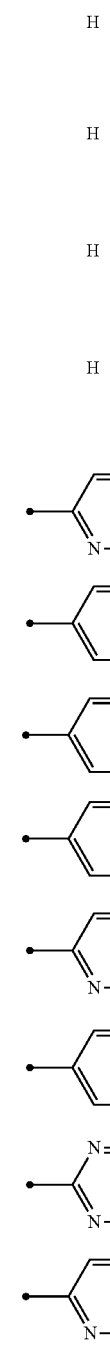 | H | H | H |
| H | H | 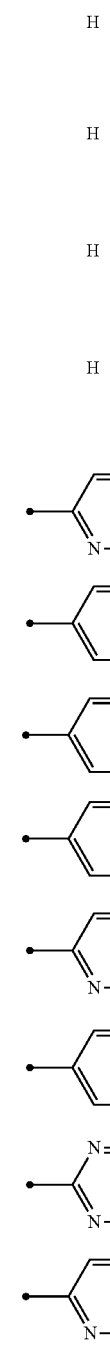 | H | H | H |
| H | H | 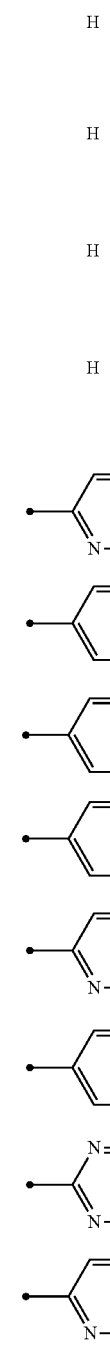 | H | H | H |
| H | H | 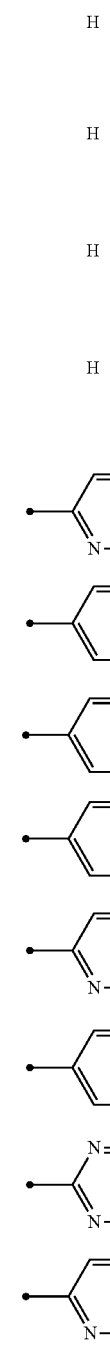 | H | H | H |
| H | H | 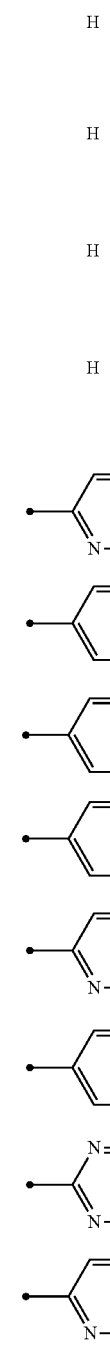 | H | H | H |
| H | H | 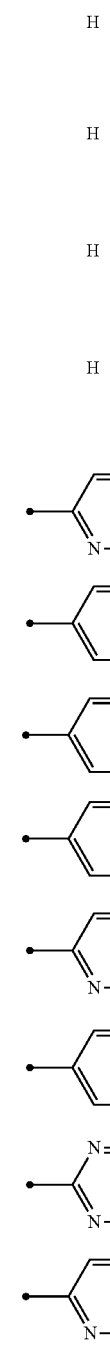 | H | H | H |
| H | H | 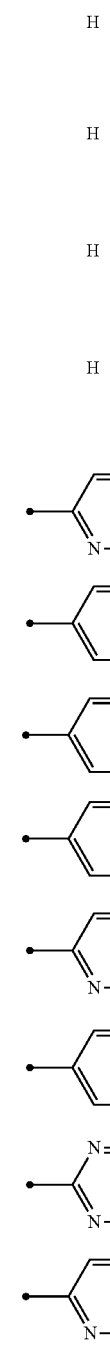 | H | H | H | a compound A represented by formula (200) wherein m is 0, n is 2, $R^{201}$ represents a 2,2,3,3-pentafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a 2,2,3,3,3-pentafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a 2,2,3,3,3-pentafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents a 1,1,2,3,3,3-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) where m is 1, n is 2, $R^{201}$ represents a 1,1,2,3,3,3-hexafluoropropyl group, $R^{202}$ represents an ethyl group, and $R^{203}$, $R^{204}$, $R^{205}$, $R^{206}$, $R^{207}$, $R^{208}$ represent any combination of the groups indicated in Table 11 to Table 17;

a compound A represented by formula (200) wherein m is 2, n is 2, $R^{201}$ represents a 1,1,2,3,3,3-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated Table 11 to Table 17;

a compound A represented by formula (200) wherein m is 0, n is 2, $R^{201}$ represents a 2,2,3,4,4,4-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a 2,2,3,4,4,4-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a 2,2,3,4,4,4-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents a 1,1,2-trifluoro-2-(trifluoromethoxy)ethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a 1,1,2-trifluoro-2-(trifluoromethoxy)ethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a 1,1,2-trifluoro-2-(trifluoromethoxy)ethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents a 2,2,3,3-tetrafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a 2,2,3,3-tetrafluoropropyl group, $R^{202}$ represents a methyl group, and $R^{203}$, $R^{204}$, $R^{205}$, $R^{206}$, $R^{207}$, and $R^{208}$ and represent any combination of the groups indicated in Table 11 to Table 17;

a compound A represented by formula (200) wherein m is 2, n is 2, $R^{201}$ represents a 2,2,3,3-tetrafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents 2,2,3,3,3-pentafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a 2, 2, 3, 3, 3-pentafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a 2,2,3,3,3-pentafluoropropyl group, $R^{202}$ represent a methyl group, and $R^{203}$, $R^{204}$, $R^{205}$, $R^{206}$, $R^{207}$, $R^{208}$ represent any combination of the groups indicated in Table 11 to Table 17;

a compound A represented by formula (200) wherein m is 0, n is 2, represents a 1,1,2,3,3,3-hexafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein in 1, n is 2, $R^{201}$ represents a 1,1,2,3,3,3-hexafluoropropyl group, $R^{202}$ represents methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a 1,1,2,3,3,3-hexafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents 2,2,3,4,4,4-hexafluorobutyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a 2, 2, 3, 4, 4, 4-hexafluorobutyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a 2,2,3,4,4,4-hexafluorobutyl group, $R^{202}$ represents a methyl group, $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents a 1,1,2-trifluoro-2-(trifluoromethoxy)ethyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is is 1, n is 2, $R^{201}$ represents a 1,1,2-trifluoro-2-(trifluoromethoxy)ethyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a 1,1,2-trifluoro-2-(trifluoromethoxy) ethyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents a trifluoromethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a trifluoromethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a trifluoromethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents a pentafluoroethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a pentafluoroethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a pentafluoroethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents a hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 1, n is 2, $R^{201}$ represents a hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, represents a heptafluorobutyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to able 17;

a compound A represented by formula (200) wherein m is 1, n is 2, $R^{201}$ represents a heptafluorobutyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a heptafluorobutyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 0, n is 2, $R^{201}$ represents a nonafluoropentyl group, $R^{202}$ represents an ethyl group, and $R^{203}$, $R^{204}$, $R^{205}$, $R^{206}$, $R^{207}$, and R208 represent any combination of the groups indicated in Table 11 to Table 17;

a compound A represented by formula (200) wherein m is 1, n is 2, $R^{201}$ represents a nonafluoropentyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein m is 2, n is 2, $R^{201}$ represents a nonafluoropentyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (200) wherein L represents an oxygen atom, m is 2, n is 2, $R^{201}$ represents a trifluoromethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound represented by formula (201):

(201)

[wherein the symbols are the same as defined above.].

a compound A represented by formula (201) wherein $R^{206}$, $R^{207}$, and $R^{208}$ represent independently of each other a hydrogen atom, and $R^{201}$, $R^{202}$, $R^{203}$, $R^{204}$, and $R^{205}$ represent any combination of the groups indicated in Table 1 to Table 10;

a compound A represented by formula (201) wherein n is 2, $R^{201}$ represents a 2,2,3,3-tetrafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (201) wherein n is 2, $R^{201}$ represents a 2,2,3,3,3-pentafluoropropyl group, $R^{202}$ represents an ethyl group, and $R^{203}$, $R^{204}$, $R^{205}$, $R^{206}$, $R^{207}$, and $R^{208}$ represent any combination of the groups indicated Table 11 to Table 17;

a compound A represented by formula (201) wherein n is 2, $R^{201}$ represents a 1,1,2,3,3,3-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (201) wherein n is 2, $R^{201}$ represents a 2,2,3,4,4,4-hexafluorobutyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (201) wherein n is 2, $R^{201}$ represents a 1,1,2-trifluoro-2-(trifluoromethoxy) ethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (201) wherein n is 2, $R^{201}$ a represents a 2,2,3,3-tetrafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (201) wherein n is 2, $R^{201}$ represents a 2,2,3,3,3-pentafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (201) wherein n is 2, $R^{201}$ represents a 1,1,2,3,3,3-hexafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (201) wherein n is 2, $R^{201}$ represents a 2,2,3,4,4,4-hexafluorobutyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (201) wherein n is 2, $R^{201}$ represents a 1,1,2-trifluoro-2-(trifluoromethoxy) ethyl group, $R^{202}$ represents a methyl group, and $R^{203}$, $R^{204}$, $R^{205}$, $R^{206}$, $R^{207}$, and $R^{208}$ represent any combination of the groups indicated Table 11 to Table 17;

a compound represented by formula (202):

(202)

[wherein the symbols are the same as defined above.].

a compound A represented by formula (202) wherein $R^{206}$, $R^{207}$, and $R^{208}$ represent independently of each other a hydrogen atom, and $R^{201}$, $R^{202}$, $R^{203}$, $R^{204}$, and $R^{205}$ represent any combination of the groups indicated in Table 1 to Table 10;

a compound A represented by formula (202) wherein n is 2, $R^{201}$ represents a 2,2,3,3-tetrafluoropropyl group, $R^{202}$ represents an ethyl group, and $R^{203}$, $R^{204}$, $R^{205}$, $R^{206}$, $R^{207}$ and $R^{208}$ represent any combination of the groups indicated in Table 11 to Table 17;

a compound A represented by formula (202) wherein n is 2, $R^{201}$ represents a 2,2,3,3,3-pentafluoropropyl group, $R^{202}$ represents an ethyl group, and $R^{203}$, $R^{204}$, $R^{205}$, $R^{206}$, $R^{207}$ and $R^{208}$ represent any combination of the groups indicated in Table 11 to Table 17;

a compound A represented by formula (202) wherein n 2, $R^{201}$ represents a 1,1,2,3,3,3-hexafluoropropyl group, represents an ethyl group, and $R^{203}$, $R^{204}$, $R^{205}$, $R^{206}$, $R^{207}$ and $R^{208}$ represent any combination of the groups indicated in Table 11 to Table 17;

a compound A represented by formula (202) wherein n is 2, $R^{201}$ represents a 2,2,3,4,4,4-hexafluorobutyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (202) wherein n 2, $R^{201}$ represents a 1,1,2-trifluoro-2-(trifluoromethoxy) ethyl group, $R^{202}$ represents an ethyl group, and $R^{203}$, $R^{204}$, $R^{205}$, $R^{206}$, $R^{207}$ and $R^{208}$ represent any combination of the groups indicated in Table 11 to Table 17;

a compound A represented by formula (202) wherein n is 2, $R^{201}$ represents a 2,2,3,3-tetrafluoropropyl group, $R^{202}$ represents a methyl group, and $R^{203}$, $R^{204}$, $R^{205}$, $R^{206}$, $R^{207}$ and $R^{208}$ represent any combination of the groups indicated in Table 11 to Table 17;

a compound A represented by formula (202) wherein n is 2, $R^{201}$ represents a 2,2,3,3,3-pentafluoropropyl group, $R^{202}$ represents a methyl group, and $R^{203}$, $R^{204}$, $R^{205}$, $R^{206}$, $R^{207}$ and $R^{208}$ represent any combination of the groups indicated in Table 11 to Table 17;

a compound A represented by formula (202) wherein n is 2, $R^{201}$ represents a 1,1,2,3,3,3-hexafluoropropyl group, $R^{202}$ represents a methyl group, and $R^{203}$, $R^{204}$, $R^{205}$, $R^{206}$, $R^{207}$ and $R^{208}$ represent any combination of the groups indicated in Table 11 to Table 17;

a compound A represented by formula (202) wherein n is 2, $R^{201}$ represents a 2,2,3,4,4,4-hexafluorobutyl group, $R^{202}$ represents a methyl group, and $R^{203}$, $R^{204}$, $R^{205}$, $R^{206}$, $R^{207}$ and $R^{208}$ represent any combination of the groups indicated in Table 11 to Table 17;

a compound A represented by formula (202) wherein n is 2, $R^{201}$ represents a 1,1,2-trifluoro-2-(trifluoromethoxy) ethyl group, $R^{202}$ represents a methyl group, and $R^{203}$, $R^{204}$, $R^{205}$, $R^{206}$, $R^{207}$ and $R^{208}$ represent any combination of the groups indicated in Table 11 to Table 17;

a compound represented by formula (203):

(203)

[wherein the symbols are the same as defined above.].

a compound A represented by formula (203) wherein $R^{206}$, $R^{207}$, and $R^{207}$ represent independently of each other a hydrogen atom, and $R^{201}$, $R^{202}$, $R^{203}$, $R^{204}$ and $R^{205}$ represent any combination of the groups indicated in Table 1 to Table 10;

a compound A represented by formula (203) wherein n is 2, $R^{201}$ represents a 2,2,3,3-tetrafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (203) wherein n is 2, $R^{201}$ represents a 2,2,3,3,3-pentafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (203) wherein n is 2, $R^{201}$ represents a 1,1,2,3,3,3-hexafluoropropyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (203) wherein n is 2, $R^{201}$ represents a 2,2,3,4,4,4-hexafluorobutyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (203) wherein n is 2, $R^{201}$ represents a 1,1,2-trifluoro-2-(trifluoromethoxy) ethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound A represented by formula (203) wherein n is 2, $R^{201}$ represents a 2,2,3,3-tetrafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (203) wherein n is 2, $R^{201}$ represents a 2,2,3,3,3-pentafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (203) wherein n is 2, $R^{201}$ represents a 1,1,2,3,3,3-hexafluoropropyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (203) wherein n is 2, $R^{201}$ represents a 2,2,3,4,4,4-hexafluorobutyl group, $R^{202}$ represents a methyl group, and $R^{203}$, $R^{204}$, $R^{205}$, $R^{206}$, $R^{207}$, and $R^{208}$ represent any combination of the groups indicated in Table 11 to Table 17;

a compound A represented by formula (203) wherein n is 2, $R^{201}$ represents a 1,1,2-trifluoro-2-(trifluoromethoxy) ethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to Table 17;

a compound represented by formula (300):

(300)

[wherein $R^{206}$, $R^{207}$, and $R^{208}$ represent independently of each other a hydrogen atom, n is 0, and $R^{201}$, $R^{202}$, $R^{203}$, $R^{204}$, and $R^{205}$ represent any combination of the groups indicated in Table 1 to 10;

a compound A represented by formula (300) wherein $R^{206}$, $R^{207}$, and $R^{208}$ represent independently of each other a hydrogen atom, n is 1, and $R^{201}$, $R^{202}$, $R^{203}$, $R^{204}$, and $R^{205}$ represent any combination of the groups indicated in Table 1 to 10;

a compound A represented by formula (300) wherein $R^{206}$, and $R^{207}$, and $R^{208}$ represent independently of each other a hydrogen atom, n is 2, and $R^{201}$, $R^{202}$, $R^{203}$, $R^{204}$, and $R^{205}$ represent any combination of the groups indicated in Table 1 to 10;

a compound A represented by formula (300) wherein $R^{206}$ represents a chlorine atom, $R^{207}$ and $R^{208}$ represent independently of each other a hydrogen atom, n is 0, and $R^{201}$, $R^{202}$, $R^{203}$, $R^{204}$, and $R^{205}$ represent any combination of the groups indicated in Table 1 to 10;

a compound A represented by formula (300) wherein $R^{206}$ represents a chlorine atom, and $R^{207}$ and $R^{208}$ represent independently of each other a hydrogen atom, n is 1, and $R^{201}$, $R^{202}$, $R^{203}$, $R^{204}$, and $R^{205}$ represent any combination of the groups indicated in Table 1 to 10;

a compound A represented by formula (300) wherein $R^{206}$ represents a chlorine atom, $R^{207}$ and $R^{208}$ represent independently of each other a hydrogen atom, n is 2, and $R^{201}$, $R^{202}$, $R^{203}$, $R^{204}$, and $R^{205}$ represent any combination of the groups indicated in Table 1 to 10;

a compound A represented by formula (300) wherein $R^{206}$ represents a methyl group, $R^{207}$ and $R^{208}$ represent independently of each other a hydrogen atom, n is 0, and $R^{201}$, $R^{202}$, $R^{203}$, $R^{204}$, and $R^{205}$ represent any combination of the groups indicated in Table 1 to 10;

a compound A represented by formula (300) wherein $R^{206}$ represents a methyl group, $R^{207}$ and $R^{208}$ represent independently of each other a hydrogen atom, n is 0, and $R^{201}$, $R^{202}$, $R^{203}$, $R^{204}$, and $R^{205}$ represent any combination of the groups indicated in Table 1 to 10;

a compound A represented by formula (300) wherein $R^{206}$ represents a methyl group, $R^{207}$ and $R^{208}$ represent independently each other a hydrogen atom, n is 1, and $R^{201}$, $R^{202}$, $R^{203}$, $R^{204}$, and $R^{205}$ represent any combination of the groups indicated in Table 1 to 10;

a compound A represented by formula (300) wherein $R^{206}$ represents a methyl group, $R^{207}$ and $R^{208}$ represent independently of each other a hydrogen atom, n is 2, and $R^{201}$, $R^{202}$, $R^{203}$, $R^{204}$, and $R^{205}$ represent any combination of the groups indicated in Table 1 to 10;

a compound A represented by formula (300) wherein $R^{206}$ represents a trifluoromethyl group, $R^{207}$ and $R^{208}$ represent independently of each other a hydrogen atom, n is 0, and $R^{201}$, $R^{202}$, $R^{203}$, $R^{204}$, and $R^{205}$ represent any combination of the groups indicated in Table 1 to 10;

a compound A represented by formula (300) wherein $R^{206}$ represents a trifluoromethyl group, $R^{207}$ and $R^{208}$ represent independently of each other a hydrogen atom, n is 1, and $R^{201}$, $R^{202}$, $R^{203}$, $R^{204}$, and $R^{205}$ represent any combination of the groups indicated in Table 1 to 10;

a compound A represented by formula (300) wherein $R^{206}$ presents a trifluoromethyl group, $R^{207}$ and $R^{208}$ represent independently of each other a hydrogen atom, n is 2, and $R^{201}$, $R^{202}$, $R^{203}$, $R^{204}$, and $R^{205}$ represent any combination of the groups indicated in Table 1 to 10;

a compound A represented by formula (300) wherein $R^{207}$ represents a chlorine atom, $R^{206}$ and $R^{208}$ represent independently of each other a hydrogen atom, n is 0, and $R^{201}$, $R^{202}$, $R^{203}$, $R^{204}$, and $R^{205}$ represent any combination of the groups indicated in Table 1 to 10;

a compound A represented by formula (300) wherein $R^{207}$ represents a chlorine atom, $R^{206}$ and $R^{208}$ represent independently of each other a hydrogen atom, n is 1, and $R^{201}$, $R^{202}$, $R^{203}$, $R^{204}$, and $R^{205}$ represent any combination of the groups indicated in Table 1 to 10;

a compound A represented by formula (300) wherein $R^{207}$ represents a chlorine atom, $R^{206}$ and $R^{208}$ represent independently of each other a hydrogen atom, n is 2, and $R^{201}$, $R^{202}$, $R^{203}$, $R^{204}$, and $R^{205}$ represent any combination of the groups indicated in Table 1 to 10;

a compound A represented by formula (300) wherein $R^{207}$ represents methyl group, $R^{206}$ and $R^{208}$ represent independently of each other a hydrogen atom, n is 1, and $R^{201}$, $R^{202}$, $R^{203}$, $R^{204}$, and $R^{205}$ represent any combination of the groups indicated in Table 1 to 10;

a compound A represented by formula (300) wherein $R^{207}$ represents a methyl group, $R^{206}$ and $R^{208}$ represent independently of each other a hydrogen atom, n is 2, and $R^{201}$, $R^{202}$, $R^{203}$, $R^{204}$, and $R^{205}$ represent any combination of the groups indicated in Table 1 to 10;

a compound A represented by formula (300) wherein $R^{207}$ represents a trifluoromethyl group, $R^{206}$ and $R^{208}$ represent independently of each other a hydrogen atom, n is 0, and $R^{201}$, $R^{202}$, $R^{203}$, $R^{204}$, and $R^{205}$ represent any combination of the groups indicated in Table 1 to 10;

a compound A represented by formula (300) wherein $R^{207}$ represents a trifluoromethyl group, $R^{206}$ and $R^{208}$ represent independently of each other a hydrogen atom, n is 1, and $R^{201}$, $R^{202}$, $R^{203}$, $R^{204}$, and $R^{205}$ represent any combination of the groups indicated in Table 1 to 10;

a compound A represented by formula (300) wherein $R^{207}$ represents a trifluoromethyl group, $R^{206}$ and $R^{208}$ represent independently of each other a hydrogen atom, n is 2, and $R^{201}$, $R^{202}$, $R^{203}$, $R^{204}$, and $R^{205}$ represent any combination of the groups indicated in Table 1 to 10;

a compound A represented by formula (300) wherein n is 2, $R^{201}$ represents a trifluoromethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to 17;

a compound A represented by formula (300) wherein n is 2, $R^{201}$ represents a pentafluoroethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to 17;

a compound A represented by formula (300) wherein n is 2, $R^{201}$ represents a 2,2,2-trifluoroethyl group, $R^{202}$ represents an ethyl group, and $R^{203}$, $R^{204}$, $R^{205}$, $R^{206}$, $R^{207}$, and $R^{208}$ represent any combination of the groups indicated in Table 11 to 17.

Examples of the harmful arthropods on which a compound A has a control efficacy include harmful insets and harmful mites. Specific examples of the harmful arthropods are follows, but which are limited thereto.

Hemiptera Pests:

Delphacidae (for example, *Laodelphax striatellus, Nilaparvata lugens, Sogatella furcifera*, or *Peregrinus maidis*), Deltocephalidae (for example, *Nephotettix cincticeps, Nephotettix virescens, Nephotettix nigropictus* (Rice green leafhopper), *Recilia dorsalis, Empoasca onukii, Empoasca fabae, Dalbulus maidis, Mahanarva posticata* (Sugarcane froghopper), *Mahanarva fimbriolota* (Sugarcane root spittlebug), *Cofana spectra,* or *Nephotettix nigropictus, Recilia dorsalis*), Aphididae (for example, *Aphis gossypii, Myzus persicae, Brevicoryne brassicae, Aphis spiraecola, Macrosiphum euphorbiae, Aulacorthum solani, Rhopalosiphum padi, Toxoptera citricidus, hyalopterus pruni, Aphis glycines Matsumura, Rhopalosiphum maidis, Tetraneura nigriabdominalis, Viteus vitifoliae, Daktulosphaira vitifoliae* (Grape Phylloxera), *Phylloxera devastatrix Pergande* (Pecan phylloxera), *Phylloxera notabilis pergande* (Pecan leaf phylloxera), or *Phylloxera russellae Stoetzel* (Southern pecan leaf phylloxera), Pentatomidae (for example, *Scotinophara lurida, Scotinophara coarccata* (Malayan rice black bug), *Nezara antennata, Eysarcoris parvus, Halyomorpha mista, Nezara viridula, Euschistus heros* (Brown stink bug), *Nezara*

*viridula* (Southern green stink bug), *Piezodorus guildinii* (Red banded stink bug), *Scaptocoris castanea* (Burrower brown bug), *Oebalus pugnax*, or *Dichelops melacanthus*), Alydidae (for example, Riptortus clavetus, *Leptocorisa chinensis, Leptocorisa acuta*, or *Leptocorisa* spp.), Miridae (for example, *Trigonotylus caelestialium, Stenotus rubrovittatus, Lygus lineolaris*, or *Blissus leucopterus leucopterus* (Chinchi bug)), Aleyrodidae (for example, *Trialeurodes vaporariorum, Bemisia tabaci, Dialeurodes citri*, or *Aleurocanthus spiniferus*), Coccoidea (for example, *Aonidiella aurantii, Comstockaspis perniciosa, Unaspis citri, Ceroplastes rubens, Icerya purchasi, Planococcus Kraunhiae, Pseudococcus longispinis, Pseudaulacaspis Pentagona*, or *Brevennia rehi*), Psyilidae (for example, *Diaphorina citri, Psylla pyrisuga, Bactericerca cockerelli*), Tingidae (for example, *Stephanitis nasi*), Cimicoidea (for example, *Cimex lectularius*), Quesada gigas (Giant Cicada);

and the others.

Lepidoptera Pests:

Pyralidae (for example, *Chilo suppressalis, Chilo polychrysus* (Darkheaded stm borer), *Tryporyza incertulas*, Chilo polychrysus, Scirpophaga innotata, *Scirpophaga incertulas* (Yellow stem borer), *Sesamia inferens* (Pink borer), *Rupela albinella, Cnaphalocrocis medinalis, Marasmia patnalis, Marasmia exigna, Notarcha derogata, Plodia interpunctella, Ostrinia furnacalis, Hellula undalis, Pediasia teterrellus, Nymphula depunctalis, Marasmia* spp., *Hydraecia immanis* (Hop vine borer), *Ostrinia nubilalis* (European corn borer), *Elasmopalpus lignosellus* (Lesser cornstalk borer), *Epinotia aporema* (Bean Shoot Borer), *Diatraea saccharalis* (Sugarcane borer), *Telchin licus* (Giant Sugarcane borer)), Noctuidae (for example, *Spodoptera litura, Spodoptera exigua, Pseudaletia separata, Mamestra brassicae, Sesamia inferens, Spodoptera mauritia, Spodoptera frugiperda, Spodoptera exempta, Agrotis ipsilon, Plusia nigrisigna, Pseudoplusia includens* (Soybean looper), *Trichoplusia* spp., *Heliothis* spp. (for example, *Heliothis virescens*), *Helicoverpa* spp. (for example, *Helicoverpa armigera*), *Anticarsia gammatalis* (Velvetbean caterpillar), or *Alabama argillacea* (Cotton leafworm)), Pieridae (for example, *Pieris rapae*), Adokisofiesu genus, Tortricidae (for example, *Grapholita molesta, Leguminivora glycinivorella, Matsumuraeses azukivora, Adoxophyes orana fasciata, Adoxophyes honmai, Homona magnanima, Archips fuscocupreanus*, or *Cydia pomonella*), Gracillariidae (for example, *Caloptilia theivora*, or *Phyllonorycter ringoneella*), Carposinidae (for example, *Carposina niponensis, Ecdytolopha aurantiana* (Citrus fruit borer)), Lyonetiidae (for example, *Leucoptera coffeela* (Coffee Leaf miner), *Lyonetia* spp.)), Lymatriidae (for example, *Lymantria* spp., or *Euproctis* spp.), Yponomeutidae (for example, *Plutella xylostella*), Gelechiidae (for example, *Pectinophora gossypiella*, or *Phthorimaea operculella*), Arctiidae (for example, *Hyphantria cunea*);

and the others.

Thysanoptera Pests:

Thysanoptera (for example, *Frankliniella occidentalis, Thrips parmi, Scirtothrips dorsalis, Thrips tabaci, Franklin-iella intonsa, Frankliniella occidentalis, Haplothrips aculeatus, Stenchaetothrips biformis*);

and the others.

Diptera Pests:

Diptera:

House mosquitoes (*Culex* spp.) (for example, *Culex pipiens pallens, Culex tritaeniorhynchus*, or *Culex quinquefasciatus*), Aedes spp. (for example, *Aedes aegypti*, or *Aedes albopictus*), Anopheles spp. (for example, Anopheles sinensis), Chironomidae, Muscidae (for example, *Musca domestica*, or *Muscina stabulans*), Anthomyiidae (for example, *Delia platura, Delia antiqua*, or *Tetanops myopaeformis*), Agromyzidae (for example, *Agromyza oryzae, Hydrellia griseola, Liriomyza sativae, Liriomyza trifolii*, or *Chromatomyia horticola*), Chloropidae (for example, *Chlorops oryzae*), Tephritidae (for example, *Dacus cucurbitae*, or *Ceratitis capitata*), Ephydridae (for example, *Hydrellia philippina*, or *Hydrellia sasakii*), Drosophilidae, Phoridae (for example, *Megaselia spiracularis*), Psychodidae (for example, *Clogmia albipunctata*), Sciaridae, Cecidomyiidae (for example, *Mayetiola destructor*, or *Orseolia oryzae*), Diopsidae (for example, *Diopsis macrophthalma*), Tipulidae (for example, *Tipula oleracea* (Common cranefly), or *Tipula paludosa* (European cranefly));

and the others.

Coleoptera Pests:

Chrysomelidae (for example, *Diabrotica virgifera virgifera, Diabrotica undecimpunctata howardi, Diabrotica barberi, Diabrotica virgifera zeae, Diabrotica balteata LeConte, Diabrotica speciosa, Diabrotica speciosa* (Cucurbit Beetle), *Cerotoma trifurcata, Oulema melanopus, Aulacophora femoralis, Phyllotreta striolata, Leptinotarsa decemlineata, Oulema oryzae, Colaspis brunnea, Chaetocnema pulicaria, Epitrix cucumeris, Dicladispa armigera, Stenolophus lecontei* (Seedcorn beetle), or *Clivinia impressifrons* (Slender seedcorn beetle)), Scarabaeidae (for example, Anomala cuprea, *Anomala rufocuprea, Popillia japonica, Rhizotrogus majalis* (European Chafer), *Bothynus gibbosus* (Carrot beetle), *Colaspis brunnea* (Grape Colaspis), *Myochrous denticollis* (southern Corn leaf beetle), *Holotrichia* spp., or *Phyllophaga* spp. (for example, Phyllophaga crinita)), Erirhinidae (for example, *Sitophilus zeamais, Echinocnemus squameus, Lissorhoptrus oryzophilus*, or *Sphenophorus venatus*), Curculionidae (for example, *Anthonomus grandis, Sphenophorus callosus* (Southern Corn Billbug), *Sternechus subsignatus* (Soybean stalk weevil), or *Sphenophorus* spp. (for example, Sphenophorus levis)), Epilachna (for example, *Epilachna vigintioctopunctata*), Scolytidae (for example, *Lyctus brunneus*, or *Tomicus piniperda*), Bostrichidae, Ptinidae, Cerambycidae (for example, *Anoplophora malasiaca*, or *Migdolus fryanus*), Elateridae (*Agriotes* sp., *Aelous* sp., *Anchastus* sp., *Melanotus* sp., *Limonius* sp., *Conoderus* sp., *Ctenicera* sp.) (for example, Melanotus okinawensis, Agriotes ogurae fuscicollis, or Melanotus legatus), Staphylinidae (for example, *Paederus fuscipes*), Hypothenemus hampei (Coffee Barry Borer);

and the others.

Orthoptera Pests:

*Locusta migratoria, Gryllotalpa africana, Dociostaurus maroccanus, Chortoicetes terminifera, Nomadacris septemfasciata, Locustana pardalina* (Brown Locust), *Anacridium melanorhodon* (Tree Locust), *Calliptamus italicus* (Italian Locust), *Melanoplus differentialis* (Differential grasshopper) , *Melanoplus bivittatus* (Twostriped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria, Gastrimargus musicus* (Yellow-winged locust), *Austracris guttulosa* (Spur-throated locust), *Oxya yezoensis, Oxya japonica, Patanga succincta, Grylloidea* (for example, *Acheta domesticus, Teleogryllus emma*, or *Anabrus simplex* (Mormon cricket));

and the others.

Hymenoptera Pests:

Tenthredinidae (for example, *Athalia rosae*, or *Atralia japonica*),

*Solenopsis* spp.,

*Acromyrmex* spp. (for example, *Atta capiguara* (Brown leaf-cutting ant));

and the others.

Blattariae Pests:

*Blattella germanica, Periplaneta fuliginosa, Periplaneta americana, Periplaneta brunnea, Blatta orientalis*, and the others.

Isoptera Pests:

*Reticulitermes speratus, Coptotermes formosanus, Incisitermes minor* (Coptotermes formosanus), *Cryptotermes domesticus, Odontotermes formosanus, Neotermes koshunensis, Glyptotermes satsumensis, Glypototermes nakajimai, Glyptotermes fuscus, Glyptotermes kodamai, Glyptotermes kushimensis, Hodotermopsis sjostedti, Coptotermes guangzhoensis, Reticulitermes amamianus, Reticulitermes miyatakei, Reticulitermes kanmonensis, Nasutitermes takasagoensis, Pericapritermes nitobei, Sinocapritermes mushae*, or *Cornitermes cumulans*);

and the others.

Acarina Pests:

Tetranychidae (for example, *Tetranychus urticae, Tetranychus kanzawai, Panonychus citri, Panonychus ulmi, Oligonyohus* spp., or *Brevipalpus phoenicis* (Southern Turkey spider mites)), Eriophyidae (for example, *Aculops pelekassi, Phyllocoptruta citri, Aculops lycopersici, Calacarus carinatus, Acaphylla theavagrans, Eriophyes chibaensis*, or *Aculus schlechtendali*), Tarsonemidae (for example, *Polyphagotarsonemus latus*), Tenuipalpidae (for Example, *Brevipalpus phoenicis*), Tuckerellidae;

Ixodidae (for Example, *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus*, or *Rhipicephalus sanguineus*), Acaridae (for example, *Tyrophagus putrescentiae*, or *Tyrophagus similis*), Pyroglyphidae (for example, *Dermatophagoides farinae*, or *Dermatophagoides ptrenyssnus*);.

and the others.

Spiders: Eutichuridae (for example, *Cheiracanthium japonicum*), and Theridiidae (for example, *Latrodectus hasseltii*);

Chilopoda: Scutigeridae (for example, *Thereuonema hilgendorfi*), and Scolopendridae (for example, Scolopendra subspinipes);

Diplopoda: Paradoxosomatidae (for example, *Oxidus gracilis, Nedyopus tambanus*);

Isopoda: Armadillidiidae (for example, *Armadillidium vulgare*);

Gastropoda: Limacida (for example, *Limax marginatus*, and *Limax flavus*); Ampullariidae (for example, *Pomacea canaliculata*); and Lymnaeidae (for example, *Austropeplea ollula*)).

Nematodes: Aphelenchoididae (for example, *Aphelenchoides basseyi*); Pratylenchida (for example, *Pratylenchus coffeae, Pratylenchus brachyurus, Pratylenchus neglectus*, and *Radopholus similis*); Heteroderidae (for example, *Meloidogyne javanica, Meloidogyne incognita, Meloidogyne hapla, Heterodera glycines, Globodera rostochiensis*, and *Globodera pallida*); Hoplolaimidae (for example, *Rotylenchulus reniformis*); Anguinidae (for example, *Nothotylenchus acris*, and *Ditylenchus dipsaci*); Tylenchulidae (for example, *Tylenchulus semipenetrans*); Longidoridae (for example, *Xiphinema index*); Trichodoridae; and Parasitaphelenchidae example, *Bursaphelenchus xylophilus*).

The harmful insects and harmful mites to be controlled may insects or mites whose a drug-sensitivity to any of insecticides and miticides is lowered or whose a drug-resistance against any of insecticides and miticides developed. However, when the drug-sensitivity is largely lowered or the drug-resistance is largely developed, the composition of the present invention comprising any insecticides and/or miticides other than the particular insecticides and/or miticides is preferably used.

The compound A may be used to protect plants from the plant diseases caused by insect-mediated viruses.

Examples of the plant diseases caused by the insect-mediated viruses on which the compound A has a control efficacy include as follows.

Rice dwarf disease (Rice waika virus), Rice tungro disease (Rice tungro spherical virus, Rice tungro bacilliform virus), Rice grassy stunt disease (Rice grassy stunt virus), Rice ragged stunt disease (Rice ragged stunt virus), Rice stripe disease (Rice stripe virus), Rice black streaked dwarf disease (Rice black streaked dwarf virus), Southern rice black-streaked dwarf disease (Southern rice black-streaked dwarf virus), Rice gall dwarf disease (Rice gall dwarf virus), White leaf disease of rice (Rice white leaf virus), Yellow dwarf disease (Yellow dwarf virus), Red disease (Rice penyakit merah virus), Rice yellow stunt disease (Rice yellow stunt virus), Rice transitory yellowing disease (Rice transitory yellowing virus), Rice Yellow Mottle disease (Rice Yellow Mottle Virus), Rice necrosis mosaic disease (Rice necrosis mosaic virus), Rice dwarf stunt disease (Rice dwarf stunt virus), Wheat northern cereal mosaic disease (Northern Cereal Mosaic Virus), Barley Yellow Dwarf disease (Barley Yellow Dwarf Virus), Wheat yellow dwarf disease (Wheat yellow dwarf virus), Oat sterile dwarf disease (Oat sterile dwarf virus), Wheat streak mosaic disease (Wheat streak mosaic virus);

Maize dwarf mosaic disease (Maize dwarf mosaic virus), Maize stripe disease (maize stripe tenuivirus), Maize chlorotic dwarf disease (Maize chlorotic dwarf virus), Maize chlorotic mottle disease (maize chlorotic mottle virus), Maize rayado fino disease (maize rayado fino marafivirus), Corn stunt disease (corn stunt spiroplasma), Maize bushy stunt disease (Maize bushy stunt phytoplasma);

Sugarcane mosaic disease (Sugarcane mosaic virus);

Soybean mild mosaic disease (Soybean mild mosaic virus), Mosaic disease (Alfalfa Mosaic Virus, Bean yellowspot mosaic virus, Soybean mosaic virus, Bean yellow mosaic virus, Cowpea severe mosaic virus), bean virus disease (Broad bean wilt virus, Bean common mosaic virus, Peanut stunt virus, Southern bean mosaic virus), Soybean dwarf disease (Soybean dwarf luteovirus, Milk-vetch dwarf luteovirus), Bean-pod mottle disease (Bean-pod mottle virus), Brazilian bud blight disease (Tobbaco streak virus), Cowpea chlorotic mottle disease (Cowpea chlorotic mottle), Mung bean yellow mosaic disease (Mung bean yellow mosaic virus), Peanut stripe disease (Peanut stripe mottle), Soybean crinkle leaf disease (Soybean crinkle leaf virus), Soybean severe stunt disease (Soybean severe stunt virus);

Tomato yellow leaf disease (Tomato chlorosis virus), Tomato spotted wilt disease (Tomato spotted wilt virus), Tomato yellow leaf curl disease (Tomato yellow leaf curl virus), Melon spotted wilt disease (Melon yellow spot virus), Watermelon mosaic disease (Watermelon mosaic virus), Dwarf disease (Cucumber mosaic virus), Zucchini yellow mosaic disease (Zucchini yellow mosaic virus), Turnip mosaic disease (Turnip mosaic virus), Cucurbit chlorotic yellow disease (Cucurbit chlorotic yellows virus), Capsicum chlorosis disease (Capsicum chlorosis virus), Beet pseudo yellow disease (Beet pseudo yellows virus);

chrysanthemum stem necrosis disease (chrysanthemum stem necrosis virus), Impatiens necrotic spot disease (Impatiens necrotic spot virus), Iris yellow spot disease (Iris yellow spot virus);

Sweet potato mottle mosaic disease (Sweet potato internal cork virus), Sweet potato shukuyo mosaic disease (Sweet potato shukuyo mosaic virus); and Mosaic virus diseases of various plants mediated by Polymixa spp. or Olpidium spp.

The agent for controlling pests of the present invention comprises the compound A and an inert active carrier. The agent for controlling harmful arthropods is usually prepared by mixing the present compound with an inert active carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment.

The agent for controlling pests of the present invention comprises usually 0.01 to 95% by weight of the compound A.

Examples of the solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for Example, polyester resins such as polypropylene, polyacrylonitrile, polymethylmethacrylate and polyethylene terephthalate; nylon resins (for Example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for Example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for Example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol); acid amides (for Example, N,N-dimethylformamide or N,N-dimethylacetamide); halogenated hydrocarbons (for Example, dichloromethane, trichloroethane or carbon tetrachloride); sulfoxides (for Example, dimethyl sulfoxide) ; propylene carbonate; and vegetable oils (for Example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids) , PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol).

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling harmful arthropods of the present invention is conducted by applying an effective amount of the compound A to a harmful arthropod directly and/or a habitat thereof (for example, plant bodies, soil, an interior of a house, animal bodies). In the method for controlling harmful arthropods of the present invention, the present compound is usually used in the form of harmful arthropod controlling agent.

When an agent for controlling harmful opods of the present: invention is used for controlling harmful arthropods in an agricultural field, the application dose as an amount of the compound A is usually within a range from 1 to 10,000 g per 10,000 m². The emulsifiable concentrate, the wettable powder, or the flowable formulation etc. of an agent for controlling harmful arthropods of the present invention is usually applied by diluting it with water in such a way that a concentration of the active ingredient is within a range from 0.01 to 10,000 ppm. The granular formulation, or the dust formulation etc., is usually applied as itself without diluting it.

These formulations or a water dilution thereof can be sparged directly to harmful arthropods or plants to be protected from harmful arthropods, and also may be applied to the soil of crop land in order to control harmful arthropods which live there.

The resin preparation which is processed into a sheet or a string may be applied by winding a crop with a sheet or a string of the resin preparation, putting a string of the resin preparation around a crop so that the crop is surrounded by the string, or laying a sheet of the resin preparation on the soil surface near the root of a crop.

When the agent for controlling harmful arthropods of the present invention is used to control pests that live inside a house, the application dose as an amount of the compound A is usually within a range from 0.01 to 1,000 mg per 1 m² an area to be treated, in the case of using it on a planar area. In the case of using it spatially, the application dose as an amount of the compound A is usually within a range from 0.01 to 500 mg per 1 m³ of the space to be treated. When the agent controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the agent for controlling harmful arthropods of the present invention is sued for controlling external parasites of livestock such as cows, horses, pigs, sheep, goats and chickens and small animals such as dogs, cats, rats and mice, the pest control agent of the present invention can be applied to the animals by a known method in the veterinary field. Specifically, when systemic control is intended, the pest control agent of the present invention is administered to the animals as a tablet, a mixture with feed or a suppository, or by injection (including intramuscular, subcutaneous, intravenous and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of administering to an animal body, the dose of the compound A is usually within a range from 0.1 to 1,000 mg per 1 kg of an animal weight.

EXAMPLES

Hereinafter, the present invention is explained in more detail by using Preparation example, Formulation example, and Test example, however, the present invention should not be limited to these examples.

First, with respect to the preparation of the compound A, the Preparation example is shown.

Preparation Example 1-1

To a mixture of 1.6 M butyl lithium-hexane solution 100 mL, and 160 mL of THE were added dropwise a mixture of ethyl methyl sulfone 23 g and THF 20 mL at −78° C. The reaction mixtures were raised gradually to 0° C. and were then re-cooled to −78° C. To the reaction mixtures was added dropwise a mixture of 5-fluoro-2-cyanopyridine 20 g and THF 20 mL at −78° C. The mixtures were raised gradually to room temperature, and to the reaction mixtures was added 2N hydrochloric acid, and the mixtures were stirred for 30 minutes. The resulting mixtures were extracted with ethyl acetate and the organic layers were washed with saturated brine. The organic layers were dried over anhydrous sodium sulfate and concentrated under reduced pressure to obtain the compound 1 below 40 g.

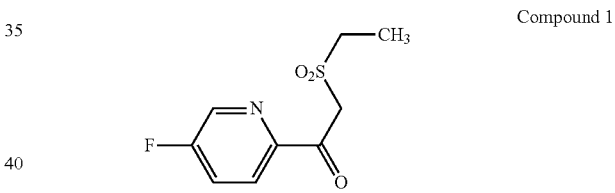

Compound 1

$^1$H-NMR (CDCl$_3$) δ: 8.57 (1H, d), 8.19 (1H, dd), 7.62-7.55 (1H, m), 4.97 (2H, s), 3.30 (2H, q), 1.47 (3H, t).

Preparation Example 1-2

To a mixture of oxalyl chloride 11 mL and chloroform 86 mL was added dropwise DMF 10 mL under ice-cooling. The mixtures were stirred for 30 minutes under ice-cooling, and to the mixtures was then added dropwise butyl vinyl ether 33 mL. The mixtures were raised to room temperature, and stirred for two hours, and to the mixtures was then added a mixture of the compound 1 10 g, triethylamine 42 mL and chloroform 30 mL under ice-cooling. The mixtures were raised to room temperature, and then stirred for one hour. The resulting mixtures was added to a saturated aqueous ammonium chloride solution and extracted with chloroform. The resulting organic layers were washed with water and saturated brine, dried over anhydrous sodium sulfate and concentrated under reduced pressure. The obtained residue was diluted with ethanol 30 mL and thereto was added 28% aqueous ammonia solution 10 mL at room temperature. The mixtures were heated at 60° C. with stirring for 2.5 hours, and then stood to cool to room temperature. Thereto was added saturated aqueous sodium carbonate solution, and the mixtures were extracted with ethyl acetate. The resulting organic layers were dried over anhydrous sodium sulfate and concentrated under reduced pressure. The obtained residue was subjected to a silica gel column chromatography to obtain the compound 2 below 9.4 g.

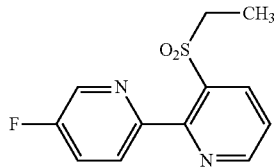

Compound 2

$^1$H-NMR (CDCl$_3$) δ: 8.88 (1H, dd), 8.52-8.46 (2H, m), 7.87 (1H, dd), 7.62-7.54 (2H, m), 3.86 (2H, g), 1.38 (3H, t).

Preparation Example 1-3

To a mixture of the compound 2 9.4 g and NMP 120 mL was added sodium hydrogen sulfide n hydrate 8.3 g at room temperature. The mixtures were heated at 100° C. with stirring for three hours. To the resulting reaction mixtures were added ethyl acetate 200 mL and concentrated hydrochloric acid under ice-cooling to adjust pH to 4, and the mixtures were stirred for 30 minutes. The resulting mixtures were extracted with ethyl acetate. The organic mixtures were dried over anhydrous sodium sulfate, and concentrated under reduced pressure. To the crude mixtures was added 10% aqueous potassium carbonate solution 50 mL room temperature, and the mixtures were stirred at room temperature for five hours. To the resulting mixtures was added water 100 mL, and the mixtures were extracted with ethyl acetate. The organic layers were dried over anhydrous sodium sulfate and concentrated under reduced pressure. The obtained residues were subjected to a silica gel column chromatography to obtain the compound 3 below 7.6 g.

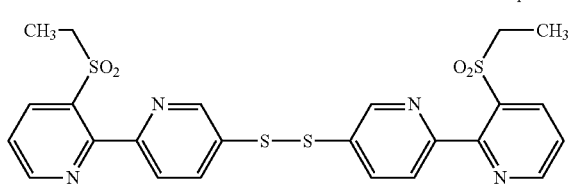

Compound 3

$^1$H-NMR (CDCl$_3$) δ: 8.88 (1H, dd), 8.67 (1H, dd), 8.49 (1H, dd), 8.00 (1H, dd), 7.83 (1H, d), 7.56 (1H, dd), 3.88 (2H, g), 1.36 (3H, t).

Preparation Example 1-4

To a mixture of the compound 3 1.0 g, potassium carbonate 990 mg, hydroxymethane sulfinic acid dihydrate 1.1 g, and NMP 10 mL was added 2,2,2-trifluoroethyl trifluoromethane sulfonate (hereinafter, referred to as Compound 4) 830 mg under ice-cooling. The reaction mixtures were stirred at room temperature for two hours. To the resulting mixtures was added saturated aqueous sodium hydrogen carbonate solution at room temperature, and the mixtures were extracted with ethyl acetate. The organic layers were washed with saturated brine, dried over anhydrous sodium sulfate, and concentrated under reduced pressure. The obtained residues were subjected to a silica gel column chromatography to obtain. the compound S-1 below 1.0 g.

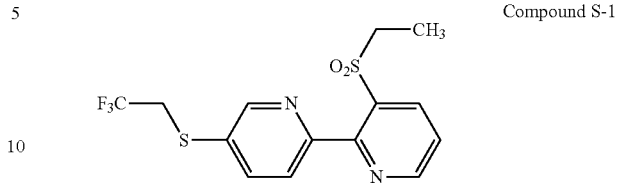

Compound S-1

$^1$H-NMR (CDCl$_3$) δ: 8.90-8.88 (1H, m), 8.70 (1H, d), 8.51-8.49 (1H, m), 7.98 (1H, dd), 7.83 (1H, d), 7.58 (1H, dd), 3.88 (2H, q) , 3.50 (2H, q) , 1.38 (3H, t).

Preparation Example 2

The compound S-4 below was prepared by using 2,2,3,3,-pentafluoropropyl trifluoromethane sulfonate instead of the compound 4 according to the similar method to that described in Preparation Example 1-4.

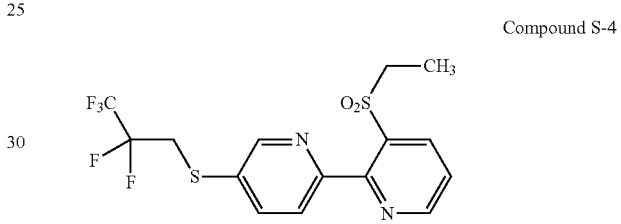

Compound S-4

$^1$H-NMR (CDCl$_3$) δ: 8.89 (1H, dd), 8.71 (1H, d), 8.50 (1H, dd), 7.98 (1H, dd), 7.83 (1H, dd), 7.58 (1H, dd), 3.88 (2H q), 3.50 (2H, t), 1.38 (3H, t).

Preparation Example 3

To a mixture of the compound S-1 680 mg and ethyl acetate 5 mL was added 70% mCPBA 700 mg under ice-cooling. The mixtures were stirred for twenty four hours under ice-cooling. To the resulting reaction mixtures were added saturated aqueous sodium hydrogen carbonate solution and aqueous sodium sulfite solution, and the mixtures were extracted with ethyl acetate. The organic layers were dried over anhydrous sodium sulfate, and concentrated under reduced pressure. The obtained residues were subjected to a silica gel column chromatography to obtain the compound S-2 below 410 mg and the compound S-3 below 250 mg.

The compounds that were prepared by the similar method to Preparation Example 3 and their physical property values are shown below.

Compound represented by formula (400):

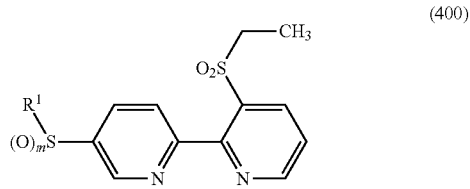

(400)

wherein R¹ and m represent any combination indicated in Table 18.

TABLE 18

| Compound | R¹ | m |
|---|---|---|
| S-2 | CF₃CH₂ | 1 |
| S-3 | CF₃CH₂ | 2 |
| S-5 | CF₃CF₂CH₂ | 1 |
| S-6 | CF₃CF₂CH₂ | 2 |

Compound S-2
¹H-NMR (CDCl₃) δ: 8.94-8.89 (2H, m), 8.52 (1H, dd), 8.23 (1H, dd), 8.06 (1H, dd), 7.63 (1H, dd), 3.86 (2H, q), 3.79-3.53 (2H, m), 1.40 (3H, t).
Compound S-3
¹H-NMR (CDCl₃) δ: 9.16 (1H, d), 8.93 (1H, dd), 8.52 (1H, dd), 8.41 (1H, dd), 8.08 (1H, d), 7.66 (1H, dd), 4.03 (2H, q), 3.85 (2H, q), 1.40 (3H, t).
Compound S-b 5
¹-NMR (CDCl₃) δ: 8.93-8.91 (2H, m), 8.52 (1H, dd), 8.24 (1H, dd), 8.07 (1H, dd), 7.64 (1H, dd), 3,87 (2H, q), 3.74-3.59 (1H, m), 3.54-3.43 (1H, m), 1.40 (3H, t).
Compound 8-6
¹H-NMR (CDCl₃) δ: 9.19 (1H, d), 8.93 (1H, dd), 8.53 (1H, dd), 8.43 (1H, dd), 8.09 (1H, dd), 7.66 (1H, 3.94 (2H, t), 3.86 (2H, q), 1.41 (3, t).

Preparation Example 4

A mixture of the compound 3 1.0 g, tetrakis(dimethylamino)ethylene 1.2 mL and DMF 4 mL was stirred under trifluoroiodomethane under ice-cooling for three hours. To the resulting mixtures was added saturated aqueous sodium hydrogen carbonate solution, and the mixtures were extracted with ethyl acetate. The organic layers were washed with water, and dried over anhydrous sodium sulfate and concentrated under reduced pressure. The obtained residues were subjected to a silica gel column chromatography to obtain the compound S-7 below 930 mg.

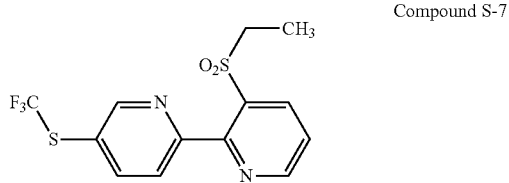 [SMILES: CCS(=O)(=O)c1cccnc1-c1ccc(SC(F)(F)F)cn1]

Compound S-7

¹H-NMR (CDCl₃) δ: 8.91 (1H, dd), 8.83 (1H, d), 8.51 (1H, dd), 8.17 (1H, dd), 7.92 (1H, dd), 7.61 (1H, dd), 3.88 (2H, q), 1.39 (3H, t).

The compounds that were prepared by the similar method to Preparation Example 4 and their physical property values are shown below.

Compound represented by formula (500):

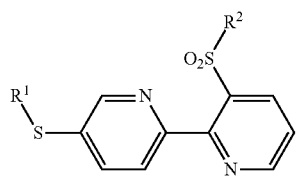

(500)

wherein R¹ and R² represent any combination indicated in Table 19.

TABLE 19

| Compound | R¹ | R² |
|---|---|---|
| S-10 | CF₃CF₂ | CH₃CH₂ |
| S-12 | CF₃CF₂CF₂ | CH₃CH₂ |
| S-13 | CF₃CF₂CF₂CF₂ | CH₃CH₂ |

Compound S-10
¹H-NMR (CDCl₃) δ: 8.91 (1H, dd), 8.82 (1H, d), 8.51 (1H, dd), 8.16 (1H, dd), 7.92 (1H, dd), 7.61 (1H, dd), 3.88 (2H, q), 1.39 (3H, t).
Compound S-12
¹H-NMR (CDCl₃) δ: 8.91 (1H, dd), 8.83 (1H, d), 8.51 (1H, dd), 8.17 (1H, dd), 7.92 (1H, dd), 7.61 (1H, dd), 3.88 (2H, q), 1.39 (3H, t).
Compound S-13
¹H-NMR (CDCl₃) δ: 8.91 (1H, dd), 8.83 (1H, d), 8.51 (1H, dd), 8.17 (1H, dd), 7.92 (1H, d), 7.61 (1H, dd), 3.88 (2H, q), 1.39 (3H, t).

Preparation Example 5

To a mixture of the compound S-7 720 mg and ethyl acetate 10 mL was added 70% mCPEA 770 mg under ice-cooling. The reaction mixtures were raised to room temperature, and stirred for twenty four hours. To the resulting mixtures were added saturated aqueous sodium hydrogen carbonate solation and aqueous sodium sulfite solution, and the mixtures were extracted with ethyl acetate. The organic layers were dried over anhydrous sodium sulfate and concentrated under reduced pressure. The obtained residues were subjected to a silica gel column chromatography to obtain the compound S-8 below 160 mg and the compound S-9 below 90 mg and the compound N-1 below 120 mg.

The compounds that were prepared by the similar method to Preparation Example 5 and their physical property values are shown below.

Compound represented by formula (600):

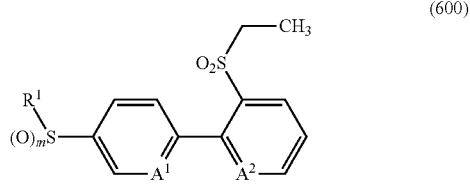

(600)

wherein R¹, A¹, A² and m represent any combination indicated in Table 20]

TABLE 20

| Compound | R¹ | m | A¹ | A² |
|---|---|---|---|---|
| S-8 | CF₃ | 1 | N | N |
| S-9 | CF₃ | 2 | N | N |
| S-11 | CF₃CF₂ | 1 | N | N |
| N-1 | CF₃ | 0 | N⁺—O⁻ | N |
| N-2 | CF₃CF₂ | 0 | N⁺—O⁻ | N |
| N-3 | CF₃CF₂ | 0 | N | N⁺—O⁻ |
| N-4 | CF₃CF₂ | 0 | N⁺—O⁻ | N⁺—O⁻ |

Compound S-8
¹H-NMR (CDCl₃) δ: 8.96 (1H, d), 8.93 (1H, dd), 8.53 (1H, dd), 8.32 (1H, dd), 8.09 (1H, dd), 7.65 (1H, dd), 3.87 (2H, q), 1.40 (3H, t).

Compound S-9
¹H-NMR (CDCl₃) δ: 9.20 (1H, d), 8.95 (1H, dd), 8.55-8.52 (1H, m), 8.50-8.47 (1H, m), 8.16-8.13 (1H, m), 7.68 (1H, dd), 3.86 (2H, q), 1.41 (3H, t).

Compound S-11
¹H-NMR (CDCl₃) δ: 8.97-8.92 (2H, m), 8.53 (1H, dd), 8.32 (1H, dd), 8.10 (1H, dd), 7.65 (1H, dd), 3.90-3.82 (2H, m), 1.40 (3H, t).

Compound N-1
¹H-NMR (CDCl₃) δ: 8.99-8.93 (1H, m), 8.49 (1H, d), 8.41-8.36 (1H, m), 7.73-7.60 (2H, m), 748 (1H, d), 3.74-3.52 (2H, m), 1.36 (3H, t).

Compound N-2
¹H-NMR (CDCl₃) δ: 8.97-8.94 (1H, m), 8.48 (1H, s), 8.39-8.36 (1H, m), 7.72-7.62 (2H, m), 7.48 (1H, dd), 3.74-3.48 (2H, m), 1.41-1.31 (3H, m).

Compound N-3
¹H-NMR (CDCl₃) δ: 8.88 (1H, d), 8.52-8.49 (1H, m), 8.15 (1H, dd), 7.99-7.95 (1H, m), 7.76 (1H, dd), 7.54 (1H, dd), 3.49-3.42 (2H, m), 1.35-1.28 (3H, m).

Compound N-4
¹H-NMR (CDCl₃) δ: 8.55-8.51 (1H, m), 8.51-8.45 (1H, m), 7.93-7.87 (1H, m), 7.67-7.56 (2H, m), 7.53 (1H, dd), 3.35-3.19 (2H, m) 1.32-1.22 (3H, m).

Preparation Example 6-1

A mixture of 2-bromo-5-methoxypyridine 1.5 g, 3-fluoro-2-(tributylstannyl)pyridine 4.6 g, tetrakis triphenylphosphine palladium (0) 920 mg, copper(I) iodide 300 mg and anhydrous lithium chloride 500 mg and toluene 27 mL was heated under reflux with stirring for seven hours. The resulting reaction mixtures were stood to cool to room temperature, and aqueous sodium hydrogen carbonate solution was added thereto, and the mixtures were extracted with ethyl acetate. The organic layers were washed successively with water and saturated brine, and dried over anhydrous sodium sulfate, and the organic layers were concentrated under reduced pressure. The obtained residues were subjected to a silica gel column chromatography to obtain the compound 5 below 510 mg.

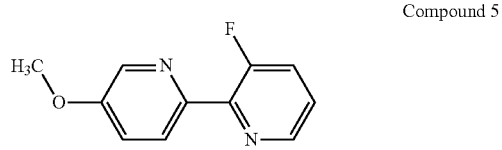

Compound 5

¹H-NMR (CDCl₃) δ: 8.57-8.54 (1H, m), 8.51-8.49 (1H, m), 7.96 (1H, dd), 7.56-7.49 (1H, m), 7.35-7.28 (2H, m), 3.94-3.91 (3H, m).

Preparation Example 6-2

To a mixture of the compound 5 510 mg, sodium hydride (oil, 60 %) 110 mg and DMF 5 mL was added dropwise ethanethiol 200 μL under ice-cooling. The mixtures were raised to room temperature and then stirred for four hours. To the resulting reaction mixtures was added saturated aqueous sodium hydrogen carbonate solution, and the mixtures were extracted with ethyl acetate. The organic layers were washed successively with water and saturated brine and concentrated under reduced pressure.

The obtained residues were diluted with chloroform, and thereto was added mCPBA (70 %) 1.4 g. The reaction mixtures were stirred at room temperature for ten hours. To the resulting reaction mixtures were added sodium sulfite and saturated aqueous sodium hydrogen carbonate solution successively, and then extracted with chloroform. The organic layers were washed with saturated sodium hydrogen carbonate and dried over anhydrous sodium sulfate, and the organic layers were concentrated under reduced pressure. The obtained residues were subjected to a silica gel column chromatography to obtain the compound 6 below 490 mg.

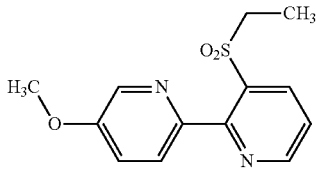

Compound 6

¹H-NMR (CDCl₃) δ: 8.86 (1H, dd), 8.48 (1H, dd, 8.31 (1H, d), 7.83 (1H, d), 7.51 (1H, dd) , 7.36 (1H, dd), 3.94-3.87 (5H, m), 1.37 (3H, t).

Preparation Example 6-3

To a 1.0 M boron tribromide dichloromethane solution 5 mL was added the compound 6 490 mg under ice-cooling. The mixtures were raised to room temperature, and stirred for two days. To the resulting reaction mixtures was added saturated aqueous sodium hydrogen carbonate solution under ice-cooling, and the mixtures were extracted with chloroform. The organic layers were washed successively with water and saturated brine and dried over anhydrous sodium sulfate, and the organic layers were concentrated under reduced pressure. The resulting residues were subjected to a silica gel column chromatography to obtain the compound 7 below 300 mg.

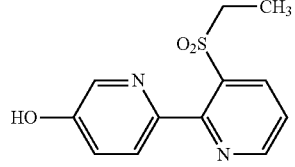

Compound 7

¹H-NMR (CDCl₃) δ: 8.86 (1H, dd), 8.50 (1H, dd), 8.12 (1H, d), 7.67 (1H, d), 7.54 (1H, dd), 7.08 (1H, dd), 6.64 (1H, br s), 3.94 (2H, q), 1.39 (3H, t).

Preparation Example 6-4

To a mixture of the compound 7 300 mg, 2,6-lutidine 240 mg, and chloroform 4 mL was added trifluoromethanesulfonic anhydride 380 mg under ice-cooling. The reaction mixtures were stirred under ice-cooling for ten minutes. To the resulting reaction mixtures was added saturated aqueous sodium hydrogen carbonate solution, and the mixtures were extracted with chloroform. The organic layers were dried over anhydrous sodium hydrate, and concentrated under reduced pressure. The obtained residues were subjected to a silica gel column chromatography to obtain the compound O-1 below 430 mg.

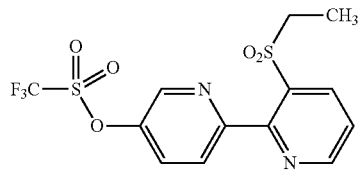

Compound O-1

$^1$H-NMR (CDCl$_3$) δ: 8.90 (1H, dd), 8.61 (1H, d), 8.51 (1H, dd), 7.97 (1H, d) 7.81 (1H, dd), 7.61 (1H, dd), 3.84 (2H, q), 1.39 (3H, t).

Preparation Example 7

The compound O-2 was prepared by using 2,2,2-trifluoroethane sulfonic chloride instead of trifluoromethanesulfonic anhydride according to a similar method to that described in Preparation Example 6-4.

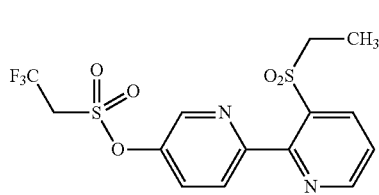

Compound O-2

$^1$H-NMR (CDCl$_3$) δ: 8.90 (1H, dd), 8.60 (1H, d), 8.51 (1H, dd), 7.96 (1H, d), 7.83 (1H, dd), 7.60 (1H, dd), 4.17-4.08 (2H, m), 3.86 (2H, q), 1.38 (3H, t).

A compound represented by formula (204):

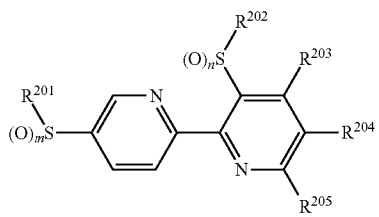

(204)

[wherein $R^{201}$, $R^{202}$, $R^{203}$, $R^{204}$, $R^{205}$, n and m represent any combination indicated in Table 21 to Table 23 below.] may be prepared according to the above-mentioned method.

TABLE 21

| Compound A | $R^{201}$ | n | m | $R^{203}$ | $R^{204}$ | $R^{205}$ |
|---|---|---|---|---|---|---|
| S-12 | CF$_2$H | 2 | 0 | H | H | H |
| S-13 | CF$_2$HCH$_2$ | 2 | 0 | H | H | H |
| S-14 | CF$_3$CH$_2$ | 2 | 0 | H | H | H |
| S-15 | CCl$_3$CH2 | 2 | 0 | H | H | H |
| S-16 | CF$_2$HCF$_2$ | 2 | 0 | H | H | H |
| S-17 | CClFHCF$_2$ | 2 | 0 | H | H | H |
| S-18 | CF$_3$CH$_2$CH$_2$ | 2 | 0 | H | H | H |
| S-19 | CF$_2$HCF$_2$CH$_2$ | 2 | 0 | H | H | H |
| S-21 | CF$_3$CFHCF$_2$ | 2 | 0 | H | H | H |

TABLE 21-continued

| Compound A | $R^{201}$ | n | m | $R^{203}$ | $R^{204}$ | $R^{205}$ |
|---|---|---|---|---|---|---|
| S-22 | CF$_3$CFHCF$_2$ | 2 | 1 | H | H | H |
| S-23 | CF$_3$CFHCF$_2$ | 2 | 2 | H | H | H |
| S-24 | CH$_3$CH$_2$CH$_2$ | 2 | 0 | H | H | H |
| S-25 | C(CF$_3$)$_2$(CH$_3$)CH$_2$ | 2 | 0 | H | H | H |
| S-26 | CF$_3$CFHCF$_2$CH$_2$ | 2 | 0 | H | H | H |
| S-26 | CF$_3$CFHCF$_2$CH$_2$ | 2 | 1 | H | H | H |
| S-26 | CF$_3$CFHCF$_2$CH$_2$ | 2 | 2 | H | H | H |
| S-27 | CF$_3$CF$_2$CF$_2$CH$_2$ | 2 | 0 | H | H | H |
| S-28 | CF$_3$CF$_2$CF$_2$CF$_2$CH$_2$ | 2 | 0 | H | H | H |
| S-29 | CF$_3$CF$_2$CF$_2$CF$_2$CF$_2$CH$_2$ | 2 | 0 | H | H | H |
| S-30 | CF$_3$CF$_2$CF$_2$CF$_2$CH$_2$CH$_2$ | 2 | 0 | H | H | H |
| S-31 | CF(CF$_3$)$_2$CF$_2$CF$_2$CH$_2$CH$_2$ | 2 | 0 | H | H | H |
| S-32 | CF$_2$HCF$_2$CF$_2$CF$_2$CH$_2$ | 2 | 0 | H | H | H |
| S-33 | CF$_2$HCF$_2$CF$_2$CF$_2$CF$_2$CF$_2$CH$_2$ | 2 | 0 | H | H | H |
| S-34 | CF$_3$OCFHCF$_2$ | 2 | 0 | H | H | H |
| S-35 | CF$_3$OCFHCF$_2$ | 2 | 1 | H | H | H |

TABLE 22

| Compound A | $R^{201}$ | n | m | $R^{203}$ | $R^{204}$ | $R^{205}$ |
|---|---|---|---|---|---|---|
| S-36 | CF$_3$OCFHCF$_2$ | 2 | 2 | H | H | H |
| S-37 | CF$_3$CH$_2$OCH$_2$CH$_2$ | 2 | 0 | H | H | H |
| S-41 | CF$_2$H | 2 | 0 | H | CF$_3$ | H |
| S-42 | CF$_3$ | 2 | 0 | H | CF$_3$ | H |
| S-43 | CF$_2$HCH$_2$ | 2 | 0 | H | CF$_3$ | H |
| S-44 | CCl$_3$CH$_2$ | 2 | 0 | H | CF$_3$ | H |
| S-45 | CF$_2$HCF$_2$ | 2 | 0 | H | CF$_3$ | H |
| S-46 | CClFHCF$_2$ | 2 | 0 | H | CF$_3$ | H |
| S-47 | CF$_3$CF$_2$ | 2 | 0 | H | CF$_3$ | H |
| S-48 | CF$_3$CH$_2$CH$_2$ | 2 | 0 | H | CF$_3$ | H |
| S-49 | CF$_2$HCF$_2$CH$_2$ | 2 | 0 | H | CF$_3$ | H |
| S-50 | CF$_3$CFHCF$_2$ | 2 | 0 | H | CF$_3$ | H |
| S-51 | CF$_3$CF$_2$CF$_2$ | 2 | 0 | H | CF$_3$ | H |
| S-52 | CF$_3$CF$_2$CF$_2$ | 2 | 1 | H | CF$_3$ | H |
| S-53 | CF$_3$CF$_2$CF$_2$ | 2 | 2 | H | CF$_3$ | H |
| S-54 | C(CF$_3$)$_2$(CH$_3$)CH$_2$ | 2 | 0 | H | CF$_3$ | H |
| S-55 | CF$_3$CFHCF$_2$CH$_2$ | 2 | 0 | H | CF$_3$ | H |
| S-56 | CF$_3$CFHCF$_2$CH$_2$ | 2 | 1 | H | CF$_3$ | H |
| S-57 | CF$_3$CFHCF$_2$CH$_2$ | 2 | 2 | H | CF$_3$ | H |

TABLE 23

| Compound A | $R^{201}$ | n | m | $R^{203}$ | $R^{204}$ | $R^{205}$ |
|---|---|---|---|---|---|---|
| S-58 | CF$_3$CF$_2$CF$_2$CF$_2$ | 2 | 0 | H | CF$_3$ | H |
| S-59 | CF$_3$CF$_2$CF$_2$CF$_2$ | 2 | 1 | H | CF$_3$ | H |
| S-60 | CF$_3$CF$_2$CF$_2$ | 2 | 2 | H | CF$_3$ | H |
| S-61 | CF$_3$CF$_2$CF$_2$CF$_2$CH$_2$ | 2 | 0 | H | CF$_3$ | H |
| S-62 | CF$_3$CF$_2$CF$_2$CF$_2$CH$_2$CH$_2$ | 2 | 0 | H | CF$_3$ | H |
| S-63 | CF$_3$CF$_2$CF$_2$CF$_2$CH$_2$CH$_2$ | 2 | 0 | H | CF$_3$ | H |
| S-64 | CF(CF$_3$)$_2$CF$_2$CF$_2$CH$_2$CH$_2$ | 2 | 0 | H | CF$_3$ | H |
| S-65 | CF$_2$HCF$_2$CF$_2$CF$_2$CH$_2$ | 2 | 0 | H | CF$_3$ | H |
| S-66 | CF$_2$HCF$_2$CF$_2$CF$_2$CF$_2$CF$_2$CH$_2$ | 2 | 0 | H | CF$_3$ | H |
| S-67 | CF$_3$OCFHCF$_2$ | 2 | 0 | H | CF$_3$ | H |
| S-68 | CF$_3$OCFHCF$_2$ | 2 | 1 | H | CF$_3$ | H |
| S-69 | CF$_3$OCFHCF$_2$ | 2 | 2 | H | CF$_3$ | H |
| S-70 | CF$_3$CH$_2$OCH$_2$CH$_2$ | 2 | 0 | H | CF$_3$ | H |

A compound represented by formula (301):

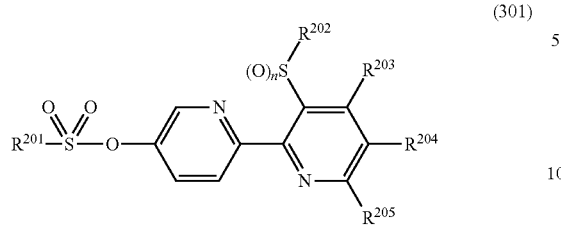

[wherein, $R^{201}$, $R^{202}$, $R^{203}$, $R^{204}$, $R^{205}$, and n represent any combination indicated in Table 24 to Table 25 below.]

may be prepared according the similar method to hose described above.

TABLE 24

| Compound A | $R^{201}$ | n | $R^{203}$ | $R^{204}$ | $R^{205}$ |
|---|---|---|---|---|---|
| O-3 | $CF_2H$ | 2 | H | H | H |
| O-4 | $CF_2HCH_2$ | 2 | H | H | H |
| O-5 | $CF_2HCF_2$ | 2 | H | H | H |
| O-6 | $CF_3CF_2$ | 2 | H | H | H |
| O-7 | $CF_3CF_2CF_2$ | 2 | H | H | H |
| O-8 | $CF_3CF_2CF_2CF_2$ | 2 | H | H | H |
| O-9 | $CF_3CF_2CF_2CF_2CF_2$ | 2 | H | H | H |

TABLE 25

| Compound A | $R^{201}$ | n | $R^{203}$ | $R^{204}$ | $R^{205}$ |
|---|---|---|---|---|---|
| O-10 | $CF_2H$ | 2 | H | $CF_3$ | H |
| O-11 | $CF_2HCH_2$ | 2 | H | $CF_3$ | H |
| O-12 | $CF_2HCF_2$ | 2 | H | $CF_3$ | H |
| O-13 | $CF_3CF_2$ | 2 | H | $CF_3$ | H |
| O-14 | $CF_3CF_2CF_2$ | 2 | H | $CF_3$ | H |
| O-15 | $CF_3CF_2CF_2CF_2$ | 2 | H | $CF_3$ | H |
| O-16 | $CF_2CF_2CF_2CF_2CF_2$ | 2 | H | $CF_3$ | H |

Next, the formulation examples of the compound A are shown below. The "parts" represents "part by weight" unless otherwise specified.

Formulation Example 1

Into a mixture of 35 parts of xylene and 35 parts of DMF, 10 parts of any one of the compounds S-1 to S-70, N-1 to N-4, and O-1 to O-16 is mixed, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of synthetic hydrated silicon oxide fine powder and 54 parts of diatomaceous earth are mixed, and further 20 parts of any one of the compounds S-1 to S-70, N-1 to N-4, and O-1 to O-16 is added, followed by mixing them to obtain each wettable powders.

Formulation Example 3

To 2 parts of any one of the compounds S-1 to S-70, N-1 to N-4, and O-1 to O-16, 1 part of synthetic hydrated silicon oxide fine powder, 2 parts of lignin sulfonate, 30 parts of bentonite and 65 parts of kaolin clay are added, followed by mixing, granulation with granulator and forced-air drying to obtain each granular formulation.

Formulation Example 4

Into an appropriate amount of acetone, 1 part of any one of the compounds S-1 to S-70, N-1 to N-4, and O-1 to O-16 is mixed, and then 5 parts of synthetic hydrous silicon oxide fine powder, 0.3 parts of isopropyl acid phosphate and 93.7 parts of kaolin clay are added, followed by mixing stirring thoroughly and removal of acetone from the mixture by evaporation to obtain each of powder formulation.

Formulation Example 5

A mixture of 35 parts of polyoxyethylene alkyl ether sulfate ammonium salt and white carbon (weight ratio of 1:1), 10 parts of any one of the compounds S-1 to S-70, N-1 to N-4, and O-1 to O-16, and 55 parts of water are mixed, followed by finely grounding by a wet grinding method to obtain each flowable formulation.

Formulation Example 6

Into a mixture of 5 parts of xylene and 5 parts of trichloroethane, 0.1 parts of any one of the compounds S-1 to S-70, N-1 to N-4, and O-1 to O-16 is dissolved, and the resulting mixture is then mixed with 89.9 parts of kerosene to obtain each oil solution.

Formulation Example 7

Into 0.5 mL of acetone, 10 mg of any one of the compounds S-1 to S-70, N-1 to N-4, and O-1 to O-16 is dissolved and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of any one of the compounds S-1 to S-70, N-1 to N-4, and O-1 to O-16 and. 49.9 parts of Neothiozole (Chuo Kasei Co., Ltd.) are placed. After mounting an aerosol valve, 25 parts of dimethyl ether and 25 parts of LPG are filled, followed by shaking and further mounting an actuator to obtain an oily aerosol.

Formulation Example 9

A mixture of 0.6 part of any one of the compounds S-1 to S-70, N-1 to N-4, and O-1 to O-16, 0.01 part of BHT (2,6-di-tert-butyl-4-methylphenol), 5 parts of xylene, 3.39 parts of deodorized kerosine and 1 part of an emulsifier {Rheodol MO-60 (registered trademark of Kao Corporation)} and 50 parts of distilled water are filled into an aerosol container, and a valve part is attached. Then, 40 parts of a propellant (LPG) is filled therein through the valve under pressure to obtain an aqueous aerosol.

Formulation Example 10

Zero point one (0.1) parts of any one of the compounds S-1 to S-70, N-1 to N-4, and O-1 to O-16 are mixed into 2 mL of propylene glycol, and the resulting solution is impregnated into a ceramic plate having a size of 4.0 cm×4.0 cm and a thickness of 1.2 cm, to obtain thermal fumigants.

Formulation Example 11

Five (5) parts of any one of the compounds S-1 to S-70, N-1 to N-4, and O-1 to O-16, and 95 parts of ethylene-methyl methacrylate copolymer (the ratio of the methyl methacrylate in the copolymer: 10 weight %), Acryft (registered by trademark) WD 301, manufactured by Sumitomo Chemical Co. Ltd.) are melted and kneaded with a closed type pressure kneader, and the resulting kneaded product is extruded from an extrusion molding machine through a molding die to obtain a rod-shaped molded product having a length of 15 cm and a diameter of 3 mm.

Formulation Example 12

Five (5) parts of any one of the compounds S-1 to S-70, N-1 to N-4, and O-1 to O-16, and 95 parts of plasticized polyvinyl chloride resin are melted and kneaded with a closed type pressure kneader, and the resulting kneaded product is extruded from an extrusion molding machine through a molding die to obtain a rod-shaped molded product having a length of 15 cm and a diameter of 3 mm.

Formulation Example 13

One hundred (100) mg of any one of the compounds S-1 to S-70, N-1 to N-4, and O-1 to O-16, 68.75 mg of lactose, 237.5 mg of corn starch, 43.75 mg of microcrystalline cellulose, 18.75 mg of polyvinylpyrrolidone, 28.75 mg of sodium carbomethyl starch and 25 mg of magnesium stearate are mixed, and the resulting mixture was compressed to an appropriate size to obtain a tablet.

Formulation Example 14

Twenty five (25) mg of any one of the compounds S-1 to S-70, N-1 to N-4, and O-1 to O-16, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain capsules.

Formulation Example 15

To 100 mg of any one of the compounds S-1 to S-70, N-1 to N-4, and O-1 to O-16, 500 mg of fumaric acid 2,000 mg of granulated sugar, 13,000 mg of sorbitol (70% solution), 100 mg of Veegum K (manufactured by Vanderbilt. Co.), 35 mg of perfume and 500 mg of coloring agent, a distilled water is added so that a final volume is set to be 100 mL, followed by mixing them to obtain a suspension for oral administration.

Formulation Example 16

Into a mixture of 5% by weight of an emulsifier, 3% by weight of benzyl alcohol and 30% by weight of propylene glycol, 5% by weight of any one of the compounds S-1 to S-70, N-1 to N-4, and O-1 to O-16 is dissolved, and phosphate buffer is added thereto so that a pH of the solution is set to be 6.0 to 6.5, and water is added as the rest parts to obtain the solution for oral administration.

Formulation Example 17

To a mixture of 57% by weight of fractional distillated palm oil and 3% by weight of polysorbate 85, 5% by weight of aluminum distearate is added, and heated to disperse it. The resulting mixture is cooled to room temperature, and 25% by weight of saccharin is dispersed in an oil vehicle. Ten (10) % by weight of any one of the compounds S-1 to S-70, N-1 to N-4, and O-1 to O-16 is divided thereto to obtain a paste for oral administration.

Formulation Example 18

Five (5) % by weight of any one of the compounds S-1 to S-70, N-1 to N-4, and O-1 to O-16 is mixed with 95% by weight of limestone filler, followed by a wet granulation of the resulting mixture to obtain a granule for oral administration.

Formulation Example 19

Into 80 parts of diethylene glycol monomethyl ether, 5 parts of any one of compounds S-1 to S-70, N-1 to N-4, and O-1 to O-16 is dissolved, and 15 parts of propylene carbonate is added thereto, and the resulting mixture is mixed to obtain a spot-on solution.

Formulation Example 20

Into 70 parts of diethylene glycol monomethyl ether, 10 parts of any one of the compounds S-1 to S-70, N-1 to N-4, and O-1 to O-16 is dissolved, and 20 parts of 2-octyldodecanol is added thereto, and the resulting mixture is mixed to obtain a pour-on solution.

Formulation Example 21

To 0.5 parts of any one of the compounds S-1 to S-70, N-1 to N-4, and O-1 to O-16, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain ahydrogenous solution of shampoo formulation.

Formulation Example 22

Zero point fifteen (0.15)% by weight of any one of the compounds to S-70, N-1 to N-4, and O-1 to O-16, 95% by weight of animal feed, as well as 4.85% by weight of a mixture of dibasic calcium phosphate, diatomaceous earth, aerosol and carbonate (or chalk) are mixed with stirring thoroughly to obtain a premix for animal feed.

Formulation Example 23

Seven point two (7.2) g of any one of the compounds S-1 to S-70, N-1 to N-4, and O-1 to O-16, and 92.8 of Hosco (registered trademark) S-55 (manufactured by Maruishi Pharmaceuticals) are melted and mixed at 100° C., and the resulting mixture was poured into a suppository mold, followed by performing a cooling solidification to obtain a suppository.

Next, Test Examples are used to show an efficacy of the compound A on controlling harmful arthropods.

Test Example 1

Each of the compounds S-1, S-2, S-3, S-4, S-5, S-6, S-7, S-8, S-9, S-10, N-1, N-4, O-1 and O-2 was made to a formulation according to a similar method to that described in the Formulation Example 5 and was then diluted with water so that the active ingredient concentration was set to 500 ppm to prepare each of the diluted solution.

Cucumber seedling (on the developmental stage of the first true leaf) was planted a polyethylene cup and 30 heads of cotton aphid (Aphis gossypii) (all stages of life) were released onto the leaves of the cucumber and allowed to stand for 1 day. The diluted solutions 20 mL were sprayed into the seedling.

Cucumber (cv; *Sagami-hanjiro-fushinari*) was grown in a polyethylene cup until the first true leaf was developed. Approximately 30 heads of cotton aphid (Aphis gossypii) (including the adults and the larvae) was released onto the leaves of the cabbage and next day, the above-mentioned testing drug dilutions 20 mL were sprayed.

After 6 days, the number of the surviving insects that were parasitic on the leaves of the cucumber was examined and the controlling value was calculated by the following equation.

Controlling value (%)={1−(Cb×Tai)/(Cai×Tb)}×100 wherein the symbols in the formula represent the following descriptions.

Cb: Number of the insects before treatment in untreated area;

Cai: Number of the surviving parasitic insects at the time of the investigation untreated area;

Tb: Number of the insects before treatment in treated area;

Tai: Number of the surviving parasitic insects at the time of the investigation in treated area;

Here the "untreated area" represents an area that was sprayed by a diluted solution of the formulation described in the Formulation Example 5 with out the compound A with water in the same amount as that of the treated area.

As a result, the treated area that was treated with each of the diluted solutions of the compounds S-1, S-2, S-3, S-4, S-5, S-6, S-7, S-8, S-9, S-10, N-1, N-4, O-1 and O-2 respectively showed 90% or greater as the controlling value.

Test Example 2

Each of the compounds S-1, S-2, S-7, S-8, S-9, S-10, N-1, O-1 and O-2 was made to a formulation according to a similar method to that described in the Formulation example 5 and was then diluted with water so that each of the active ingredient concentration was set to 200 ppm to prepare each of the diluted solution.

Cucumber seedling (on the developmental stage of the first true leaf) was planted in a polyethylene cup and 30 heads of cotton aphid (Aphis gossypii) (all stages of life) were released onto the leaves of the cucumber and allowed to stand for 1 day. The diluted solutions 20 mL were sprayed into the seedling.

Cucumber (cv; *Sagami-hanjiro-fushinari*) was grown in a polyethylene cup until the first true leaf was developed. Approximately 30 heads of cotton aphid (Aphis gossypii) (including the adults and the larvae) was released onto the leaves of the cabbage and next day, the above-mentioned testing drug dilutions 20 mL were sprayed.

After 6 days, the number of the surviving insects that were parasitic on the leaves of the cucumber was examined and the controlling value was calculated by the following equation.

Controlling value (%)={1−(Cb×Tai)/(Cai×Tb)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

Here the "untreated area" represents an area that was sprayed by a diluted solution of the formulation described in the Formulation Example 5 without the compound A with water in the same amount as that of the treated area.

As a result, the treated area that was treated with each of the diluted solutions of the compounds S-1, S-2, S-7, S-8, S-9, S-10, N-1, O-1 and O-2 respectively showed 90% or greater as the controlling value.

Test Example 3

Each of the S-1, S-2, S-7, S-8, S-9, S-10, N-1, and O-2 was made to a formulation according to a similar method to that described in the Formulation example 5 and was then diluted with water so that the active ingredient concentration was set to 200 ppm to prepare the diluted solution.

Cucumber seedling (on the developmental stage of the second true leaf) was planted in a polyethylene cup, and the diluted solutions 5 mL were irrigated into the plant foot, and the plants were held at 25° C. in a greenhouse for 7 days. Approximately 30 heads of cotton aphid (*Aphis gossypii*) (all stages of life) were inoculated onto the cucumber leaves and the plants were held in a greenhouse for additional 6 days, and then the number of the surviving nsects that were parasitic on the cucumber leaves was examined and the controlling value was calculated by the following equation.

Controlling value (%)={1−(Cb×Tai)/(Cai×Tb)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

Here the "untreated area" represents an area that was sprayed by a diluted solution of the formulation described in the Formulation Example 5 without the compound A with water in the same amount as that of the treated area.

As a result, the treated area that was treated with each of the diluted solutions of the compounds S-1, S-2, S-7, S-8, S-9, S-10, N-1, O-1 and O-2 respectively showed 90% or greater as the controlling value.

Test Example 4

Each of the compounds S-1, S-2, S-7, S-8, S-9, S-10, N-1, and O-2 was made to a formulation according to a similar method to that described in the Formulation example 5 and was then diluted with water so that each of the active ingredient concentration was set to 500 ppm to prepare each of the diluted solution.

Rice seedling (on the developmental stage of the second true leaf) was planted in a polyethylene cup, and the diluted solutions 10 mL were sprayed. After air drying, 20 heads of 3rd to 4th instar larvae of brown planthopper (*Nilaparvata lugens*) were released onto the rice leaves and the plants were held at 25° C. in a greenhouse.

After 6 days, the number of the surviving insects that were parasitic on the leaves of the rice was examined and the controlling value was calculated by the following equation.

Controlling value (%)={1−(Cb×Tai)/(Cai×Tb)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

Here the "untreated area" represents an area that was sprayed by a diluted solution of the formulation described in the Formulation Example 5 without the compound A with water in the same amount as that of the treated area.

As a result, the treated area that was treated with each of the diluted solutions of the compounds S-1, S-2, S-7, S-8, S-9, S-10, N-1, and O-2 respectively showed 90% or greater as the controlling value.

Test Example 5

Each of the compounds S-1, S-2, S-7, S-8, S-9, S-10, N-1, and O-2 was made to a formulation according to a similar method to that described in the Formulation example 5 and was then diluted with water so that each of the active ingredient concentration was set to 200 ppm to prepare each of the diluted solution.

Rice seedling (on the developmental stage of the second true leaf) was planted in a polyethylene cup, and the diluted solutions 10 mL were sprayed. After air drying, 20 heads of 3rd to 4th instar larvae of brown planthopper (*Nilaparvata lugens*) were released onto the rice leaves and the plants were held at 25° C. in a greenhouse.

After 6 days, the number of the surviving insects that were parasitic on the leaves of the rice was examined and the controlling value was calculated by the following equation.

Controlling value (%)={1−(Cb×Tai)/(Cai×Tb)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

Here the "untreated area" represents an area that was sprayed by a diluted solution of the formulation described in the Formulation Example 5 without the compound A with water in the same amount as that of the treated area.

As a result, the treated area that was treated with each of the diluted solutions of the compounds S-1, S-2, S-7, S-8, S-9, S-10, N-1, and O-2 respectively showed 90% or greater as the controlling value.

Test Example 6

Each of the compounds S-7, S-8, S-9, S-10, N-1, and O-2 was made to a formulation according to a similar method to that described in the Formulation example 5 and was then diluted with water so that each of the active ingredient concentration was set to 200 ppm to prepare each of the diluted solution.

Rice seedling (two weeks after sowing, on the developmental stage of the second true leaf) was planted in a polyethylene cup, and the diluted solutions 5 mL were irrigated into the plant foot, and the plants were held at 25° C. in a greenhouse for 7 days. Twenty (20) heads of 3rd to 4th instar larvae of brown planthopper (*Nilaparvata lugens*) were released onto the rice leaves and the plants were held at 25° C. in a greenhouse for additional 6 days, and then the number of the surviving insects that were parasitic on rice leaves was examined and the controlling value was calculated by the following equation.

Controlling value (%)={1−(Cb×Tai)/(Cai×Tb)}×100 wherein the symbols in the formula represent the following descriptions.

Cb: Number of the insects before irrigation in untreated area;

Cai: Number of the surviving parasitic insects at the time of the investigation in untreated area;

Tb: Number of the insects before irrigation in treated area;

Tai: Number of the surviving parasitic insects at the time of the investigation in treated area;

Here the "untreated area" represents an area that was sprayed by a diluted solution of the formulation described in the Formulation Example 5 without the compound A with water in the same amount as that of the treated area.

As a result, the treated area that was treated with each of the diluted solutions containing the compounds S-7, S-8, S-9, S-10, N-1, and O-2 respectively showed 90% or greater as the controlling value.

Test Example 7

Each of the compounds S-1, S-5, S-7, S-8, S-9, S-10, O-1, and O-2 was made to a formulation according to a similar method to that described in the Formulation example 5 and was then diluted with water so that each of the active ingredient concentration was set to 500 ppm to prepare each of the diluted solution.

A cabbage in the third leaf stage was planted in a polyethylene cup, and thereto was sprayed the diluted solution in ratio 20 mL/cup. After the above-mentioned dilutions were dried, and the stem and leaf thereof was cut and then was stalled in a 50 mL cup, and five heads of cabbage moth (*Plutella xylostella*) at the second instar larval stages were released into the cup and the cup was covered with the lid. The cup was held at 25° C. and after 5 days, the number of died insects was counted and the mortality of insects was calculated by the following equation.

Mortality of insects (%)=(Number of dead insects/ Number of tested insects)×100

As a result, the treated area that was treated with each of the diluted solutions of the compounds S-1, S-5, S-7, S-8, S-9, S-10, O-1, and O-2 respectively showed 80% or greater as the mortality of insects.

Test Example 8

Each of the compounds S-7, S-8, S-9, S-10, and O-2 was made to a formulation according to a similar method to that described in the Formulation example 5 and was then diluted with water so that each of the active ingredient concentration was set to 200 ppm to prepare each of the diluted solution.

A cabbage in the third leaf stage was planted in a polyethylene cup, and thereto was sprayed the diluted solution in a ratio of 20 mL/cup. After the above-mentioned dilutions were dried, and the stem and leaf thereof was cut and then was installed in a 50 mL cup, and five heads of cabbage moth (*Plutella xylostella*) at the second instar larval stages were released into the cup and the cup was covered with the lid. The cup was held at 25° C. and after 5 days, the number of died insects was counted and the mortality insects was calculated by the following equation.

Mortality of insects (%)=(Number of dead insects/ Number of tested insects)×100

As a result, the treated area that was treated with each of the diluted solutions of the compounds S-7, S-8, S-9, S-10, and O-2 respectively showed 80% or greater as the mortality of insects.

Test Example 9

Each of the compounds S-2, S-3, S-7, S-8, and N-1 was made to a formulation according to a similar method to that described in the Formulation example 5 and was then diluted with water so that each of the active ingredient concentration was set to 500 ppm to prepare each of the diluted solution.

The bottom of the polyethylene cup having 5.5 cm diameter was matted with the same size of a filter paper, and 0.7 mL of the diluted solution was added dropwise to the filter paper and 30 mg sucrose as bait was placed in the cup uniformly. Ten (10) heads of female adult housefly (*Musca domestica*) were released into the polyethylene cup and the cup was covered with the lid. After 24 hours, the life and death of housefly was examined and the number of died insects was counted and the mortality of insects was calculated by the following equation.

Mortality of insects (%)=(Number of dead insects/ Number of tested insects)×100

As a result, the treated area that was treated with each of the diluted solutions of the compounds S-2, S-3, S-7, S-8, and N-1 respectively showed 100% as the mortality of insects.

Test Example 10

The compound S-1 was mixed with a mixed solution of acetone and polyoxyethylene sorbitan mono-cocoate (acetone and polyoxyethylene sorbitan mono-cocoate=95 : 5 (weight ratio)) a ratio of 50 μL of the mixed solution per 1 mg of the compound S-1, and the resulting mixtures were then diluted with ion-exchange water containing 0.03% by volume of shindain (registered trademark, manufactured by Sumitomo Chemical Co. Ltd.) so that the concentration of the compound S-1 was set to 500 ppm to prepare the diluted solution of the compound S-1.

Corns (Xea mays) were sown on a tray overlaid with damped KimWipes (registered trademark). After corns were grown for 5 days, the entire seedling of the corn was immersed into the diluted solution for 30 seconds. After the seedling was dried, two grains of the seedling were installed in a plastic petri dish (90 mm radius), and ten heads of western corn rootworm (*Diabrotica virgifera virgifera*) at the second instar larval stages were released onto the petri dish and the petri dish was covered with the lid. The petri dish was held at 25° C. and after 5 days, the number of died insects was counted and the mortality of insects was calculated by the following equation.

Mortality of insects (%)=(Number of dead insects/ Number of tested insects)×100

Similarly, using the compounds S-2, S-3, S-7, S-10, O-1 and O-2 instead of the compound S-1, the tests were carried out.

As a result, the compounds S-2, S-3, S-4, S-7, S-10, O-1 and O-2 respectively showed 80% or greater as the mortality of insects.

Next, each efficacy against a harmful arthropod of the compound A and the compounds described n JP 2000-26421 A respectively is shown in the below-mentioned comparative experiment.

Comparative Experiment

The comparative experiments were conducted by using the compounds S-1, S-7 and S-8 as the compound A, and the below-mentioned compounds V-7, V-11 and V-12 as the compounds described in JP 2000-26421 A. The results are shown in Table 26. In the Table, each of the Comparative Experiment 2 the Comparative Experiment 3, and the Comparative Experiment 5 represents a comparative experiment that was conducted according to the similar method to that described in Test Example 2, Test Example 3, and Test Example 5, respectively. Here A represents 100%, B represents 90 to 99%, C represents 60 to 89%, D represents 30 to 59% and represents 0 to 29% as a control value.

TABLE 26

| Compound | Comparative Experiment 2 | Comparative Experiment 3 | Comparative Experiment 5 |
|---|---|---|---|
| 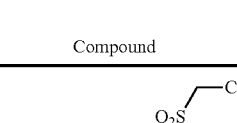 S-1 | A | B | A |
| 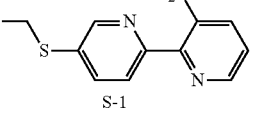 S-7 | A | A | A |

TABLE 26-continued

| Compound | Comparative Experiment 2 | Comparative Experiment 3 | Comparative Experiment 5 |
|---|---|---|---|
| S-8 | A | A | A |
| V-7 | E | E | D |
| V-11 | E | E | E |
| V-12 | E | E | E |

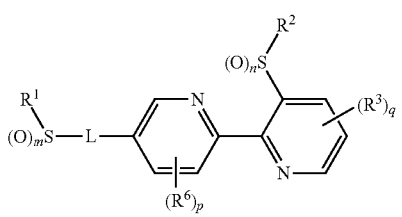

Industrial Applicability

The compound A shows an excellent control effect against a harmful arthropod.

The invention claimed is:

1. A bipyridine compound represented by formula (I) or an N-oxide thereof:

(I)

wherein:

L represents a single bond or an oxygen atom, and when L represents an oxygen atom, m represents 2;

$R^1$ represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, or a C3-C7 cycloalkyl group substituted with one or more substituents selected from Group G;

$R^2$ represents a C1-C6 alkyl group optionally substituted with one or more halogen atoms;

$R^3$ represents a C1-C6 chain hydrocarbon group optionally substituted with one or more substituents selected from Group B, a phenyl group optionally substituted with one or more substituents selected from Group D, a 5 or 6 membered aromatic heterocyclic group optionally substituted with one or more substituents selected from Group D, a $OR^{12}$, a $NR^{11}R^{12}$, a $NR^{11a}R^{12a}$, a $NR^{24}NR^{11}R^{12}$, a $NR^{11}C(O)R^{13}$, a $NR^{24}NR^{11}C(O)R^{13}$, a $NR^{11}C(O)OR^{14}$, a $NR^{24}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $S(O)_yR^{15}$, a $C(O)OR^{17}$, a $C(O)NR^{11}R^{12}$, a cyano group, a nitro group, or a halogen atom;

q is 0, 1, 2, or 3, and when q is 2 or 3, a plurality of $R^3$ may be identical or different;

$R^6$ represents a C1-C6 alkyl group optionally substituted with one or more halogen atoms, a $OR^{18}$, a $NR^{18}R^{19}$, a $C(O)OR^{25}$, a $OC(O)R^{20}$, a cyano group, a nitro group, or a halogen atom;

p is 0, 1, 2, or 3, and when p is 2 or 3, a plurality of $R^3$ can be identical or different;

$R^{11}$, $R^{17}$, $R^{18}$, $R^{19}$, $R^{20}$, $R^{24}$ and $R^{25}$ represent independently of each other a hydrogen atom, or a C1-C6 chain hydrocarbon group optionally substituted with one or more halogen atoms;

$R^{12}$ represents a hydrogen atom, a C1-C6 chain hydrocarbon group optionally substituted with one or more halogen atoms, a C1-C6 alkyl group substituted with one substituent selected from Group F, or a $S(O)_2R^{23}$;

$R^{23}$ represents a C1-C6 chain hydrocarbon group optionally substituted with one or more halogen atoms, or a phenyl group optionally substituted with one or more substituents selected from Group D, $R^{11a}$ and $R^{12a}$ combine together with a nitrogen atom to which they are attached to form a 3 to 7 membered nonaromatic heterocyclic group, wherein the 3 to 7 membered nonaromatic heterocyclic group represents aziridine, azetidine, pyrrolidine, imidazoline, imidazolidine, piperidine, tetrahydropyrimidine, hexahydropyrimidine, piperazine, azepane, oxazolidine, isooxazolidine, 1,3-oxazinane, morpholine, 1,4-oxazepane, thiazolidine, isothiazolidine, 1,3-thiazinane, thiomorpholine, or 1,4-thiazepane, and the 3 to 7 membered nonaromatic heterocyclic group is optionally substituted with one or more substituents selected from Group E;

$R^{13}$ represents a hydrogen atom, a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, a phenyl group optionally substituted with one or more substituents selected from Group D, or a 5 or 6 membered aromatic heterocyclic group optionally substituted with one or more substituents selected from Group D;

$R^{14}$ represents a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, or a phenyl C1-C3 alkyl group, wherein the phenyl group in the group is optionally substituted with one or more substituents selected from Group D;

$R^{15}$ and $R^{16}$ represent independently of each other, a C1-C6 alkyl group optionally substituted with one or more halogen atoms;

n is 0, 1 or 2;

m is 0, 1 or 2;

x is 0 or 1;

y is 0, 1 or 2;

Group B is selected from the group consisting of a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, a C3-C6 cycloalkyl group optionally substituted with one or more halogen atoms, a cyano group, a hydroxy group, and a halogen atom;

Group D is selected from the group consisting of a C1-C6 chain hydrocarbon group optionally substituted with one or more halogen atoms, a hydroxy group, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a sulfanyl group, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom, wherein $R^{21}$ and $R^{22}$ represent independently of each other a C1-C6 alkyl group optionally substituted with one or more halogen atoms;

Group E is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a halogen atom, an oxo group, a hydroxy group, a cyano group, and a nitro group;

Group F is selected from the group consisting of a C1-C6 alkoxy group optionally substituted with one or more halogen atoms, a $NHR^{21}$, a $NR^{21}R^{22}$, a cyano group, a phenyl group optionally substituted with one or more substituents selected from Group D, a 5 or 6 membered aromatic heterocyclic group optionally substituted with one or more substituents selected from Group D, a C3-C7 cycloalkyl group optionally substituted with one or more halogen atoms, and a 3 to 7 membered non-aromatic heterocyclic group optionally substituted with one or more substituents selected from Group C;

Group C is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, and a halogen atom;

Group G is selected from the group consisting of a halogen atom, and a C1-C6 haloalkyl group.

2. The bipyridine compound according to claim 1, wherein $R^2$ represents an ethyl group.

3. The bipyridine compound according to claim 1, wherein $R^1$ represents a C1-C10 fluoroalkyl group.

4. The bipyridine compound according to claim 1, wherein $R^1$ represents a C1-C10 fluoroalkyl group having two or more fluoro atoms.

5. The bipyridine compound according to claim 1, wherein $R^1$ represents a C1-C10 perfluoroalkyl group.

6. The bipyridine compound according to claim 1, wherein L represents a single bond.

7. The bipyridine compound according to claim 1, wherein
q is 0 or 1, and
$R^3$ represents a halogen atom, or a C1-C6 alkyl group optionally substituted with one or more halogen atoms.

8. The bipyridine compound according to claim 1, wherein:
$R^1$ represents a C1-C10 fluoroalkyl group,
$R^2$ represents an ethyl group,
$R^3$ represents a halogen atom, or a C1-C6 alkyl group optionally substituted with one or more halogen atoms, and
$R^6$ represents a halogen atom, or a C1-C6 alkyl group optionally substituted with one or more halogen atoms.

9. The bipyridine compound according to claim 1, wherein:
$R^1$ represents a C1-C10 perfluoroalkyl group,
$R^2$ represents an ethyl group,
$R^3$ represents a halogen atom, or a C1-C6 alkyl group optionally substituted with one or more halogen atoms, and
p is 0.

10. The bipyridine compound according to claim 1, wherein:
$R^1$ represents a C1-C10 perfluoroalkyl group,
$R^2$ represents an ethyl group, and
p and q are independently of each other 0.

11. A bipyridine compound represented by formula (100):

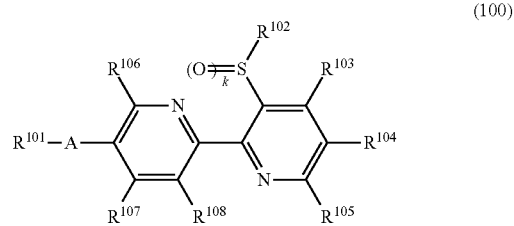

(100)

wherein:
A represents a $S(O)_j$;
$R^{101}$ represents a C2-C10 haloalkyl group, or a (C1-C5 alkoxy) C2-C5 alkyl group substituted with or more halogen atoms,
$R^{102}$ represents a C1-C6 alkyl group optionally substituted with one or more halogen atoms,
$R^{103}$, $R^{104}$, $R^{105}$, $R^{106}$, $R^{107}$, and $R^{108}$ represent independently of each other a hydrogen atom, a halogen atom, or a C1-C6 alkyl group optionally substituted with one or more halogen atoms,
j is 0, 1, or 2; and
k is 0, 1, or 2.

12. The bipyridine compound according to claim 11, wherein:
$R^{101}$ represents a C2-C10 fluoroalkyl group substituted with two or more fluoro atoms, or a (C1-C5 alkoxy) C2-C5 alkyl group substituted with two or more halogen atoms, $R^{102}$ represents an ethyl group, $R^{103}$, $R^{104}$, $R^{105}$, $R^{106}$, $R^{107}$, and $R^{108}$ represent independently of each other a hydrogen atom.

13. A composition for controlling a harmful arthropod comprising the bipyridine compound according to claim 1 and an inert carrier.

14. A method for controlling a harmful arthropod which comprises applying an effective amount of the bipyridine compound according to claim 1 to a harmful arthropod or a habitat where a harmful arthropod lives.

\* \* \* \* \*